(12) United States Patent
Fletcher et al.

(10) Patent No.: US 11,578,117 B2
(45) Date of Patent: Feb. 14, 2023

(54) ANTIBODIES AND FRAGMENTS THEREOF THAT BIND HEPATITIS B VIRUS PROTEIN X

(71) Applicant: Gilead Sciences, Inc., Foster City, CA (US)

(72) Inventors: Simon Paul Fletcher, Burlingame, CA (US); Christian Alfons Voitenleitner, Basel (CH)

(73) Assignee: Gilead Sciences, Inc., Foster City, CA (US)

( * ) Notice: Subject to any disclaimer, the term of this patent is extended or adjusted under 35 U.S.C. 154(b) by 259 days.

(21) Appl. No.: 17/096,803

(22) Filed: Nov. 12, 2020

(65) Prior Publication Data

US 2021/0122808 A1    Apr. 29, 2021

Related U.S. Application Data

(62) Division of application No. 16/372,163, filed on Apr. 1, 2019, now Pat. No. 10,870,691.

(60) Provisional application No. 62/653,378, filed on Apr. 5, 2018.

(51) Int. Cl.

| | | |
|---|---|---|
| *A61K 39/00* | (2006.01) | |
| *C07K 16/28* | (2006.01) | |
| *A61K 39/395* | (2006.01) | |
| *A61K 47/68* | (2017.01) | |
| *C07K 16/30* | (2006.01) | |
| *C07K 16/08* | (2006.01) | |
| *G01N 33/569* | (2006.01) | |
| *G01N 33/50* | (2006.01) | |
| *G01N 33/576* | (2006.01) | |
| *C12N 15/113* | (2010.01) | |

(52) U.S. Cl.
CPC ......... *C07K 16/082* (2013.01); *G01N 33/502* (2013.01); *G01N 33/56983* (2013.01); *G01N 33/5761* (2013.01); *C07K 2317/82* (2013.01); *C12N 15/1131* (2013.01); *C12N 2310/14* (2013.01); *C12N 2320/11* (2013.01); *G01N 2333/02* (2013.01); *G01N 2469/10* (2013.01); *G01N 2800/26* (2013.01)

(58) Field of Classification Search
CPC .......... C07K 2317/92; C07K 2317/565; C07K 2317/76; C07K 2317/24; A61K 2039/505
See application file for complete search history.

(56) References Cited

U.S. PATENT DOCUMENTS

2019/0309052 A1   10/2019  Fletcher et al.

FOREIGN PATENT DOCUMENTS

WO   WO-2019195181 A1   10/2019

OTHER PUBLICATIONS

Intl. Search Report—Written Opinion dated Jun. 27, 2019 for Intl. Appl. No. PCT/US2019/025216.
Jin Y-H et al. (2006), "An intracellular antibody can suppress tumorigenicity in Hepatitis B virus X-expressing cells", Cancer Immunology, Immunotherapy, vol. 55, No. 5, pp. 569-578.
Li J et al. (1995), "Radioimmunoimaging of Human Hepatocellular Carcinoma Xenografts with $^{131}$I-Anti-HBx Monoclonal Antibody", Journal of Experimental and Clinical Cancer Research, vol. 14, No. 1, pp. 25-30.
Mai L et al. (2012), "Small interfering RNA targeting to hepatitis B virus X gene and 5-aza-2'-deoxycytidine on inhibited growth of the subcutaneous implanted tumor of hepatocellular carcinoma in nude mice," Zhonghua Shi Yan He Lin Chuang Bing Du Xue Za Zhi. Oct.;26(5):362-5 (Abstract).
Murphy C M et al. (2016), "Hepatitis B Virus X Protein Promotes Degradation of SMC5/6 to Enhance HBV Replication", Cell Reports, vol. 16, No. 11, pp. 2846-2854.
Ni Q et al. (2004), "Development of a system for quick screening of efficient HBx-siRNA", Zhejiang Daxue Xuebao (Yixue Ban) = Zhejiang University Journal, vol. 33, No. 4, p. 300 (Abstract).
Park O Y et al. (2000), "Characterization and Gene Cloning of Monoclonal Antibody Specific for the Hepatitis B Virus X Protein", Hybridoma, pp. 73-80.
Tang K-F et al. (2008), "Knockdown of damage-specific DNA binding protein 1 (DDB1) enhances the HBx-siRNA-mediated inhibition of HBV replication", Biologicals, vol. 36, No. 3, pp. 177-183.
Wei L et al. (2014), "A broadly reactive monoclonal antibody detects multiple genotypes of hepatitis B virus X protein", Archives of Virology, vol. 159, No. 10, pp. 2731-2735.
Yang L et al. (2010), "907 Sima Targeting to Hepatitis B Virus X and 5-Aza-DC Inhibit Growth of Hepatocellular Carcinoma Cells in Vitro and Vivo Via Rescuing P16 Functions", Journal of Hepatology, vol. 52, p. S352 (Abstract).
Zhang J-F et al. (2018), "A cell-penetrating whole molecule antibody targeting intracellular HBx suppresses hepatitis B virus via TRIM21-dependent pathway", Theranostics, vol. 8, No. 2, pp. 549-562.
Abdul F et al. (2019), "Structure-Function Analysis of the Smc5/6 Complex, a Host Restriction Factor Against Hepatitis B Virus", EMBO Workshop: Organization of bacterial and eukaryotic genomes by SMC complexes, Vienna, Austria, Sep. 10-13, 2019, Poster Presentation.
Beran R et al. (2018), "Inhibition of Hepatitis B Virus X Protein Leads to the Reappearance of the Smc5/6 Complex in HBV-Infected Primary Human Hepatocytes", EASL, Paris, France, Apr. 11-15, 2018, Poster Presentation SAT-366.
Beran R et al. (2018), "Spatiotemporal Analysis of Hepatitis B Virus X Protein (HBx) in HBV-Infected Primary Human Hepatocytes", International HBV Meeting 2018, Taormina, Italy, Oct. 3-6, 2018, Oral Presentation O-72.

(Continued)

*Primary Examiner* — Barry A Chestnut

(57) ABSTRACT

Provided herein are, inter alia, antibodies, antigen-binding antibody fragments, cells, polynucleotides, compositions, kits, and methods relating to the detection of HBV protein X (HBx), e.g., in vitro and in vivo. Included are antibodies and fragments thereof that bind HBx, as well as kits, cells, and compositions comprising such antibodies and fragments.

27 Claims, 14 Drawing Sheets

Specification includes a Sequence Listing.

(56) References Cited

OTHER PUBLICATIONS

Kornyeyev D et al. (2019), "Spatiotemporal Analysis of Hepatitis B Virus X Protein in Primary Human Hepatocytes", J Virol, vol. 93, Issue 16, e00248-19.
Tao S et al. (2019), "Characterization and engineering of broadly reactive monoclonal antibody against hepatitis B virus X protein that blocks its interaction with DDB1", Sci Rep 9, 20323.
Intl. Preliminary Report on Patentability—Written Opinion dated Oct. 15, 2020 for Intl. Appl. No. PCT/US2019/025216.
Notice of Allowance dated Aug. 14, 2020 for U.S. Appl. No. 16/372,163.
Office Action dated Jun. 18, 2020 for U.S. Appl. No. 16/372,163.

FIG. 2C
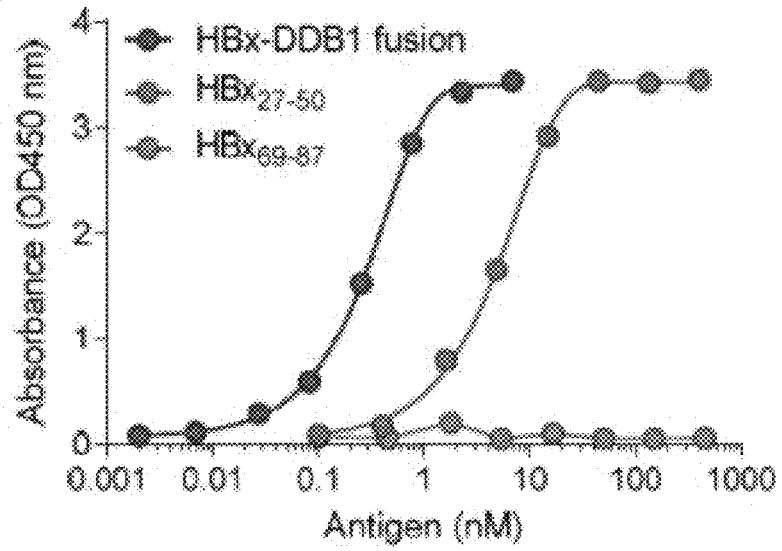
FIG. 2D
```
      27                          50
GTD: GRPPSGSLGTLSSPSPSAVPTDHG
GTA: GRPLSGPLGTLSSPSPSAVPADHG
GTB: GRPLPGPLGALPPASPVVPTDHG
GTC: GRPVSGPFGTLPSPSSSAVPADHG
GTE: GRPVSGSLGDLSSPSPSAVPADHG
```
FIG. 2E
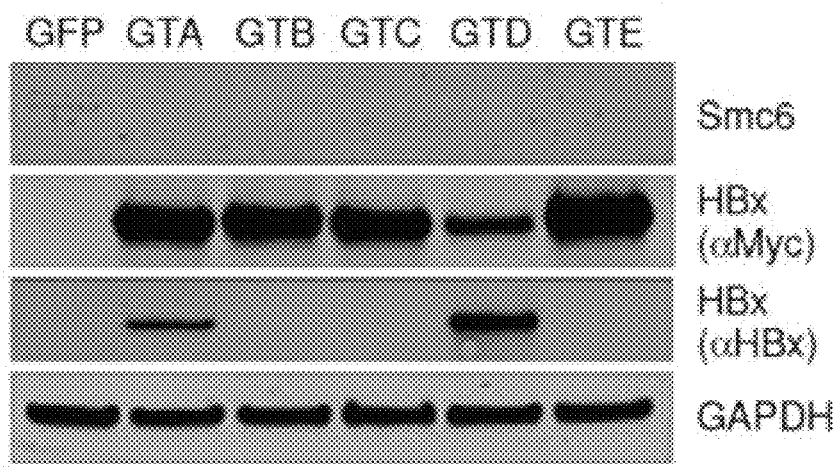
FIGS. 2C-2E

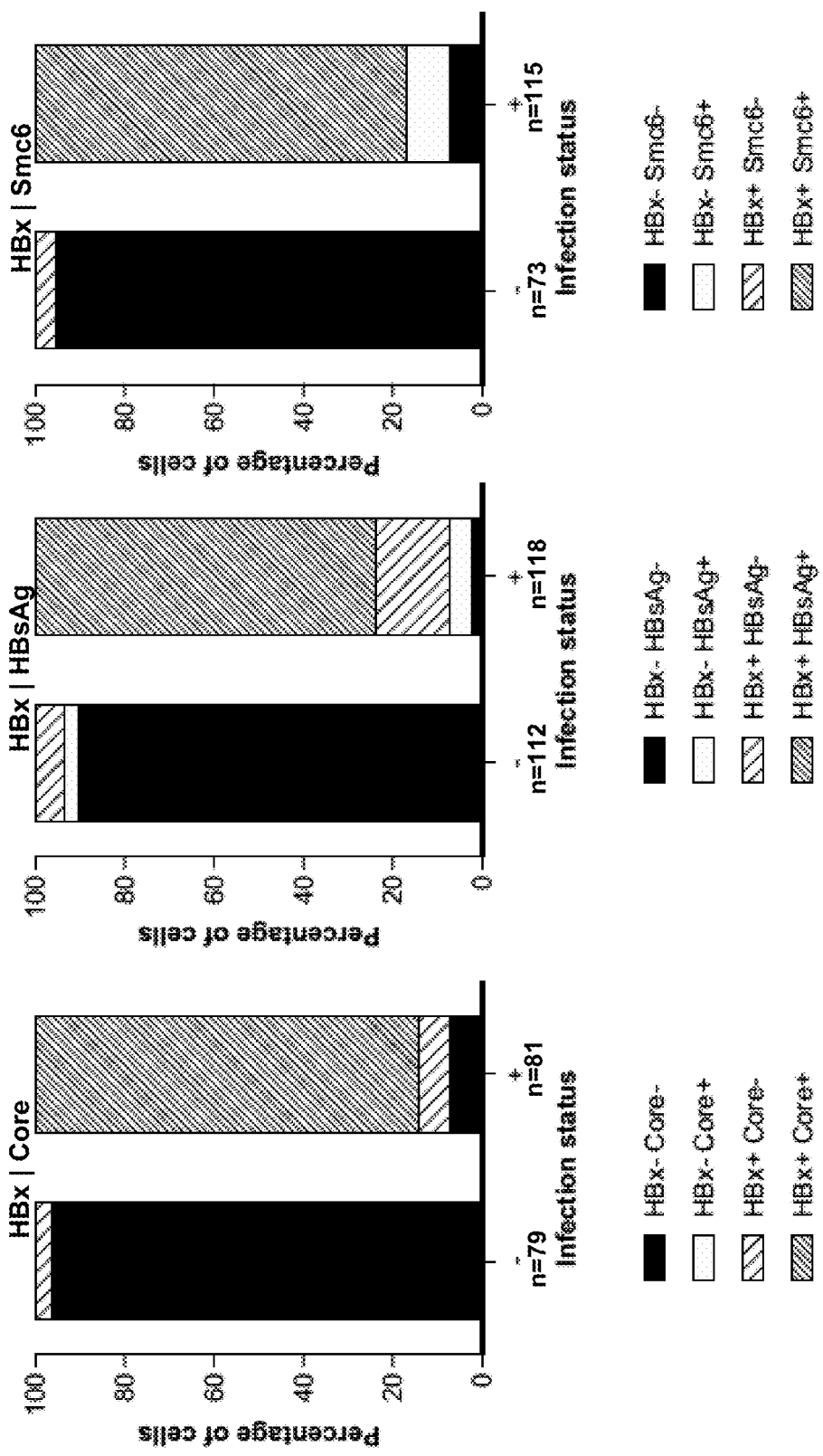

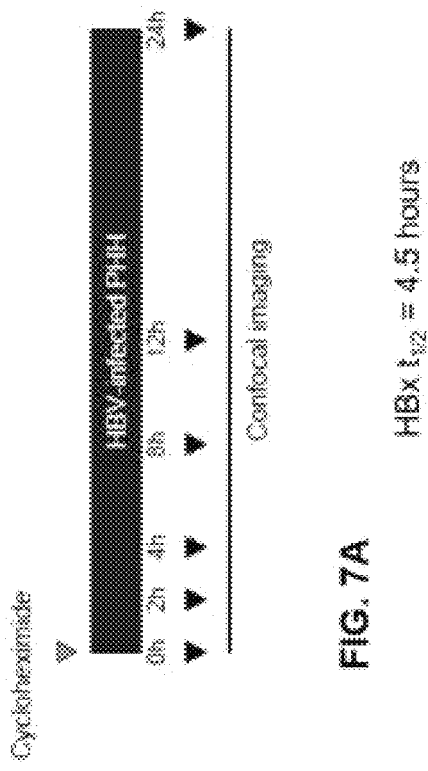
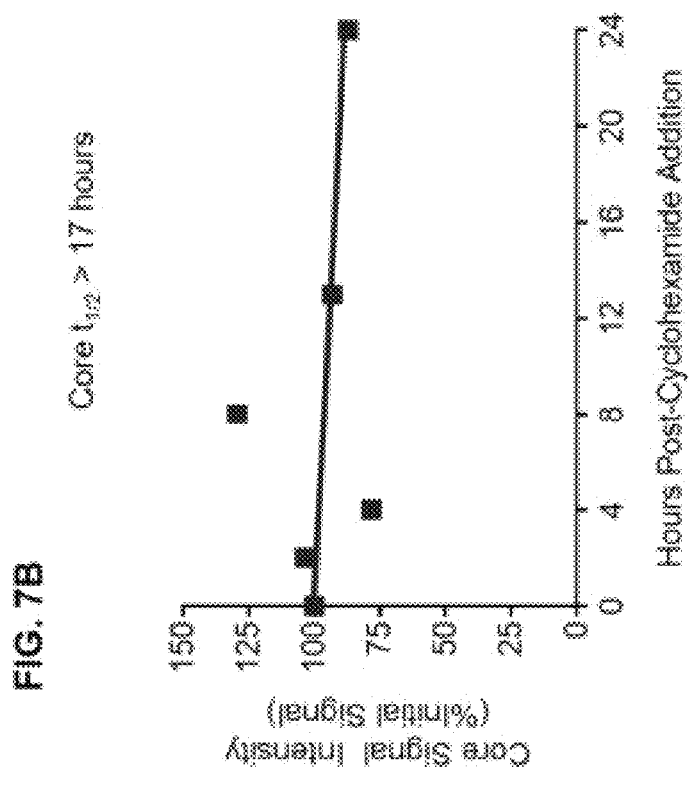
FIG. 7A
FIG. 7B

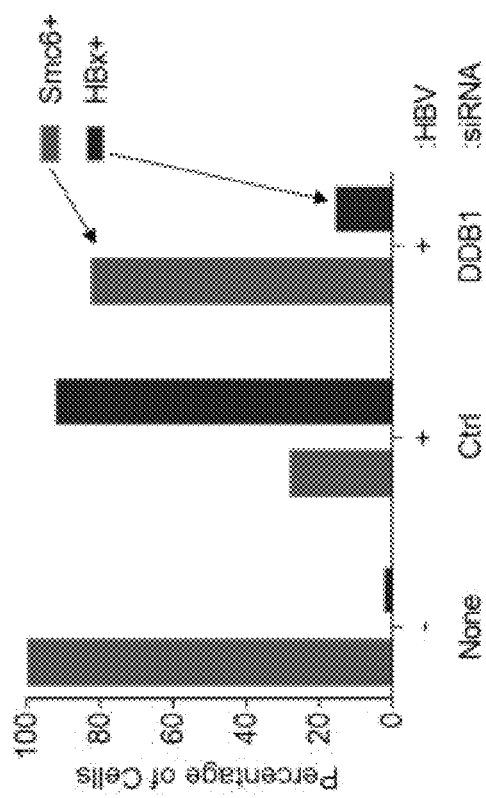
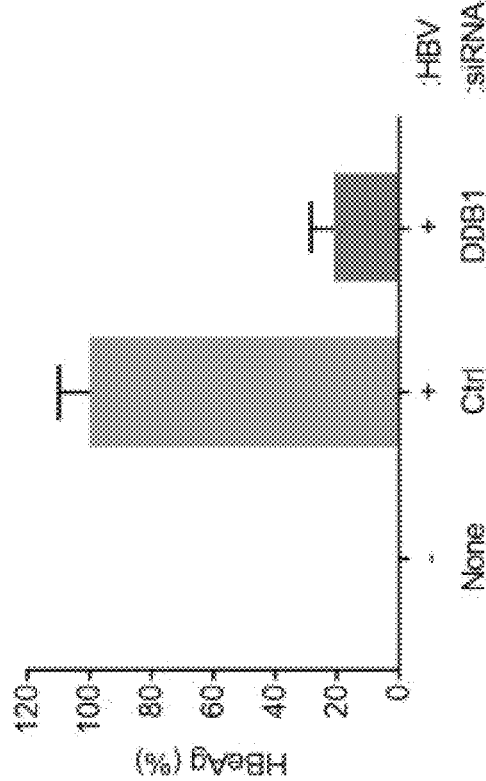
FIG. 9B
FIG. 9A
FIGS. 9A-9B

ANTIBODIES AND FRAGMENTS THEREOF THAT BIND HEPATITIS B VIRUS PROTEIN X

CROSS-REFERENCE TO RELATED APPLICATIONS

This application is a divisional of U.S. patent application Ser. No. 16/372,163, filed on Apr. 1, 2019, issued as U.S. Pat. No. 10,870,691 on Dec. 22, 2020, which claims the benefit under 35 U.S.C. § 119(e) of U.S. Provisional Application No. 62/653,378, filed on Apr. 5, 2018, which are hereby incorporated herein by reference in their entireties for all purposes.

BACKGROUND

Hepatitis B Virus (HBV) causes a liver infection known as Hepatitis B. HBV is transmitted when blood, semen, or another body fluid from a person infected with HBV enters the body of someone who is not infected. In adults, HBV typically causes a transient acute hepatitis; however, a subset of these infections become chronic, which in instances can progress to cirrhosis, hepatocellular carcinoma (HCC) and death. Infected neonates acquire HBV via transmission from their mothers and this results in high rates of chronic infection (>90%) and an increased risk of cirrhosis and hepatocellular carcinoma (HCC). Though an effective vaccine exists, it has been estimated that nearly 2 billion individuals have been infected and of those 400 million are chronically infected (Hoffman and Thio (2007) *Lancet Infect Dis,* 7(6): p. 402-9).

INCORPORATION-BY-REFERENCE OF SEQUENCE LISTING

The content of the text file named "1245_PC_SL2.txt", which was created on Jun. 30, 2020, is filed as part of this application, is 76,592 bytes in size, and is hereby incorporated by reference in its entirety.

BRIEF SUMMARY

Provided herein are, inter alia, antibodies, antigen-binding antibody fragments, cells, polynucleotides, compositions, kits, and methods relating to the detection of HBV X protein (HBx), e.g., in vitro and in vivo. Included are antibodies and antigen-binding fragments thereof that bind HBx, as well as kits, cells, and compositions including such antibodies and antigen-binding fragments thereof. Polynucleotides such as vectors that encode such antibodies (e.g., one or more chains thereof) and antigen-binding antibody fragments are also described. Methods of using the antibodies, antigen-binding antibody fragments, polynucleotides, compositions, and kits are also provided herein. Such methods include (but are not limited to) methods for detecting HBx, drug screening assays, methods for detecting or diagnosing the presence of HBV, methods for detecting integrated HBV DNA and HBV infections, and methods for treating HBV infections. Also provided are methods for producing antibodies and antigen-binding antibody fragments disclosed herein.

In an aspect, provided herein are isolated antibodies and antigen-binding fragments thereof. In certain embodiments, an antibody or antigen-binding fragment thereof includes:

(i) a VH-complementarity determining region (CDR) 1 including
the amino acid sequence of SEQ ID NO:1, or SEQ ID NO:1 having 1 conservative substitution,
the amino acid sequence of SEQ ID NO:6, or SEQ ID NO:6 having 1 or 2 conservative substitutions,
the amino acid sequence of SEQ ID NO:11, or SEQ ID NO:11 having 1 or 2 conservative substitutions, or
the amino acid sequence of SEQ ID NO:15, or SEQ ID NO:15 having from 1 to 3 conservative substitutions;
(ii) a VH-CDR2 including
the amino acid sequence of SEQ ID NO:2, or SEQ ID NO:2 having from 1 to 4 conservative substitutions,
the amino acid sequence of SEQ ID NO:7, or SEQ ID NO:7 having 1 or 2 conservative substitutions,
the amino acid sequence of SEQ ID NO:12, or SEQ ID NO:12 having 1 conservative substitution, or
the amino acid sequence of SEQ ID NO:16, or SEQ ID NO:16 having from 1 to 4 conservative substitutions;
(iii) a VH-CDR3 including
the amino acid sequence LAY (SEQ ID NO: 74),
the amino acid sequence of SEQ ID NO:8, or SEQ ID NO:8 having 1 conservative substitution,
an alanine residue, or
the amino acid sequence LA (SEQ ID NO: 75);
(iv) a VL-CDR1 including
the amino acid sequence of SEQ ID NO:3, or SEQ ID NO:3 having from 1 to 4 conservative substitutions,
the amino acid sequence of SEQ ID NO:9, or SEQ ID NO:9 having 1 or 2 conservative substitutions,
the amino acid sequence of SEQ ID NO:13, or SEQ ID NO:13 having from 1 to 3 conservative substitutions, or
the amino acid sequence of SEQ ID NO:17, or SEQ ID NO:17 having from 1 to 3 conservative substitutions;
(v) a VL-CDR2 including
the amino acid sequence of SEQ ID NO:4, or SEQ ID NO:4 having 1 or 2 conservative substitutions,
the amino acid sequence KAS (SEQ ID NO: 76), or
the amino acid sequence of SEQ ID NO:18, or SEQ ID NO:18 having from 1 to 3 conservative substitutions; and
(vi) a VL-CDR3 including
the amino acid sequence of SEQ ID NO:5, or SEQ ID NO:5 having 1 or 2 conservative substitutions,
the amino acid sequence of SEQ ID NO:10, or SEQ ID NO:10 having 1 or 2 conservative substitutions,
the amino acid sequence of SEQ ID NO:14, or SEQ ID NO:14 having 1 conservative substitution, or
the amino acid sequence of SEQ ID NO:19, or SEQ ID NO:19 having 1 conservative substitution.

In an aspect, provided herein are isolated polynucleotides that encode one or more antibodies or antigen-binding antibody fragments disclosed herein. In some embodiments, the polynucleotide comprises an mRNA or a cDNA encoding an anti-HBx antibody or antigen-binding fragment thereof, as described herein. Further provided are pharmaceutical compositions comprising a polynucleotide encoding an anti-HBx antibody or antigen-binding fragment thereof, as described herein, and a pharmaceutically acceptable excipient.

In an aspect, provided herein are vectors including one or more polynucleotides disclosed herein.

In an aspect, provided herein are kits including one or more antibodies or antigen-binding antibody fragments disclosed herein. In certain embodiments, the kit includes an antibody as described herein, and (i) a detection reagent and/or (ii) a HBx antigen. In certain embodiments, the kit includes a pharmaceutical composition as described herein, and (i) a detection reagent and/or (ii) a HBx antigen.

In an aspect, provided herein are cells including a polynucleotide or vector disclosed herein. Included herein are cells, such as immune cells (e.g., T cells) that express an antibody or antigen-binding antibody fragment disclosed herein. In certain embodiments, the cell is a chimeric antigen receptor (CAR) T-cell that expresses a CAR, wherein the CAR includes an antigen-binding antibody fragment disclosed herein.

In an aspect, provided herein are pharmaceutical compositions including antibodies, antigen-binding antibody fragments, polynucleotides, vectors, and/or cells disclosed herein.

In an aspect, provided herein are methods for detecting HBx. In certain embodiments, such a method includes contacting a sample believed to contain HBx with an antibody or antigen-binding antibody fragment disclosed herein; and detecting binding between HBx and the antibody or antigen-binding antibody fragment. In certain embodiments, such a method includes detecting whether HBx is present in a biological sample by contacting the sample with an antibody or antigen-binding antibody fragment disclosed herein, and detecting binding between HBx and the antibody or antigen-binding antibody fragment, wherein the biological sample is obtained from a subject. In certain embodiments, such a method includes (a) contacting a sample believed to contain HBx with an antibody or antigen-binding antibody fragment disclosed herein; and (b) (i) detecting binding between HBx and the antibody or antigen-binding antibody fragment, or (ii) immunoprecipitating the HBx with the antibody or antigen-binding antibody fragment followed by detecting the HBx.

In an aspect, provided herein are methods for diagnosing a HBV infection in a subject. In certain embodiments, such a method includes (a) contacting a biological sample with an antibody or antigen-binding antibody fragment disclosed herein, wherein the sample is obtained from a subject; (b) detecting binding between HBx and the antibody or antigen-binding antibody fragment; and (c) diagnosing the subject with a HBV infection when the presence of HBx in the biological sample is detected.

In an aspect, provided herein are methods for identifying genomic HBV DNA integration in a cell. In certain embodiments, such a method includes (a) contacting the cell with an antibody or antigen-binding antibody fragment disclosed herein; (b) detecting binding between HBx and the antibody or antigen-binding antibody fragment; and (c) identifying the cell as including integrated genomic HBV DNA when the presence of HBx in the biological sample is detected.

In an aspect, provided herein are methods for identifying whether a compound inhibits HBx. In certain embodiments, such a method includes (a) contacting a sample including a cell or a lysate thereof with an antibody or antigen-binding antibody fragment disclosed herein, wherein the cell has been contacted by the compound and expresses HBx; (b) detecting binding between HBx and the antibody or antigen-binding antibody fragment to determine the level of HBx in the sample; and (c) determining whether the level of HBx in the sample is lower than the level of HBx in a control sample, thereby identifying the compound as a compound that inhibits HBx.

In an aspect, provided herein are methods for identifying whether a compound inhibits HBx binding to an HBx-binding protein. In certain embodiments, such a method includes (a) contacting a sample including the compound, HBx, and the protein with an antibody or antigen-binding antibody fragment disclosed herein; (b) detecting binding between HBx and the protein; and (c) determining whether the level of HBx that is bound to the protein in the sample is lower than the level of HBx that is bound to the protein in a control sample, thereby identifying the compound as a compound that inhibits HBx binding.

In an aspect, provided herein are methods for detecting HBx binding to a protein. In certain embodiments, such a method includes (a) contacting a sample that includes HBx and the protein with an antibody or antigen-binding antibody fragment disclosed herein; and (b) detecting binding between HBx and the protein.

In an aspect, included herein are methods for treating or preventing a HBV infection. In certain embodiments, such a method includes administering to a subject an effective amount of an anti-HBx antibody, antigen-binding antibody fragment, a polynucleotide encoding the anti-HBx or antigen-binding fragment thereof, or a pharmaceutical composition comprising an anti-HBx antibody, antigen-binding antibody fragment, a polynucleotide encoding the anti-HBx or antigen-binding fragment thereof, as provided herein. In certain embodiments, such a method includes administering a treatment regimen for HBV to a subject, wherein the subject has been identified as infected with HBV according to a method disclosed herein. In some embodiments, the subject is infected with HBV. In some embodiments, the subject has been exposed to HBV and is suspected of or at risk of being infected with HBV. In some embodiments, the antibody or antigen-binding antibody fragment is an intrabody. In some embodiments, the method comprises administering the therapeutic agent via a route selected from the group consisting of intravenous and subcutaneous. In some embodiments, the subject is a mammal, e.g., a human or a non-human mammal.

In an aspect, provided herein are methods of producing an antibody or antigen-binding fragment thereof, or a heavy chain or light chain of the antibody. In certain embodiments, such a method includes culturing a cell that includes a polynucleotide that encodes the antibody, antigen-binding antibody fragment, or chain under conditions such that the polynucleotide is expressed and produced. In certain embodiments, the method includes recombinantly expressing the antibody, antigen-binding antibody fragment, or chain in a cell.

In one aspect, provided herein are methods of identifying an siRNA useful for treating or preventing a HBV infection in a subject. In some embodiments, the methods comprise:

a) delivering to or contacting an HBV infected cell an siRNA complementary or substantially complementary to HBx;

b) determining or detecting that the siRNA reduces, inhibits or eliminates the expression of HBx; and c) determining or detecting that the siRNA promotes, increases or restores the expression or protein levels of one or more proteins selected from the group consisting of structural maintenance of chromosomes 6 (SMC6), structural maintenance of chromosomes 5 (SMC5), NSE1 homolog, SMC5-SMC6 complex component (NSMCE1), NSE2 (MMS21) homolog, SMC5-SMC6 complex SUMO ligase (NSMCE2), NSE3 homolog, SMC5-SMC6 complex component (NSMCE3) and/or NSE4 homolog A, SMC5-SMC6 complex component (NSMCE4A); whereby an siRNA useful for treating or preventing a HBV infection is identified. In some embodiments, the one or more of SMC6, SMC5, NSMCE1, NSMCE2, NSMCE3 and/or NSMCE4A are detected in a protein complex.

BRIEF DESCRIPTION OF THE DRAWINGS

FIGS. 2A-2E illustrate validation of the anti-HBx mAb by ELISA and Western blot. Depicted are images showing the validation of the αHBx monoclonal antibody (mAb) by Western Blotting. Primary human hepatocytes (PHH) were transduced with lentivirus or infected with HBV for 4 days. (A) PHH were transduced with a lentivirus expressing Myc-tagged HBx. Cell lysates were analyzed by Western blotting at day 3 post-transduction. (B) PHH were mock-infected or infected with HBV or HBVΔX. Cell lysates were analyzed by Western blotting at day 4 post-infection. (C) Binding of the HBx mAb to recombinant HBx-DDB1 fusion (red circles), HBx27-50 peptide (blue circles) and HBx69-87 peptide (green circles) was evaluated by ELISA. (D) Sequence of genotype (GT) D HBx27-50 as well as the corresponding HBx sequences from genotypes A, B, C, and E. Residues in these HBx sequences that differ from genotype D HBx are indicated in red. FIG. 2D discloses SEQ ID NOS 69-73, respectively, in order of appearance. (E) PHH were transduced with lentiviruses expressing GFP or HBx of genotype (GT) A-E. Cell lysates were analyzed by Western blotting at day 3 post-transduction.

FIG. 4B is a 3D reconstruction, showing that nuclear HBx inversely correlates with the presence of Smc6 and that HBx was not detected in PHH infected with HBx-negative HBV (HBVΔX). FIGS. 4A and 4B: PHH were infected for 13 days. FIG. 4B: Reconstruction prepared with IMARIS software. PHH were mock-infected (uninfected) or infected with HBV or HBVΔX and analyzed by confocal microscopy at day 13 post-infection. (A) PHH were stained for HBx (red) or Smc6 (green). Nuclei were stained with DAPI (blue). Representative confocal images from n=8 independent experiments (8-14 days post-infection) are shown. (B) Three-dimensional reconstruction of uninfected and HBV-infected PHH nuclei stained for HBx (red) and Smc6 (green). Nuclei were stained with DAPI (blue).

FIGS. 5A-5C are a set of graphs showing that nuclear HBx positively correlates with the presence of HBV core protein and HBsAg, but negatively correlates with the presence of Smc6. PHH were fixed on Day 13 post-infection with HBV. The percentage of cells positive for each protein was determined by confocal microscopy (n≥30 cells for each condition). (A-C) Single cell quantitation was performed and each cell defined by HBx and HBsAg (A) status, HBx and nuclear core (B) status, or HBx and nuclear Smc6 (C) status. The plot represents the number of cells in each population, expressed as a percentage of the total nuclei analyzed. The number of cells analyzed for each condition is displayed below the plot.

FIGS. 7A and 7B are graphs showing that HBx has a short half-life in HBV-infected PHH. PHH were infected with HBV for 5 days before addition of 100 μg/mL cyclohexamide. PHH were fixed at various times post-cyclohexamide addition and protein signal intensity was measured by confocal microscopy (HBx, n=2 experiments, Core n=1 experiment). Nuclear HBx and HBV core mean fluorescence intensity levels were measured at the indicated time post-treatment by confocal microscopy and the data fit to a first-order exponential decay equation. The data were fit to a first-order exponential decay equation $([A]=[A]_0 e^{(-kt)}$.

FIGS. 9A and 9B are graphs showing that siDDB1 treatment reduces HBx levels. HBV-infected PHH were transfected with siRNA targeting DDB1 (siDDB1) or a non-targeting control (siCtrl) 3 days post-infection. HBeAg levels on Day 18 post-infection were measured by MSD. The percentage of PHH positive for HBx and Smc6 at day 18 post-infection was determined by confocal microscopy (n≥91 cells per condition).

DETAILED DESCRIPTION

I. General

Figure 1:
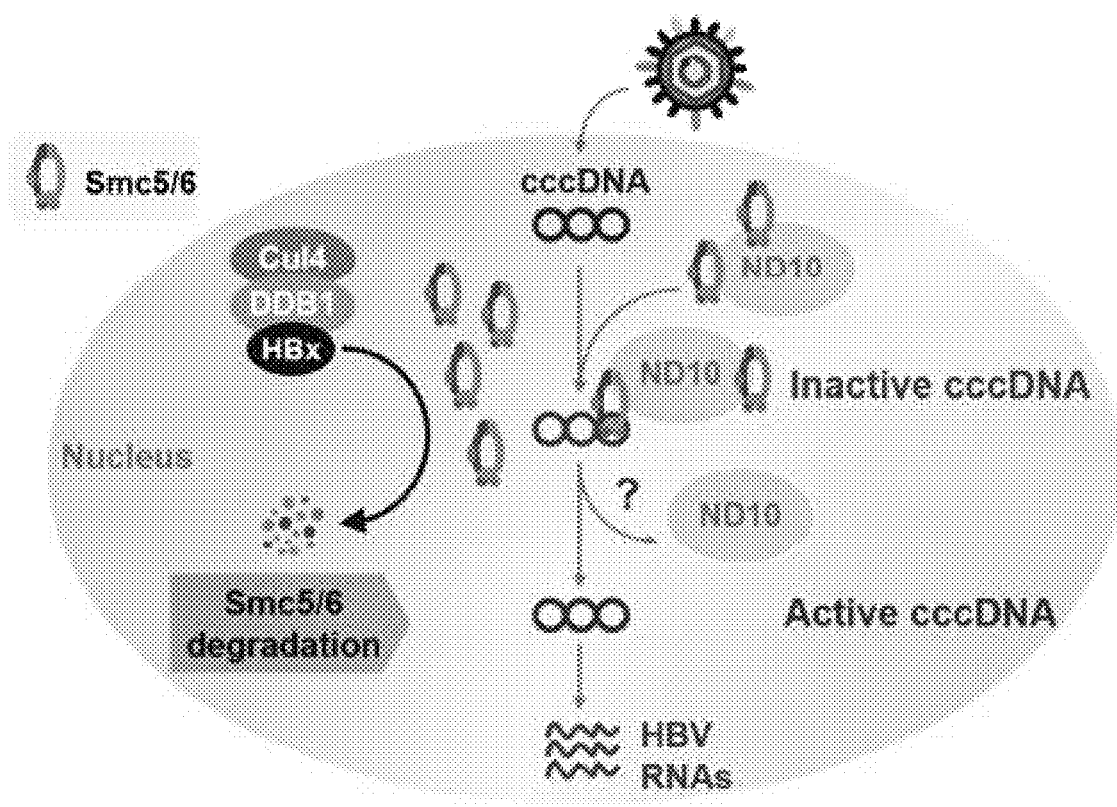
FIG. 1 is a diagram showing that HBx promotes degradation of the Smc5/6 complex to prevent silencing of HBV cccDNA. Abbreviations: cccDNA, covalently closed circular DNA; Cul4, Cullin 4; DDB1, damage-specific DNA-binding protein 1; HBV, hepatitis B virus; HBx, HBV X protein; ND10, nuclear domain 10; Smc5/6, structural maintenance of chromosome 5/6 complex.

Prior to the creation of the antibodies and antigen-binding antibody fragments herein, it was challenging to characterize HBx in HBV-infected cells or in cells with genomic HBV DNA integration and to evaluate the impact of different therapeutic approaches on this important viral protein due to the lack of a highly specific HBx antibody.

In an HBV-infected cell, the cellular structural maintenance of chromosome 5/6 complex (Smc5/6) suppresses cccDNA transcription in the absence of HBx (Decorsière A, et al. Nature 2016; 531:386-9; Murphy C, et al. Cell Rep 2016; 16:2846-54). HBV counters this restriction by expressing HBx, which redirects the cellular DNA damage-binding protein 1 (DDB1)-containing E3 ubiquitin ligase to target Smc5/6 degradation (Decorsière A, et al. Nature 2016; 531:386-9; Murphy C, et al. Cell Rep 2016; 16:2846-54). HBx is an attractive therapeutic target because inhibition of this key viral protein has the potential to transcriptionally silence cccDNA.

We developed a monoclonal antibody that enables detection of HBx protein in HBV-infected primary human hepatocytes (PHH) by Western blot and immunofluorescence. Confocal imaging studies with this antibody demonstrated that HBx is predominantly located in the nucleus of HBV-infected PHH, where it exhibits a diffuse staining pattern. In contrast, a DDB1-binding deficient HBx mutant was detected in both the cytoplasm and nucleus, suggesting that the DDB1 interaction plays a role in the nuclear localization of HBx. Our study also revealed that HBx is expressed early after infection and has a short half-life (~3 hours) in HBV-infected PHH. In addition, we found that treatment with siRNAs that target DDB1 or HBx mRNA decreased HBx protein levels and led to the reappearance of Smc6 in the nuclei of HBV-infected PHH. Collectively, these studies provide the first spatiotemporal analysis of HBx in a natural infection system and also suggest that HBV transcriptional silencing by Smc5/6 can be restored by therapeutic targeting of HBx.

Disclosed herein are tools and methods for the detection, study, and inhibition of HBx, both in vivo and in vitro. In addition to other aspects, anti-HBx antibodies and antigen-binding fragments thereof, as well as related compositions and methods are provided. For example, pharmaceutical compositions and kits including such antibodies and antigen-binding fragments thereof are described herein. Polynucleotides such as vectors that encode such antibodies (e.g., one or more chains thereof) and antigen-binding fragments thereof are also included, as well as cells that contain and express such polynucleotides. In addition to methods for producing the antibodies and antigen-binding fragments thereof, various methods of using the antibodies, antigen-binding antibody fragments, kits, and compositions are also disclosed.

II. Definitions

While various embodiments and aspects of the present disclosure are shown and described herein, it will be obvious to those skilled in the art that such embodiments and aspects are provided by way of example only. Numerous variations, changes, and substitutions will occur to those skilled in the art without departing from the disclosure. It should be understood that various alternatives to the embodiments of the disclosure described herein may be employed in practicing the disclosure.

The section headings used herein are for organizational purposes only and are not to be construed as limiting the subject matter described. All documents, or portions of documents, cited in the application including, without limitation, patents, patent applications, articles, nucleotide and amino acid accession numbers, books, manuals, and treatises are hereby expressly incorporated by reference in their entirety for any purpose.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this disclosure. The following definitions are provided to facilitate understanding of certain terms used frequently herein and are not meant to limit the scope of the present disclosure.

The singular forms "a," "an," and "the" include the plural reference unless the context clearly dictates otherwise.

The term "about" in the context of a numerical value or range means 10% of the numerical value or range recited or claimed, unless the context requires a more limited range.

It is understood that where a parameter range is provided, all integers within that range, and tenths thereof, are also provided by the present disclosure. For example, "0.2-5 mg" is a disclosure of 0.2 mg, 0.3 mg, 0.4 mg, 0.5 mg, 0.6 mg etc. up to and including 5.0 mg.

In the disclosure herein and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

The term "isolated," when applied to a compound (e.g., a nucleic acid or protein), denotes that the nucleic acid or protein is essentially free of cellular components with which it is associated in the natural state. It can be, for example, in a homogeneous state and may be in either a dry or aqueous solution. Purity and homogeneity are typically determined using analytical chemistry techniques such as polyacrylamide gel electrophoresis, column chromatography, thin layer chromatography, or high-performance liquid chromatography (HPLC) analysis. A protein that is the predominant species present in a preparation is substantially purified. An "isolated" or "purified" compound (e.g., a nucleic acid or protein) is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. In certain embodiments, a purified compound is one that is at least 90%, 91%, 92%, 93%, 94%, 95%, 96%, 97%, 98%, 99%, or 100% (w/w) of the desired compound. A purified or isolated polynucleotide (ribonucleic acid (RNA) or deoxyribonucleic acid (DNA)) is free of the genes or sequences that flank it in its naturally-occurring state. Purified also defines a degree of sterility that is safe for administration to a human subject, e.g., lacking infectious or toxic agents. In certain embodiments, an isolated nucleic acid molecule has been separated from a component of its natural environment or from reagents of a synthetic polymerization reaction. In certain embodiments, an isolated nucleic acid molecule is contained in a cell that ordinarily contains the nucleic acid molecule, but the nucleic acid molecule is present extrachromosomally or at a chromosomal location that is different from its natural chromosomal location.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may in certain embodiments be conjugated to a moiety that does not consist of amino acids. The terms apply to amino acid polymers in which one or more amino acid residues is an artificial chemical mimetic of a corresponding naturally occurring amino acid, as well as to naturally occurring amino acid polymers and non-naturally occurring amino acid polymers.

An amino acid residue in a protein "corresponds" to a given residue when it occupies the same essential structural position within the protein as the given residue. For example, a selected residue in a selected protein corresponds to the residue at position 10 of a chain of HBx M19 when the selected residue occupies the same essential structural position as position 10 of the chain of HBx M19. In certain embodiments, where a selected protein is aligned for maximum homology with the chain of HBx M19, the position in the aligned selected protein aligning with position 10 is said to correspond to position 10. Instead of a primary sequence alignment, a three dimensional structural alignment can also be used, e.g., where the structure of a selected antibody or antigen-binding antibody fragment is aligned for maximum correspondence with the human HBx M19 antibody or a fragment thereof and the overall structures compared. In this case, a residue that occupies the same essential structural position as position 10 in the structural model is said to correspond to the position 10 residue. In certain embodiments, a residue of a first protein is at the "same essential structural position" as a residue of a second protein if the residue of the first protein spacially overlaps (at least partially) when crystal structures of the two proteins are superimposed for the maximum overlap of residues. In certain embodiments, the "same essential structural position" is the position at which a residue of a first protein and a residue of a second protein have the same function (e.g., a residue at the position is involved in binding to an epitope or a specific portion thereof or a residue at the position is in a framework region important for the proper orientation of a CDR sequence).

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general, the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

A "substitution" denotes the replacement of one or more amino acids or nucleotides by different amino acids or nucleotides, respectively.

In certain embodiments, a polypeptide variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged.

Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

The terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include genomic DNA (e.g., a gene), a gene fragment, an exon, an intron, intergenic DNA (including, without limitation, heterochromatic DNA), cccDNA, messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may include natural nucleic acid sequences and variants thereof, artificial nucleic acid sequences, or a combination of such sequences. In certain embodiments, a nucleic acid may have any topological conformation, including single-stranded, double-stranded, partially duplexed, triplex, hairpin, circular, or padlocked conformation. The complement of each nucleic acid sequence is disclosed herein. Thus, a reference to a nucleic acid molecule having a particular sequence should be understood to also disclose its complementary strand, with its complementary sequence. In certain embodiments, a nucleic acid is codon-optimized.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

"Percentage of sequence identity" is determined by comparing two optimally aligned sequences over a comparison window, wherein the portion of the polynucleotide or polypeptide sequence in the comparison window may include additions or deletions (i.e., gaps) as compared to the reference sequence (which does not includes additions or deletions) for optimal alignment of the two sequences. In certain embodiments, the percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "identical" or percent "identity," in the context of two or more nucleic acids or polypeptide sequences, refer to two or more sequences or subsequences that are the same or have a specified percentage of amino acid residues or nucleotides that are the same (e.g., 50%, 55%, 60%, 65%, 70%, 75%, 80%, 85%, 90%, 91%, 92%, 93%, 94%, 95%, 96%, 97%, 98%, 99%, or more identity over a specified region, e.g., of an entire polypeptide sequence or an individual domain thereof), when compared and aligned for maximum correspondence over a comparison window, or designated region as measured using a sequence comparison algorithm (e.g., a BLAST or BLAST 2.0 sequence comparison algorithm) with default parameters described below, or by manual alignment and visual inspection (see, e.g., NCBI web site at ncbi.nlm.nih.gov/BLAST/ or the like). Such sequences that are at least about 80% identical are said to be "substantially identical." In some embodiments, two sequences are 100% identical. In certain embodiments, two sequences are 100% identical over the entire length of one of the sequences (e.g., the shorter of the two sequences where the sequences have different lengths). In certain embodiments, identity may refer to the complement of a test sequence. In certain embodiments, the identity exists over a region that is at least about 5 to about 10, about 10 to about 100, about 20 to about 75, about 30 to about 50 amino acids or nucleotides in length. In certain embodiments, the identity exists over a region that is at least about 50 amino acids in length, e.g., over a region that is 100 to 500, 100 to 200, 150 to 200, 175 to 200, 175 to 225, 175 to 250, 200 to 225, 200 to 250 or more amino acids in length.

For sequence comparison, typically one sequence acts as a reference sequence, to which test sequences are compared. In various embodiments, when using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window" refers to a segment of any one of the number of contiguous positions (e.g., least about 10 to about 100, about 20 to about 75, about 30 to about 50,100 to 500, 100 to 200, 150 to 200, 175 to 200, 175 to 225, 175 to 250, 200 to 225, 200 to 250) in which a sequence may be compared to a reference sequence, e.g. of the same number of contiguous positions after the two sequences are optimally aligned. In certain embodiments, a comparison window is the entire length of one or both of two aligned sequences. In certain embodiments, two sequences being compared include different lengths, and the comparison window is the entire length of the longer or the shorter of the two sequences.

Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Preferred examples of algorithms that are suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 may be used, with the parameters described herein, to determine percent sequence identity for nucleic acids and proteins. Software for performing BLAST analyses is publicly available through the National Center for Biotechnology Information (NCBI), as known in the art. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. In certain embodiments, the NCBI BLASTN or BLASTP program is used to align sequences. In certain embodiments, the BLASTN or BLASTP program uses the defaults used by the NCBI. In certain embodiments, the BLASTN program (for nucleotide sequences) uses as defaults: a word size (W) of 28; an expectation threshold (E) of 10; max matches in a query range set to 0; match/mismatch scores of 1,-2; linear gap costs; the filter for low complexity regions used; and mask for lookup table only used. In certain embodiments, the BLASTP program (for amino acid sequences) uses as defaults: a word size (W) of 3; an expectation threshold (E) of 10; max matches in a query range set to 0; the BLOSUM62 matrix (see Henikoff & Henikoff, Proc. Natl. Acad. Sci. USA 89:10915 (1992)); gap costs of existence: 11 and extension: 1; and conditional compositional score matrix adjustment.

The term "buffer" denotes a pharmaceutically acceptable excipient, which stabilizes the pH of a pharmaceutical preparation. Suitable buffers are well known in the art. Suitable pharmaceutically acceptable buffers include but are not limited to acetate-buffers, histidine-buffers, citrate-buffers, succinate-buffers, tris-buffers and phosphate-buffers. In certain embodiments, the concentration of the buffer is from about 0.01 mM to about 1000 mM, about 0.1 mM to about 1000 mM, about 0.1 mM to about 500 mM, about 0.1 mM to about 200 mM, about 0.1 mM to about 100 mM, about 1 mM to about 1000 mM, about 1 mM to about 500 mM, about 1 mM to about 200 mM, about 1 mM to about 100 mM, about 1 mM to about 50 mM, about 2 mM to about 60 mM, about 4 mM to about 60 mM, or about 4 mM to about 40 mM, about 5 mM to about 20 mM, or about 5 mM to about 25 mM.

"Optional" or "optionally" means that the subsequently described event or circumstances may or may not occur, and that the description includes instances where said event or circumstance occurs and instances in which it does not.

"Pharmaceutical composition" refers to a formulation of a compound (e.g., an antibody, antigen-binding antibody fragment, or a polynucleotide such as a vector) or a cell and a medium generally accepted in the art for the delivery of the biologically active compound to mammals, e.g., humans. Such a medium may include any pharmaceutically acceptable carriers, diluents or excipients.

"Pharmaceutically acceptable excipient" and "pharmaceutically acceptable carrier" refer to a substance that aids the administration of an active agent to and/or absorption by a subject and can be included in the compositions of the present disclosure without causing a significant adverse toxicological effect on the subject. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds (e.g., an antibody, antigen-binding antibody fragment, or polynucleotide) of the disclosure. One of skill in the art will recognize that other pharmaceutical excipients are useful in the present disclosure. In certain embodiments, a pharmaceutically acceptable excipient includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The terms "subject," "patient," "individual," and the like are interchangeable and include living members of the animal kingdom suffering from or that may suffer from the indicated disorder (e.g., members of a species including individuals who naturally suffer from the indicated disorder such as HBV infection). In certain embodiments, a subject is a mammal. In certain embodiments, the mammal is a human or a non-human mammal, such as, e.g., a primate (e.g., a human, monkey, ape, chimpanzee, or baboon), mouse, rat, rabbit, monkey, cow, pig, sheep, horse (such as a race horse or work horse), dog (e.g., a companion dog, service dog such as a police dog, military dog, or show dog), livestock animal (such as a pig, cow, donkey, mule, buffalo, goat, camel, or sheep), and/or cat (e.g., a domesticated cat). In certain embodiments, a mammal is a domestic animal, a farm animal, a research animal, a pet, a work animal, or a zoo animal. In certain embodiments, the subject is a human.

"Treatment" or "treat" or "treating" refers to an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

"Delaying" the development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition.

"Prevent" or "prevention" or "preventing" refers to a regimen that protects against the onset of the disease or disorder such that the clinical symptoms of the disease do not develop. Thus, "prevention" relates to administration of a therapy (e.g., administration of a therapeutic substance) to a subject before signs of the disease are detectable in the subject (e.g., administration of a therapeutic substance to a subject in the absence of detectable infectious agent (e.g., virus) in the subject). The subject may be an individual at risk of developing the disease or disorder, such as an individual who has one or more risk factors known to be associated with development or onset of the disease or disorder. Thus, in certain embodiments, the term "preventing HBV infection" refers to administering an anti-HBV therapeutic substance to a subject who does not have a detectable HBV infection. It is understood that the subject for anti-HBV preventative therapy may be an individual at risk of contracting the HBV. It is also understood that prevention does not require a 100% success rate. In some instances, prevention may be understood as a reduction of the risk of infection, but not a complete elimination of the occurrence of an infection.

"At risk individual" is an individual who is at risk of developing a condition to be treated. An individual "at risk" may or may not have detectable disease or condition, and may or may not have displayed detectable disease prior to the methods of treatment described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s).

"Therapeutically effective amount" or "effective amount" refers to an amount that is effective to elicit the desired biological or medical response, including the amount of a compound (e.g., an antibody, antigen-binding antibody fragment, or polynucleotide) or cell that, when administered to a subject for treating a disease, is sufficient to effect such treatment for the disease. The effective amount will vary depending on the compound or cell, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

The term "antibody" means an isolated or recombinant binding agent that includes the necessary variable region sequences to specifically bind an antigenic epitope. Therefore, an antibody is any form of antibody or fragment thereof that exhibits the desired biological activity, e.g., binding the specific target antigen. Thus, it is used in the broadest sense and specifically covers monoclonal antibodies (including full-length monoclonal antibodies), polyclonal antibodies, human antibodies, humanized antibodies, chimeric antibodies, nanobodies, intrabodies, diabodies, multispecific antibodies (e.g., bispecific antibodies), and antibody fragments including but not limited to scFv, Fab, and $Fab_2$, so long as they exhibit the desired biological activity.

The term "human antibody" refers to antibodies containing sequences of human origin, except for possible non-human CDR regions, and does not imply that the full structure of an Ig molecule be present, only that the antibody has minimal immunogenic effect in a human.

"Antibody fragments" include a portion of an intact antibody, for example, the antigen-binding or variable region of the intact antibody. Examples of antibody fragments include Fab, Fab', $F(ab')_2$, and Fv fragments; diabodies; linear antibodies (e.g., Zapata et al., Protein Eng. 8(10): 1057-1062 (1995)); single-chain antibody molecules (e.g., scFv); and multispecific antibodies formed from antibody fragments. Papain digestion of antibodies produces two identical antigen-binding antibody fragments, called "Fab" fragments, each with a single antigen-binding site, and a residual "Fc" fragment, a designation reflecting the ability to crystallize readily. Pepsin treatment yields an $F(ab')_2$ fragment that has two antigen combining sites and is still capable of cross-linking antigen.

"Fv" is a region that consists of a dimer of one heavy- and one light-chain variable region in tight, optionally non-covalent, association. It is in this configuration that the three CDRs of each variable region typically interact to define an antigen-binding site on the surface of the VH-VL dimer. Generally, the six CDRs collectively confer antigen-binding specificity to the antibody, although there are examples of antigen-binding specificity being maintained when one or more of the six CDRs are deleted or modified, e.g., by altering the amino acid sequence of the one or more CDRs, e.g., by amino acid insertion, deletion or substitution. In addition, even a single variable region (or half of an Fv having only three CDRs specific for an antigen) has the ability to recognize and bind antigen, although at a lower affinity than the entire binding site. Residues other than those present in the CDRs may also be important for or play a role in antigen binding and/or specificity.

The term "hypervariable region" refers to the amino acid residues of an antibody that are typically responsible for antigen-binding. The hypervariable region generally includes amino acid residues from a "complementarity determining region" or "CDR" (e.g., around about residues 24-34 (L1), 50-56 (L2) and 89-97 (L3) in the VL, and around about 31-35 (H1), 50-65 (H2) and 95-102 (H3) in the VH when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the VL, and 26-32 (H1), 52-56 (H2) and 95-101 (H3) in the VH when numbered in accordance with the Chothia numbering system; Chothia and Lesk, J. Mol. Biol. 196:901-917 (1987)); and/or those residues from a "hypervariable loop" VCDR (e.g., residues 27-38 (L1), 56-65 (L2) and 105-120 (L3) in the VL, and 27-38 (H1), 56-65 (H2) and 105-120 (H3) in the VH when numbered in accordance with the IMGT numbering system; Lefranc, M. P. et al. Nucl. Acids Res. 27:209-212 (1999), Ruiz, M. e al. Nucl. Acids Res. 28:219-221 (2000)). In certain embodiments, the antibody has symmetrical insertions at one or more of the following points 28, 36 (L1), 63, 74-75 (L2) and 123 (L3) in the VL, and 28, 36 (H1), 63, 74-75 (H2) and 123 (H3) in the VH when numbered in accordance with AHo; Honneger, A. and Plunkthun, A. J. Mol. Biol. 309:657-670 (2001).

The "Fab" fragment is a region on an antibody that binds to antigens. It is composed of one constant and one variable region of each of the heavy and light chains. These regions shape the paratope—the antigen-binding site—at the amino terminal end of the monomer. The two variable regions bind the epitope on their specific antigens. Fab fragments differ from Fab' fragments by the addition of a few residues at the carboxy terminus of the heavy chain $CH_1$ region including one or more cysteines from the antibody hinge region. Fab'-SH is the designation herein for Fab' in which the cysteine residue(s) of the constant regions bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their variable or constant regions. Depending on the amino acid sequence of the constant region of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "scFv" or "sFv" antibody fragments include the VH and VL regions of an antibody, wherein these domains are present in a single polypeptide chain. In certain embodiments, the Fv polypeptide further includes a polypeptide linker between the VH and VL regions, which enables the sFv to form the desired structure for antigen-binding.

The term "diabodies" refers to small antibody fragments with two antigen-binding sites, which fragments include a heavy-chain variable region (VH) connected to a light-chain variable region (VL) in the same polypeptide chain (VH-VL). By using a linker that is too short to allow pairing between the two regions on the same chain, the regions are forced to pair with the complementary regions of another chain and create two antigen-binding sites. Diabodies are described more fully in, for example, EP 404,097; WO 93/11161; and Hollinger et al, Proc. Natl. Acad. Sci. USA, 90:6444-6448 (1993).

An "isolated" antibody or antigen-binding fragment thereof is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In certain embodiments, the antibody will be purified (1) to greater than 95% by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

An antibody or antigen-binding fragment thereof that "specifically binds to" or is "specific for" a particular polypeptide or an epitope on a particular polypeptide is one that binds to that particular polypeptide or epitope on a particular polypeptide without substantially binding to any other polypeptide or polypeptide epitope. In certain embodiments, the antibody of the present disclosure specifically binds to an antigen, e.g., a HBx polypeptide, with a dissociation constant $K_d$ equal to or lower than 100 nM, optionally lower than 10 nM, optionally lower than 1 nM, optionally lower than 0.5 nM, optionally lower than 0.1 nM, optionally lower than 0.01 nM, or optionally lower than 0.005 nM, in the form of monoclonal antibody, scFv, Fab, or other form of antibody measured at a temperature of about 4° C., 25° C., 37° C., or 42° C. Affinities of antibodies can be readily determined using conventional techniques, for example, those described by Scatchard et al. (Ann. N. Y. Acad. Sci. USA 51: 660 (1949), ELISA assays, biolayer interferometry (BLI) assays, and surface plasmon resonance (SPR) assays). Binding properties of an antibody to antigens, cells or tissues thereof may generally be determined and assessed using immunodetection methods including, for example, immunofluorescence-based assays, such as immuno-histochemistry (IHC) and/or fluorescence-activated cell sorting (FACS).

An antibody that "internalizes" is one that is taken up by (i.e., enters) the cell upon binding to an antigen on a mammalian cell (e.g., a cell surface polypeptide or receptor). The internalizing antibody will of course include antigen-binding antibody fragments, human or chimeric antibody, and antibody conjugates. For certain therapeutic applications, internalization in vivo is contemplated. The number of antibody molecules internalized will be sufficient or adequate to kill a cell or inhibit its growth, especially an infected cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the infected cell.

The term "antagonist" antibody is used in the broadest sense, and includes an antibody that partially or fully blocks, inhibits, or neutralizes a biological activity of an epitope, polypeptide, or cell that it specifically binds. Methods for identifying antagonist antibodies may include contacting a polypeptide or cell with a candidate antagonist antibody and measuring a detectable change in one or more biological activities normally associated with the polypeptide or cell.

A "growth inhibitory" anti-HBV antibody is one that binds to an HBV epitope on the surface of infected cells, resulting in measurable growth inhibition of the infected cells. Preferred growth inhibitory antibodies inhibit growth of infected cells by greater than 20%, preferably from about 20% to about 50%, and even more preferably, by greater than 50% (e.g., from about 50% to about 100%) as compared to the appropriate control, the control typically being infected cells not treated with the antibody being tested. In certain embodiments, growth inhibition can be measured at an antibody concentration of about 0.1 µg/ml to about 30 µg/ml or about 0.5 nM to about 200 nM in cell culture, where the growth inhibition is determined 1-10 days after exposure of the infected cells to the antibody. Growth inhibition of infected cells in vivo can be determined in various ways known in the art. In certain embodiments, the antibody is growth inhibitory in vivo if administration of the antibody at about 1 µg/kg to about 100 mg/kg body weight results in reduction of the percent of infected cells or total number of infected cells within about 5 days to 3 months from the first administration of the antibody, preferably within about 5 to 30 days.

An antibody that "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). Preferably the cell is an infected cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody that induces apoptosis is one that results in about 2 to 50 fold, preferably about 5 to 50 fold, and most preferably about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis (e.g., antibody-dependent cell-mediated phagocytosis (ADCP)); down regulation of cell surface receptors (e.g., B cell receptor); and B cell activation.

"Antibody-dependent cell-mediated cytotoxicity" or "ADCC" refers to a form of cytotoxicity in which secreted or exogenously administered Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are required for such killing. The primary cells for mediating ADCC, NK cells, express FcγRIII only, whereas monocytes express FcγRI, FcγRII and FcγRIII. FcR expression on hematopoietic cells is summarized in Table 4 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the antibody or antigen-binding fragment thereof may be assessed in vivo, e.g., in an animal model such as that disclosed in Clynes et al., Proc. Natl. Acad. Sci. (USA) 95:652-656 (1998).

"Fc receptor" or "FcR" describes a receptor that binds to the Fc region of an antibody. In certain embodiments, the FcR is a native sequence human FcR. In certain embodiments, the FcR is one that binds an IgG antibody (a gamma receptor) and includes receptors of the FcγRI, FcγRII, and FcγRIII subclasses, including allelic variants and alternatively spliced forms of these receptors. FCγRII receptors include FcγRIIA (an "activating receptor") and FcγRIIB (an "inhibiting receptor"), which have similar amino acid sequences that differ primarily in the cytoplasmic domains thereof, and FcγRIIC, which includes the FcγRIIB extracellular domain fused to an activating cytoplasmic region. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daeron, Annu. Rev. Immunol. 15:203-234 (1997)). FcRs are reviewed in Ravetch and Kinet, Annu. Rev. Immunol 9:457-92 (1991); Capel et al, Immunomethods 4:25-34 (1994); and de Haas et al, J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al, J. Immunol. 117:587 (1976) and Kim et al, J. Immunol. 24:249 (1994)), and which plays a role in salvaging IgG from lysosomal degradation by FcRn dependent recycling following endocytosis. FcRn binding following pinocytosis in endothelial cells has been shown to be important for sustaining the prolonged pharmacokinetic half-life of antibodies. Assessment of pH dependent human FcRn binding of antibodies in vitro may be performed to provide a prediction of potential for favorable clinical pharmacokinetics (Datta-Mannan and Wroblewski, Drug Metab. Dispos. 42:1867-1872 (2014)).

"Human effector cells" are leukocytes that express one or more FcRs and perform effector functions. Preferably, the human effector cells express at least FcγRIII and perform ADCC effector function. Examples of human effector cells that mediate ADCC include PBMC, NK cells, monocytes, cytotoxic T cells and neutrophils; with PBMCs and NK cells being preferred. The human effector cells may be isolated from a native source, e.g., from blood.

"Complement dependent cytotoxicity" or "CDC" refers to the lysis of a target cell in the presence of a complement. Activation of the classical complement pathway is initiated by the binding of the first component of the complement system (C1q) to antibodies (of the appropriate subclass) that are bound to their cognate antigen. To assess complement activation, a CDC assay, e.g., as described in Gazzano-Santoro et al, J. Immunol. Methods 202: 163 (1996), may be performed.

A "neutralizing antibody" is one that can neutralize the ability of a pathogen to initiate and/or perpetuate an infection in a host and/or in target cells in vitro. The present disclosure provides neutralizing monoclonal human antibodies and antigen-binding fragments thereof, wherein the antibody recognizes an antigen from HBV, e.g., a HBx polypeptide. In certain embodiments, a "neutralizing antibody" may inhibit replication of HBV in a cell. In certain embodiments, the inhibitory concentration of the monoclonal antibody may be less than about 0.0001 µg/ml, less than about 0.001 µg/ml, less than about 0.01 µg/ml, less than about 0.1 µg/ml, less than about 0.5 µg/ml, less than about 1.0 µg/ml, less than about 5 µg/ml, less than about 10 µg/ml, less than about 25 µg/ml, less than about 50 µg/ml, or less than about 100 µg/ml to neutralize about 50% of the input virus in the neutralization assay.

Also provided are "non-neutralizing antibodies," which in certain embodiments are antibodies that bind to HBx but do not neutralize HBV. However, in terms of Fc-mediated killing, the non-neutralizing antibody could still eliminate cells expressing viral antigens that are bound but not neutralized by the antibody. Thus, in certain embodiments, an antibody of the disclosure can bind a viral antigen and eliminate virally infected cells without neutralizing the virus.

The term "operably linked" refers to two or more nucleic acid sequence elements that are usually physically linked and are in a functional relationship with each other. For instance, a promoter is operably linked to a coding sequence if the promoter is able to initiate or regulate the transcription or expression of a coding sequence, in which case, the coding sequence should be understood as being "under the control of" the promoter. In certain embodiments, a vector includes a nucleic acid sequence element that encodes an antibody chain disclosed herein, or a fragment thereof, operably linked to a promoter.

In certain embodiments, a vector is capable of propagating another nucleic acid to which it is linked. In certain embodiments, a vector is a self-replicating nucleic acid structure. In certain embodiments, a vector is incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A polynucleotide "variant" is a polynucleotide that typically differs from a polynucleotide specifically disclosed herein in one or more substitutions, deletions, additions and/or insertions. Such variants may be naturally occurring or may be synthetically generated, for example, by modifying one or more of the polynucleotide sequences of the present disclosure and evaluating one or more biological activities of the encoded polypeptide as described herein and/or using any of a number of techniques well known in the art.

A polypeptide "variant" is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the disclosure and evaluating one or more biological activities of the polypeptide as described herein and/or using any of a number of techniques well known in the art.

The term "variant" may also refer to any naturally occurring or engineered molecule including one or more nucleotide or amino acid mutations. In one embodiment, the molecule is an antibody. For example, somatic variants may encompass all related naturally occurring antibodies that are part of or derived from the same B-cell lineage. Engineered variants may encompass all single mutations or combinatorial mutations made to an antibody.

Modifications may be made in the structure of the polynucleotides and polypeptides of the present disclosure and still obtain a functional molecule that encodes a variant or derivative polypeptide with desirable characteristics. When it is desired to alter the amino acid sequence of a polypeptide to create an equivalent, or even an improved, variant or portion of a polypeptide of the disclosure, one skilled in the art will typically change one or more of the codons of the encoding DNA sequence.

For example, certain amino acids may be substituted for other amino acids in a protein structure without appreciable loss of its ability to bind other polypeptides (e.g., antigens) or cells. Since it is the binding capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the polypeptide sequences of the disclosed antibodies and antigen-binding fragments thereof, or corresponding DNA sequences that encode said polypeptides without appreciable loss of their biological utility or activity.

"Developability" refers to the intrinsic chemical and biophysical properties of an antibody that make it suitable for commercial manufacturing and therapeutic use. These properties may include thermal stability (e.g. melting temperature), low pH stability (e.g. during viral inactivation procedures required during Good Manufacturing Practice production), solubility, viscosity, product homogeneity and chemical stability (e.g. oxidation, deamidation, isomerization, cleavage, glycosylation, glycation, hydroxylation).

"Binding affinity" may refer to a binding dissociate constant (Kd) or an apparent affinity (e.g., EC50) value.

"Percent aggregation" may refer to a percent loss of soluble protein monomer as determined by, e.g., size-exclusion chromatography (SEC). Thus, a percent change in monomer content with a negative value would indicate a loss of monomer and an increase in aggregation, while a percent change in monomer content with a positive value would indicate an increase in monomer and a corresponding decrease in aggregation.

III. Antibodies and Fragments Thereof

In an aspect, provided herein is an isolated antibody, or an antigen-binding fragment thereof. In certain embodiments, the antibody, or an antigen-binding fragment thereof includes:
(i) a VH-CDR1 including
 the amino acid sequence of SEQ ID NO:1, or SEQ ID NO:1 having 1 conservative substitution,
 the amino acid sequence of SEQ ID NO:6, or SEQ ID NO:6 having 1 or 2 conservative substitutions,
 the amino acid sequence of SEQ ID NO:11, or SEQ ID NO:11 having 1 or 2 conservative substitutions, or
 the amino acid sequence of SEQ ID NO:15, or SEQ ID NO:15 having from 1 to 3 conservative substitutions;
(ii) a VH-CDR2 including
 the amino acid sequence of SEQ ID NO:2, or SEQ ID NO:2 having from 1 to 4 conservative substitutions,
 the amino acid sequence of SEQ ID NO:7, or SEQ ID NO:7 having 1 or 2 conservative substitutions,
 the amino acid sequence of SEQ ID NO:12, or SEQ ID NO:12 having 1 conservative substitution, or
 the amino acid sequence of SEQ ID NO:16, or SEQ ID NO:16 having from 1 to 4 conservative substitutions;
(iii) a VH-CDR3 including the amino acid sequence LAY (SEQ ID NO:74),
the amino acid sequence of SEQ ID NO:8, or SEQ ID NO:8 having 1 conservative substitution,
an alanine residue, or
the amino acid sequence LA (SEQ ID NO:75);
(iv) a VL-CDR1 including
the amino acid sequence of SEQ ID NO:3, or SEQ ID NO:3 having from 1 to 4 conservative substitutions,
the amino acid sequence of SEQ ID NO:9, or SEQ ID NO:9 having 1 or 2 conservative substitutions,
the amino acid sequence of SEQ ID NO:13, or SEQ ID NO:13 having from 1 to 3 conservative substitutions, or
the amino acid sequence of SEQ ID NO:17, or SEQ ID NO:17 having from 1 to 3 conservative substitutions;
(v) a VL-CDR2 including
the amino acid sequence of SEQ ID NO:4, or SEQ ID NO:4 having 1 or 2 conservative substitutions,
the amino acid sequence KAS (SEQ ID NO:76), or
the amino acid sequence of SEQ ID NO:18, or SEQ ID NO:18 having from 1 to 3 conservative substitutions; and
(vi) a VL-CDR3 including
the amino acid sequence of SEQ ID NO:5, or SEQ ID NO:5 having 1 or 2 conservative substitutions,
the amino acid sequence of SEQ ID NO:10, or SEQ ID NO:10 having 1 or 2 conservative substitutions,
the amino acid sequence of SEQ ID NO:14, or SEQ ID NO:14 having 1 conservative substitution, or
the amino acid sequence of SEQ ID NO:19, or SEQ ID NO:19 having 1 conservative substitution.

In certain embodiments, the antibody or antigen-binding antibody fragment includes (i) a VH-CDR1 including the amino acid sequence of SEQ ID NO:1, or SEQ ID NO:1 having 1 conservative substitution; (ii) a VH-CDR2 including the amino acid sequence of SEQ ID NO:2, or SEQ ID NO:2 having from 1 to 4 conservative substitutions; (iii) a VH-CDR3 including the amino acid sequence LAY (SEQ ID NO:74); (iv) a VL-CDR1 including the amino acid sequence of SEQ ID NO:3, or SEQ ID NO:3 having from 1 to 4 conservative substitutions; (v) a VL-CDR2 including the amino acid sequence of SEQ ID NO:4, or SEQ ID NO:4 having 1 or 2 conservative substitutions; and (vi) a VL-CDR3 including the amino acid sequence of SEQ ID NO:5, or SEQ ID NO:5 having 1 or 2 conservative substitutions.

In certain embodiments, the antibody or antigen-binding antibody fragment includes (i) a VH-CDR1 including the amino acid sequence of SEQ ID NO:1; (ii) a VH-CDR2 including the amino acid sequence of SEQ ID NO:2; (iii) a VH-CDR3 including the amino acid sequence LAY (SEQ ID NO:74); (iv) a VL-CDR1 including the amino acid sequence of SEQ ID NO:3; (v) a VL-CDR2 including the amino acid sequence of SEQ ID NO:4; and (vi) a VL-CDR3 including the amino acid sequence of SEQ ID NO:5.

In certain embodiments, the antibody or antigen-binding antibody fragment includes (i) a VH-CDR1 including the amino acid sequence of SEQ ID NO:6 or SEQ ID NO:6 having 1 or 2 conservative substitutions; (ii) a VH-CDR2 including the amino acid sequence of SEQ ID NO:7, or SEQ ID NO:7 having 1 or 2 conservative substitutions; (iii) a VH-CDR3 including the amino acid sequence of SEQ ID NO:8, or SEQ ID NO:8 having 1 conservative substitution; (iv) a VL-CDR1 including the amino acid sequence of SEQ ID NO:9, or SEQ ID NO:9 having 1 or 2 conservative substitutions; (v) a VL-CDR2 including the amino acid sequence KAS (SEQ ID NO:76); and (vi) a VL-CDR3 including the amino acid sequence of SEQ ID NO:10, or SEQ ID NO:10 having 1 or 2 conservative substitutions.

In certain embodiments, the antibody or antigen-binding antibody fragment includes (i) a VH-CDR1 including the amino acid sequence of SEQ ID NO:6; (ii) a VH-CDR2 including the amino acid sequence of SEQ ID NO:7; (iii) a VH-CDR3 including the amino acid sequence of SEQ ID NO:8; (iv) a VL-CDR1 including the amino acid sequence of SEQ ID NO:9; (v) a VL-CDR2 including the amino acid sequence KAS (SEQ ID NO:76); and (vi) a VL-CDR3 including the amino acid sequence of SEQ ID NO:10.

In certain embodiments, the antibody or antigen-binding antibody fragment includes (i) a VH-CDR1 including the amino acid sequence of SEQ ID NO:11, or SEQ ID NO:11 having 1 or 2 conservative substitutions; (ii) a VH-CDR2 including the amino acid sequence of SEQ ID NO:12, or SEQ ID NO:12 having 1 conservative substitution; (iii) a VH-CDR3 including an alanine residue; (iv) a VL-CDR1 including the amino acid sequence of SEQ ID NO:13, or SEQ ID NO:13 having from 1 to 3 conservative substitutions; (v) a VL-CDR2 including the amino acid sequence KAS (SEQ ID NO:76); and (vi) a VL-CDR3 including the amino acid sequence of SEQ ID NO:14, or SEQ ID NO:14 having 1 conservative substitution.

In certain embodiments, the antibody or antigen-binding antibody fragment includes (i) a VH-CDR1 including the amino acid sequence of SEQ ID NO:11; (ii) a VH-CDR2 including the amino acid sequence of SEQ ID NO:12: (iii) a VH-CDR3 including an alanine residue; (iv) a VL-CDR1 including the amino acid sequence of SEQ ID NO:13; (v) a VL-CDR2 including the amino acid sequence KAS (SEQ ID NO:76); and (vi) a VL-CDR3 including the amino acid sequence of SEQ ID NO:14.

In certain embodiments, the antibody or antigen-binding antibody fragment includes (i) a VH-CDR1 including the amino acid sequence of SEQ ID NO:15, or SEQ ID NO:15 having from 1 to 3 conservative substitutions; (ii) a VH-CDR2 including the amino acid sequence of SEQ ID NO:16, or SEQ ID NO:16 having from 1 to 4 conservative substitutions; (iii) a VH-CDR3 including the amino acid sequence LA (SEQ ID NO:75); (iv) a VL-CDR1 including the amino acid sequence of SEQ ID NO:17, or SEQ ID NO:17 having from 1 to 3 conservative substitutions; (v) a VL-CDR2 including the amino acid sequence of SEQ ID NO:18, or SEQ ID NO:18 having from 1 to 3 conservative substitutions; and (vi) a VL-CDR3 including the amino acid sequence of SEQ ID NO:19, or SEQ ID NO:19 having 1 conservative substitution.

In certain embodiments, the antibody or antigen-binding antibody fragment includes (i) a VH-CDR1 including the amino acid sequence of SEQ ID NO:15; (ii) a VH-CDR2 including the amino acid sequence of SEQ ID NO:16; (iii) a VH-CDR3 including the amino acid sequence LA (SEQ ID NO:75); (iv) a VL-CDR1 including the amino acid sequence of SEQ ID NO:17; (v) a VL-CDR2 including the amino acid sequence of SEQ ID NO:18; and (vi) a VL-CDR3 including the amino acid sequence of SEQ ID NO:19.

In certain embodiments, the antibody is HBx M19. In certain embodiments, the antibody or antigen-binding antibody fragment includes two VH regions, and each of the VH regions has the same amino acid sequence as the VH regions of HBx M19. In certain embodiments, the antibody or antigen-binding antibody fragment includes two VL regions, and each of the VL regions has the same amino acid sequence as the VL regions of HBx M19. In certain embodiments, the antibody includes the heavy chain and the light chain sequences disclosed in Table 2. In certain embodiments, the antibody includes the heavy chain and the light chain sequences disclosed in Table 3.

Also provided are polypeptide variants of antibody and antigen-binding fragments thereof disclosed herein, including, e.g., intact antibodies, scFvs, heavy chains, light chains, VH regions, and VL regions.

In certain embodiments, the antibody is a variant of HBx M19. In certain embodiments, the fragment is a variant of a HBx M19 fragment. In certain embodiments, the variant includes two VH regions, and each of the VH regions has the same amino acid sequence as the VH regions of HBx M19, but the variant has a different constant region than HBx M19. In certain embodiments, the variant includes two VL regions, and each of the VL regions has the same amino acid sequence as the VL regions of HBx M19, but the variant has a different constant region than HBx M19. In certain embodiments, the only difference between the variant antibody and HBx M19 is the Fc domain of the variant antibody. In certain embodiments, the antigen-binding antibody fragment includes a variant VH region and/or a variant VL region of HBx M19. In certain embodiments, the amino acids of the variant VH region that correspond to the amino acids of VH-CDR1, VH-CDR2, and/or VH-CDR3 are the same as the corresponding amino acids of VH-CDR1, VH-CDR2, and VH-CDR3 of HBx M19 (using Kabat, IMGT, Chothia, or Honegger numbering). In certain embodiments, the amino acids of the variant VL region that correspond to the amino acids of VL-CDR1, VL-CDR2, and/or VL-CDR3 are the same as the corresponding amino acids of VL-CDR1, VL-CDR2, and VL-CDR3 of HBx M19 (using Kabat, IMGT, Chothia, or Honegger numbering). In certain embodiments, the antibody or antigen-binding antibody fragment includes a variant VH region with a variant of the HBx M19 antibody's VH-CDR1, VH-CDR2, or VH-CDR3 (using Kabat, IMGT, Chothia, or Honegger numbering). In certain embodiments, the antibody or antigen-binding antibody fragment includes a variant VL region with a variant of the HBx M19 antibody's VL-CDR1, VL-CDR2, or VL-CDR3 (using Kabat, IMGT, Chothia, or Honegger numbering).

In certain embodiments, the antibody or antigen binding fragment thereof includes two or more of the heavy chain CDRs and two or more of the light chain CDRs of the HBx M19 antibody (using Kabat, IMGT, Chothia, or Honegger numbering). In certain embodiments, the antibody or antigen binding fragment thereof includes all three of the heavy chain CDRs and all three of the light chain CDRs of the HBx M19 antibody (using Kabat, IMGT, Chothia, or Honegger numbering).

In certain embodiments, the antibody or antigen-binding antibody fragment includes a VH region (e.g., one or two VH regions) including an amino acid sequence that is at least 70%, 75%, 80%, 85%, 90%, 95%, 96%, 97%, 98%, or 99% identical to SEQ ID NO: 21 or 22, wherein the amino acid sequence of the VH region has 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions; 0, 1, 2, 3, 4, or 5 amino acid insertions; and/or 0, 1, 2, 3, 4, or 5 amino acid deletions compared to SEQ ID NO: 21 or 22. In certain embodiments, the antibody or antigen-binding antibody fragment includes a VH region including an amino acid sequence that is 100% identical to SEQ ID NO: 21 or 22. In certain embodiments, the VH region has no deletions or insertions compared to SEQ ID NO: 21 or 22. In certain embodiments, the VH region has no deletions compared to SEQ ID NO: 21 or 22. In certain embodiments, the VH region has no insertions compared to SEQ ID NO: 21 or 22. In certain embodiments, the VH region has 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions compared to SEQ ID NO: 21 or 22, wherein 1, 2, 3, 4, 5, 6, 7, 8, 9, 10, 11, 12, 13, 14, 15, 16, 17, 18, 19, 20, 21, 22, 23, 24, 25, 26, 27, 28, 29, or all of the amino acid substitutions are conservative substitutions.

In certain embodiments, the antibody or antigen-binding antibody fragment includes a VH region including an amino acid sequence that is at least 70% identical to SEQ ID NO: 21, wherein the amino acid sequence of the VH region has from 0 to 30 amino acid substitutions, from 0 to 5 amino acid insertions, and/or from 0 to 5 amino acid deletions compared to SEQ ID NO: 21. In certain embodiments, the antibody or antigen-binding antibody fragment includes a VH region including an amino acid sequence that is at least 70% identical to SEQ ID NO: 22, wherein the amino acid sequence of the VH region has from 0 to 30 amino acid substitutions, from 0 to 5 amino acid insertions, and/or from 0 to 5 amino acid deletions compared to SEQ ID NO: 22.

In certain embodiments, the antibody or antigen-binding antibody fragment includes a VL region (e.g., one or two VL regions) including an amino acid sequence that is at least 70%, 75%, 80%, 85%, 90%, 95%, 96%, 97%, 98%, or 99% identical to SEQ ID NO: 23 or 24, wherein the amino acid sequence of the VL region has 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions; 0, 1, 2, 3, 4, or 5 amino acid insertions; and/or 0, 1, 2, 3, 4, or 5 amino acid deletions compared to SEQ ID NO: 23 or 24. In certain embodiments, the antibody or antigen-binding antibody fragment includes a VL region including an amino acid sequence that is 100% identical to SEQ ID NO: 23 or 24. In certain embodiments, the VL region has no deletions or insertions compared to SEQ ID NO: 23 or 24. In certain embodiments, the VL region has no deletions compared to SEQ ID NO: 23 or 24. In certain embodiments, the VL region has no insertions compared to SEQ ID NO: 23 or 24. In certain embodiments, the VL region has 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions compared to SEQ ID NO: 23 or 24, wherein 1, 2, 3, 4, 5, 6, 7, 8, 9, 10, 11, 12, 13, 14, 15, 16, 17, 18, 19, 20, 21, 22, 23, 24, 25, 26, 27, 28, 29, or all of the amino acid substitutions are conservative substitutions.

In certain embodiments, the antibody or antigen-binding antibody fragment includes a VL region including an amino acid sequence that is at least 70% identical to SEQ ID NO: 23, wherein the amino acid sequence of the VL region has from 0 to 30 amino acid substitutions, from 0 to 5 amino acid insertions, and/or from 0 to 5 amino acid deletions compared to SEQ ID NO: 23. In certain embodiments, the antibody or antigen-binding antibody fragment includes a VL region including an amino acid sequence that is at least 70% identical to SEQ ID NO: 24, wherein the amino acid sequence of the VL region has from 0 to 30 amino acid substitutions, from 0 to 5 amino acid insertions, and/or from 0 to 5 amino acid deletions compared to SEQ ID NO: 24.

In certain embodiments, the antibody or antigen-binding antibody fragment includes two VH regions that each include an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 21 or 22. In certain embodiments, the antibody or antigen-binding antibody fragment includes two VL regions that each includes an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 23 or 24.

In certain embodiments, a chain of the antibody or antigen-binding antibody fragment, includes 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions compared to SEQ ID NO: 21, 22, 23, or 24, wherein at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or all of the amino acid substitutions are conservative substitutions. In certain embodiments, the antibody or antigen-binding antibody fragment, or a chain thereof, includes 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 conservative amino acid substitution, 0 nonconservative substitutions, 0 deletions, and 0 substitutions compared to SEQ ID NO: 21, 22, 23, or 24. In certain embodiments, the antibody or antigen-binding antibody fragment, or a chain thereof, includes 1-5 conservative amino acid substitutions, 0 nonconservative substitutions, 0 deletions, and 0 substitutions compared to SEQ ID NO: 21, 22, 23, or 24. In certain embodiments, the antibody or antigen-binding antibody fragment, or a chain thereof, includes 5-10 conservative amino acid substitutions, 0 nonconservative substitutions, 0 deletions, and 0 substitutions compared to SEQ ID NO: 21, 22, 23, or 24. In certain embodiments, the antibody or antigen-binding antibody fragment, or a chain thereof, includes 10-15 conservative amino acid substitutions, 0 nonconservative substitutions, 0 deletions, and 0 substitutions compared to SEQ ID NO: 21, 22, 23, or 24. In certain embodiments, the antibody or antigen-binding antibody fragment, or a chain thereof, includes 15-20 conservative amino acid substitutions, 0 nonconservative substitutions, 0 deletions, and 0 substitutions compared to SEQ ID NO: 21, 22, 23, or 24. In certain embodiments, the antibody or antigen-binding antibody fragment, or a chain thereof, includes 20-30 conservative amino acid substitutions, 0 nonconservative substitutions, 0 deletions, and 0 substitutions compared to SEQ ID NO: 21, 22, 23, or 24.

In certain embodiments, all of the amino acid substitutions are conservative substitution mutations.

In certain embodiments, the antibody or antigen-binding antibody fragment includes a heavy chain constant region including an amino acid sequence that is at least 70% identical to SEQ ID NO: 25. In certain embodiments, the antibody or antigen-binding antibody fragment includes a heavy chain constant region including an amino acid sequence that is at least 75% identical to SEQ ID NO: 25. In certain embodiments, the antibody or antigen-binding antibody fragment includes a heavy chain constant region including an amino acid sequence that is at least 80% identical to SEQ ID NO: 25. In certain embodiments, the antibody or antigen-binding antibody fragment includes a heavy chain constant region including an amino acid sequence that is at least 85% identical to SEQ ID NO: 25. In certain embodiments, the antibody or antigen-binding antibody fragment includes a heavy chain constant region including an amino acid sequence that is at least 90% identical to SEQ ID NO: 25. In certain embodiments, the antibody or antigen-binding antibody fragment includes a heavy chain constant region including an amino acid sequence that is at least 95% identical to SEQ ID NO: 25. In certain embodiments, the antibody or antigen-binding antibody fragment includes a heavy chain constant region including an amino acid sequence that is at least 96% identical to SEQ ID NO: 25. In certain embodiments, the antibody or antigen-binding antibody fragment includes a heavy chain constant region including an amino acid sequence that is at least 97% identical to SEQ ID NO: 25. In certain embodiments, the antibody or antigen-binding antibody fragment includes a heavy chain constant region including an amino acid sequence that is at least 98% identical to SEQ ID NO: 25. In certain embodiments, the antibody or antigen-binding antibody fragment includes a heavy chain constant region including an amino acid sequence that is at least 99% identical to SEQ ID NO: 25. In certain embodiments, the antibody or antigen-binding antibody fragment includes a heavy chain constant region including an amino acid sequence that is 100% identical to SEQ ID NO: 25.

In certain embodiments, the antibody or antigen-binding antibody fragment includes a light chain constant region including an amino acid sequence that is at least 70% identical to SEQ ID NO: 26. In certain embodiments, the antibody or antigen-binding antibody fragment includes a light chain constant region including an amino acid sequence that is at least 75% identical to SEQ ID NO: 26. In certain embodiments, the antibody or antigen-binding antibody fragment includes a light chain constant region including an amino acid sequence that is at least 80% identical to SEQ ID NO: 26. In certain embodiments, the antibody or antigen-binding antibody fragment includes a light chain constant region including an amino acid sequence that is at least 85% identical to SEQ ID NO: 26. In certain embodiments, the antibody or antigen-binding antibody fragment includes a light chain constant region including an amino acid sequence that is at least 90% identical to SEQ ID NO: 26. In certain embodiments, the antibody or antigen-binding antibody fragment includes a light chain constant region including an amino acid sequence that is at least 95% identical to SEQ ID NO: 26. In certain embodiments, the antibody or antigen-binding antibody fragment includes a light chain constant region including an amino acid sequence that is at least 96% identical to SEQ ID NO: 26. In certain embodiments, the antibody or antigen-binding antibody fragment includes a light chain constant region including an amino acid sequence that is at least 97% identical to SEQ ID NO: 26. In certain embodiments, the antibody or antigen-binding antibody fragment includes a light chain constant region including an amino acid sequence that is at least 98% identical to SEQ ID NO: 26. In certain embodiments, the antibody or antigen-binding antibody fragment includes a light chain constant region including an amino acid sequence that is at least 99% identical to SEQ ID NO: 26. In certain embodiments, the antibody or antigen-binding antibody fragment includes a light chain constant region including an amino acid sequence that is 100% identical to SEQ ID NO: 26.

In certain embodiments, the antibody or antigen-binding antibody fragment includes a first antigen-binding domain and a second antigen-binding domain, wherein each of the antigen binding domains includes (i) a heavy chain having an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 27; and/or (ii) a light chain having an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 30. In certain embodiments, the antigen-binding antibody fragment includes one antigen-binding domain including (i)

a heavy chain having an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 27; and/or (ii) a light chain having an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 30.

In certain embodiments, the antibody or antigen-binding antibody fragment is bispecific, and includes one antigen-binding domain that binds HBx and one antigen-binding domain that binds an antigen other than HBx.

In certain embodiments, the antibody or antigen-binding antibody fragment includes an IgA, IgD, IgE, IgG, or IgM heavy chain constant region. In certain embodiments, the antibody or antigen-binding antibody fragment includes an IgA heavy chain constant region. In certain embodiments, the antibody or antigen-binding antibody fragment includes an IgD heavy chain constant region. In certain embodiments, the antibody or antigen-binding antibody fragment includes an IgE heavy chain constant region. In certain embodiments, the antibody or antigen-binding antibody fragment includes an IgG heavy chain constant region. In certain embodiments, the antibody or antigen-binding antibody fragment includes an IgM heavy chain constant region.

In certain embodiments, the antibody or antigen-binding antibody fragment includes a mouse, rabbit, goat, rat, or human IgG heavy chain constant region. In certain embodiments, the antibody or antigen-binding antibody fragment includes a mouse IgG heavy chain constant region. In certain embodiments, the antibody or antigen-binding antibody fragment includes a rabbit IgG heavy chain constant region. In certain embodiments, the antibody or antigen-binding antibody fragment includes a goat IgG heavy chain constant region. In certain embodiments, the antibody or antigen-binding antibody fragment includes a rat IgG heavy chain constant region. In certain embodiments, the antibody or antigen-binding antibody fragment includes a human IgG heavy chain constant region.

In certain embodiments, the antibody or antigen-binding antibody fragment includes a kappa light chain or a lambda light chain. In certain embodiments, the antibody or antigen-binding antibody fragment includes a kappa light chain. In certain embodiments, the antibody or antigen-binding antibody fragment includes a lambda light chain.

In certain embodiments, the antibody or antigen-binding antibody fragment includes a first antigen-binding domain fused directly, or via an intervening amino acid sequence, to a first heavy chain constant region selected from the group consisting of human IgG1, human IgG2, human IgG3, human IgG4, human IgA1, and human IgA2. In certain embodiments, the antibody or antigen-binding antibody fragment includes a first antigen-binding domain fused directly, or via an intervening amino acid sequence, to a first heavy chain constant region, wherein the constant region is from human IgG1 (e.g., IgG1m3 allotype) with the exception that the IgG1 hinge region is replaced with an IgG3 hinge region (e.g., an "open" IgG3 hinge variant "IgG3 C-" described in WO2017/096221). In certain embodiments, the antibody or antigen-binding antibody fragment includes a second antigen-binding domain fused directly, or via an intervening amino acid sequence, to a second heavy chain constant region selected from the group consisting of human IgG1, human IgG2, human IgG3, human IgG4, human IgA1, and human IgA2. In certain embodiments, the antibody or antigen-binding antibody fragment includes a second antigen-binding domain fused directly, or via an intervening amino acid sequence, to a second heavy chain constant region, wherein the constant region is from human IgG1 (e.g., IgG1m3 allotype) with the exception that the IgG1 hinge region is replaced with an IgG3 hinge region (e.g., an "open" IgG3 hinge variant "IgG3 C-" described in WO2017/096221).

In certain embodiments, the first heavy chain constant region is a human IgG1, and the second heavy chain constant region is a human IgG1.

In certain embodiments, the effector function of the first heavy chain constant region and the second heavy chain constant region are reduced or abrogated (e.g., relative to the effector function of the antibody with a wild type IgG1 Fc).

In certain embodiments, the VH is linked directly or via an intervening amino acid sequence (e.g., a G-S linker) to a human IgG1 constant region (e.g., IgG1m3 allotype) that contains 0-10 (e.g., 1, 2, 3, 4, 5, 6, 7, 8, 9, or 10) amino acid substitutions that reduce effector function and/or increase pharmacokinetic half-life of the antibody. In certain embodiments, the antibody has a hinge region from an IgG3 antibody (e.g., an "open" IgG3 hinge variant "IgG3C-" disclosed in WO 2017/096221) and a CH1, CH2, and CH3 region from a human IgG1 antibody (e.g., IgG1m3 allotype).

In certain embodiments, the antibodies and antigen-binding fragments thereof include one or more amino acid sequence modifications in the heavy chain constant region (Fc) as compared to the HBx M19 antibody. In certain embodiments, these modifications increase stability or increase binding affinity of the modified antibody or antigen-binding fragment thereof as compared to the HBx M19 antibody. In certain embodiments, certain of these modifications, or combinations thereof, surprisingly increase antibody effector function or neutralization activity.

In certain embodiments, the antibodies and antigen-binding fragments thereof include one or more amino acid sequence modifications in a heavy chain variable region or a light chain variable region (Fab) as compared to the HBx M19 antibody. In certain embodiments, these modifications increase stability or increase binding affinity of the modified antibody or antigen-binding fragment thereof as compared to the HBx M19 antibody. In certain embodiments, these modifications reduce immunogenicity, isomerization, glycosylation or oxidation of the antibodies or antigen-binding fragments thereof. In certain embodiments, the modification results in the removal of a potential site of isomerization, glycosylation or oxidation from the antibodies or antigen-binding fragments thereof. In certain embodiments, the amino acid substitutions result in increased translation of the antibodies or antigen-binding fragments thereof. In certain embodiments, these modifications increase the % recovery of monomeric IgG from a low pH viral inactivation procedure. In certain embodiments, these modifications increase the HBV neutralization potency of the antibodies or antigen-binding fragments thereof as compared to the HBx M19 antibody when measured against either a single HBV strain, or a sub-set of related HBV strains.

In particular embodiments, the modification includes an amino acid substitution within one or more potential glycosylation sites located in the HBx M19 antibody. N-linked glycosylation sites may include the sequence NX(S/T) where X is any amino acid residue except proline, and wherein the N is glycosylated.

In certain embodiments, the antibodies or antigen-binding fragments thereof include one or more amino acid modification, e.g., substitutions, to enhance translation. For example, the substitution may be of an amino acid encoded by a rare codon, or for which there is only a limited amount of corresponding tRNA present in the cells in which the protein is expressed. In certain embodiments, antibodies or antigen-binding fragments thereof of the present disclosure include one or more such modifications, or amino acid substitutions, e.g., as compared to HBx M19.

In certain embodiments, the antibodies or antigen-binding fragments thereof include one or more amino acid substitutions to enhance stability of the Fab domain as measured by melting temperature.

In certain embodiments, the antibodies or antigen-binding fragments thereof include one or more amino acid substitutions to enhance stability of the Fab domain at low pH, preventing aggregation during a low "pH hold" procedure used to inactivate potential viruses derived from mammalian cell culture during purification of antibodies such as HBx M19.

In certain embodiments, the first antigen-binding domain is fused directly, or via an intervening amino acid sequence, to a first light chain constant region that is a human lambda constant region. In certain embodiments, the second antigen-binding domain is fused directly, or via an intervening amino acid sequence, to a second light chain constant region that is a human lambda constant region.

In certain embodiments, the antibody or antigen-binding antibody fragment is a linear antibody or a diabody. In certain embodiments, the antibody or antigen-binding antibody fragment is a linear antibody. In certain embodiments, the antibody or antigen-binding antibody fragment is a diabody.

In certain embodiments, the antibody is a kappa-lambda body, an anti-pMHC TCR-like antibody, a dual-affinity re-targeting molecule (DART), a knob-in-hole, a strand-exchange engineered domain body (SEEDbody), a Bispecific T cell engager (BiTe), a CrossMab, an Fcab, a Diabody, a Tandem diabody (TandAb), or a DuoBody®.

In certain embodiments, the antibody or antigen-binding antibody fragment is an intrabody. An "intrabody" is an antibody that is expressed and functions intracellularly. Intrabodies, in certain embodiments, lack disulfide bonds and are capable of modulating the expression or activity of target genes or proteins through their specific binding activity. In certain embodiments, intrabodies include single domain fragments such as isolated VH and VL regions and scFvs. In certain embodiments, an intrabody can include a sub-cellular trafficking signal (e.g., such as a nuclear or mitochondrial localization signal) attached to the N or C terminus of the intrabody to allow it to be expressed at high concentrations in the sub-cellular compartments where a target protein is located. In certain embodiments, an intrabody is a fragment of an antibody. In certain embodiments, an intrabody is or includes a scFv. In certain embodiments, an intrabody is or includes a Fab. In certain embodiments, an intrabody includes a modification of an immunoglobulin VL region for hyperstability, is resistant to the reducing intracellular environment, and/or is expressed as a fusion protein with maltose binding protein or another stable intracellular protein. In certain embodiments, the intrabody includes the functional variable domain of a heavy-chain-only antibody of the family Camelidae (e.g., a chimeric variant of such an antibody including a variable domain described herein and/or 1, 2, 3, 4, 5, or 6 CDRs described herein), but no light chain. Non-limiting descriptions relating to intrabodies are provided in Serruys et al. (2009) *Hepatology* 49 (1): 39-49; U.S. Application Publication No. US20030104402A1, published Jun. 5, 2003; Chen et al. (1994) *Human gene therapy* 5 (5): 595-601; Cohen et al. (1998) *Oncogene* 17 (19): 2445-56; Mhashilkar et al. (1995) *The EMBO Journal* 14 (7): 1542-51; Yurong et al. (2003) *The FASEB Journal* 17: 1733-5; Cohen (1998) *Oncogene* 17 (19): 2445-56; Auf Der Maur et al. (2001) *FEBS Letters* 508 (3): 407-12; Shaki-Loewenstein et al. (2005) *Journal of immunological methods* 303 (1-2): 19-39; Mukhtar et al. (2009) *The International Journal of Biochemistry & Cell Biology* 41 (3): 554-60; Filesi et al. (2007) *Journal of Neurochemistry* 101 (6): 1516-26; Strebe et al. (2009) *Journal of immunological methods* 341 (1-2):30-40; Zhou and Przedborski (2009) *Biochimica et Biophysica Acta* 1792 (7): 634-42; and Cardinale and Biocca (2008) *Trends in Molecular Medicine* 14 (9): 373-80, the entire contents of each of which are incorporated herein by reference. Serruys et al. (2009) *Hepatology* 49 (1): 39-49, which is incorporated by reference herein, describes llama-derived single-domain intrabodies that inhibit secretion of hepatitis B virions in mice.

In certain embodiments, the antibody or antigen-binding antibody fragment further includes a nuclear localization signal or a mitochondrial localization signal. In certain embodiments, the antibody or antigen-binding antibody fragment further includes a nuclear localization signal. Non-limiting examples of nuclear localization signals include GGSGPPKKKRKV (SEQ ID NO: 42), PKKKRKV (SEQ ID NO: 43), KR[PAATKKAGQA] KKKK (SEQ ID NO: 44), KR[XXXXXXXXXX]KKKK (SEQ ID NO: 45), KKXK (SEQ ID NO: 46), KRXK (SEQ ID NO: 47), KKXR (SEQ ID NO: 48), KRXR (SEQ ID NO: 49), and AVKR-PAATKKAGQAKKKKLD (SEQ ID NO: 50), MSRRR-KANPTKLSENAKKLAKEVEN (SEQ ID NO: 51), PAAKRVKLD (SEQ ID NO: 52), PPKKKRKV (SEQ ID NO: 53), and KLKIKRPVK (SEQ ID NO: 54), where X is any amino acid. In certain embodiments, the nuclear localization signal is at an N-terminus of the intrabody. In certain embodiments, the nuclear localization signal is at a C-terminus of the intrabody. In certain embodiments, the antibody or antigen-binding antibody fragment further includes a mitochondrial localization signal. A non-limiting example of a mitochondrial localization signal includes MLSLRQ-SIRFFKPATRTLCSSRYLL (SEQ ID NO: 55). In certain embodiments, the mitochondrial localization signal is at an N-terminus of the intrabody. In certain embodiments, the mitochondrial localization signal is at a C-terminus of the intrabody.

In certain embodiments, the antibody or antigen-binding antibody fragment is a monoclonal antibody In certain embodiments, the antibody or antigen-binding antibody fragment is a humanized antibody or a chimeric antibody. In certain embodiments, the antibody or antigen-binding antibody fragment is a humanized antibody. In certain embodiments, the antibody or antigen-binding antibody fragment is a chimeric antibody.

In certain embodiments, included herein are antigen-binding fragments of antibodies. In certain circumstances, there are advantages of using antigen-binding antibody fragments, rather than whole antibodies. For example, the smaller size of the fragments allows for rapid clearance, and may lead to improved access to certain tissues, such as solid tumors. Examples of antigen-binding antibody fragments include: Fab, Fab', F(ab')$_2$ and Fv fragments; diabodies; linear antibodies; single-chain antibodies; nanobodies; and multispecific antibodies formed from antigen-binding antibody fragments.

In certain embodiments, the antibody of choice is a single chain Fv fragment (scFv). See WO 93/16185; U.S. Pat. Nos. 5,571,894; and 5,587,458. Fv and sFv are the species with intact combining sites that are devoid of constant regions. Thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. In certain embodiments, the antigen-binding antibody fragment may also be a linear antibody, e.g., as described in U.S. Pat. No. 5,641,870. Such linear antibody fragments may be monospecific or bispecific.

In certain embodiments, the antibody is a diabody, linear antibody, single-chain antibody, or nanobody. In certain embodiments, the antibody or antigen-binding antibody fragment is a scFv, sc(Fv)$_2$, Fab, F(ab)$_2$, Fab', F(ab')$_2$, or Fv fragment. In certain embodiments, the antibody or antigen-binding antibody fragment is a scFv. In certain embodiments, the antibody or antigen-binding antibody fragment is a sc(Fv)$_2$. In certain embodiments, the antibody or antigen-binding antibody fragment is a Fab. In certain embodiments, the antibody or antigen-binding antibody fragment is a F(ab)$_2$. In certain embodiments, the antibody or antigen-binding antibody fragment is a Fab'. In certain embodiments, the antibody or antigen-binding antibody fragment is a F(ab')$_2$. In certain embodiments, the antibody or antigen-binding antibody fragment is a Fv fragment.

In certain embodiments, the antibody or antigen-binding antibody fragment further includes a cytotoxic agent, a radioisotope, a therapeutic agent, an anti-viral agent, or a detectable label. In certain embodiments, the antibody or antigen-binding antibody fragment further includes a cytotoxic agent. In certain embodiments, the antibody or antigen-binding antibody fragment further includes a radioisotope. In certain embodiments, the antibody or antigen-binding antibody fragment further includes a therapeutic agent. In certain embodiments, the antibody or antigen-binding antibody fragment further includes an anti-viral agent. In certain embodiments, the antibody or antigen-binding antibody fragment further includes a detectable label.

TABLE 1

Sequences for Exemplary Anti-HBx Antibody HBx M19

| Antibody | HBx M19 |
| --- | --- |
| Heavy Chain | EVQLQQSGPELVKPGASVKISCQASGYTFTDYYMNWVKQSHGKRLE WIGDINPNNGGTAYNQKFKGKATLTVDRSSSTAYMEVRSLTSEDSA VYFCALLAYWGQGTLVTVSAAKTTPPSVYPLAPGSAAQTNSMVTLG CLVKGYFPEPVTVTWNSGSLSSGVHTFPAVLQSDLYTLSSSVTVPS STWPSQTVTCNVAHPASSTKVDKKIVPRDCGCKPCICTVPEVSSVF IFPPKPKDVLTITLTPKVTCVVVDISKDDPEVQFSWFVDDVEVHTA QTKPREEQINSTFRSVSELPIMHQDWLNGKEFKCRVNSAAFPAPIE KTISKTKGRPKAPQVYTIPPPKEQMAKDKVSLTCMITNFFPEDITV EWQWNGQPAENYKNTQPIMDTDGSYFVYSKLNVQKSNWEAGNTFTC SVLHEGLHNHHTEKSLSHSPGK (SEQ ID NO: 27) |
| Heavy Chain -(D)-J Sequence | WGQGTLVTVSA (SEQ ID NO: 29) |
| Heavy CDR1 Kabat | DYYMN (SEQ ID NO: 1) |
| Heavy CDR2 Kabat | DINPNNGGTAYNQKFKG (SEQ ID NO: 2) |
| Heavy CDR3 Kabat | LAY |
| Heavy CDR1 IMGT | GYTFTDYY (SEQ ID NO: 6) |
| Heavy CDR2 IMGT | INPNNGGT (SEQ ID NO: 7) |
| Heavy CDR3 IMGT | ALLAY (SEQ ID NO: 8) |
| Heavy CDR1 Chothia | GYTFTDY (SEQ ID NO: 11) |
| Heavy CDR2 Chothia | PNNG (SEQ ID NO: 12) |
| Heavy CDR3 Chothia | A |
| Heavy CDR1 Honegger | ASGYTFTDYY (SEQ ID NO: 15) |
| Heavy CDR2 Honegger | INPNNGGTAYNQKFKGK (SEQ ID NO: 16) |
| Heavy CDR3 Honegger | LA |
| Heavy Chain Variable Region withoutthe4D)J Sequence | EVQLQQSGPELVKPGASVKISCQASGYTFTDYYMNWVKQSHGKRLE WIGDINPNNGGTAYNQKFKGKATLTVDRSSSTAYMEVRSLTSEDSA VYFCALLAY (SEQ ID NO: 21) |

TABLE 1-continued

Sequences for Exemplary Anti-HBx Antibody HBx M19

| Antibody | HBx M19 |
|---|---|
| Heavy Chain Variable Region | EVQLQQSGPELVKPGASVKISCQASGYTFTDYYMNWVKQSHGKRLE WIGDINPNNGGTAYNQKFKGKATLTVDRSSSTAYMEVRSLTSEDSA VYFCALLAYWGQGTLVTVSA (SEQ ID NO: 22) |
| Heavy Chain Constant Region | AKTTPPSVYPLAPGSAAQTNSMVTLGCLVKGYFPEPVTVTWNSGSL SSGVHTFPAVLQSDLYTLSSSVTVPSSTWPSQTVTCNVAHPASSTK VDKKIVPRDCGCKPCICTVPEVSSVFIFPPKPKDVLTITLTPKVTC VVVDISKDDPEVQFSWFVDDVEVHTAQTKPREEQINSTFRSVSELP IMHQDWLNGKEFKCRVNSAAFPAPIEKTISKTKGRPKAPQVYTIPP PKEQMAKDKVSLTCMITNFFPEDITVEWQWNGQPAENYKNTQPIMD TDGSYFVYSKLNVQKSNWEAGNTFTCSVLHEGLHNHHTEKSLSHSP GK (SEQ ID NO: 25) |
| Light Chain | DVVMTQTPLSLPVSLGDQASISCRSSQSLVYSDGNTHLHWYLQKTG QSPKLLIYKASNRFSGVPDRFSGSGSGTDFTLKISRVEAEDLGVYF CSQSTHVPLTFGAGTKLELKRADAAPTVSIFPPSSEQLTSGGASVV CFLNNFYPKDINVKWKIDGSERQNGVLNSWTDQDSKDSTYSMSSTL TLTKDEYERHNSYTCEATHKTSTSPIVKSFNRGEC (SEQ ID NO: 30) |
| Light Chain -(D)-J Sequence | FGAGTKLELK (SEQ ID NO: 32) |
| Light CDR1 Kabat | RSSQSLVYSDGNTHLH ( SEQ ID NO: 3) |
| Light CDR2 Kabat | KASNRFS (SEQ ID NO: 4) |
| Light CDR3 Kabat | SQSTHVPLT (SEQ ID NO: 5) |
| Light CDR1 IMGT | QSLVYSDGNTH (SEQ ID NO: 9) |
| Light CDR2 IMGT | KAS |
| Light CDR3 IMGT | SQSTHVPLT (SEQ ID NO: 10) |
| Light CDR1 Chothia | SQSLVYSDGNTH (SEQ ID NO: 13) |
| Light CDR2 Chothia | KAS |
| Light CDR3 Chothia | STHVPL (SEQ ID NO: 14) |
| Light CDR1 Honegger | SSQSLVYSDGNTH (SEQ ID NO: 17) |
| Light CDR2 Honegger | KASNRFSGVPDR (SEQ ID NO: 18) |
| Light CDR3 Honegger | STHVPL (SEQ ID NO: 19) |
| Light Chain Variable Region without the -(D)-J Sequence | DVVMTQTPLSLPVSLGDQASISCRSSQSLVYSDGNTHLHWYLQKTG QSPKLLIYKASNRFSGVPDRFSGSGSGTDFTLKISRVEAEDLGVYF CSQSTHVPLT (SEQ ID NO: 23) |
| Light Chain Variable Region | DVVMTQTPLSLPVSLGDQASISCRSSQSLVYSDGNTHLHWYLQKTG QSPKLLIYKASNRFSGVPDRFSGSGSGTDFTLKISRVEAEDLGVYF CSQSTHVPLTFGAGTKLELK (SEQ ID NO: 24) |
| Light Chain Constant Region | RADAAPTVSIFPPSSEQLTSGGASVVCFLNNFYPKDINVKWKIDGS ERQNGVLNSWTDQDSKDSTYSMSSTLTLTKDEYERHNSYTCEATHK TSTSPIVKSFNRGEC (SEQ ID NO: 26) |

Non-limiting examples of leader peptides that may be present at the N-terminus of the heavy chain include MGWSWVFLFLLSGTAGVLS (SEQ ID NO: 28) and MKWVTFISLLFLFSSAYS (SEQ ID NO: 59). Non-limiting examples of leader peptides that may be present at the N-terminus of the light chain include MKLPVRLL-VLMFWIPASSS (SEQ ID NO: 31) and MKWVTFISLL-FLFSSAYS (SEQ ID NO: 59). In certain embodiments, the antibody does not comprise a leader peptide. In certain embodiments, such leader peptides are cleaved and not present in the final antibody.

The placement of sequences in Table 1 within the Light and Heavy Chains of HBx M19 is depicted below (together with an optional leader peptide).

Light chain (including constant region)
(SEQ ID NO: 63)
MKLPVRLLVLMFWIPASSSDVVMTQTPLSLPVSLGDQASISC
RSSQSLVYSDGNTHLHWYLQKTGQSPKLLIYKASNRFSGVPDRFSGSGS
GTDFTLKISRVEAEDLGVYFCSQSTHVPLTFGAGTKLELKRADAAPTVS
IFPPSSEQLTSGGASVVCFLNNFYPKDINVKWKIDGSERQNGVLNSWTD
QDSKDSTYSMSSTLTLTKDEYERHNSYTCEATHKTSTSPIVKSFNRGEC Heavy chain (including constant region)
(SEQ ID NO: 62)
MGWSWVFLFLLSGTAGVLSEVQLQQSGPELVKPGASVKISCQASGYTFT
DYYMNWVKQSHGKRLEWIGDINPNNGGTAYNQKFKGKATLTVDRSSSTA
YMEVRSLTSEDSAVYFCALLAYWGQGTLVTVSAAKTTPPSVYPLAPGSA
AQTNSMVTLGCLVKGYFPEPVTVTWNSGSLSSGVHTFPAVLQSDLYTLS
SSVTVPSSTWPSQTVTCNVAHPASSTKVDKKIVPRDCGCKPCICTVPEV
SSVFIFPPKPKDVLTITLTPKVTCVVVDISKDDPEVQFSWFVDDVEVHT
AQTKPREEQINSTFRSVSELPIMHQDWLNGKEFKCRVNSAAFPAPIEKT
ISKTKGRPKAPQVYTIPPPKEQMAKDKVSLTCMITNFFPEDITVEWQWN
GQPAENYKNTQPIMDTDGSYFVYSKLNVQKSNWEAGNTFTCSVLHEGLH
NHHTEKSLSHSPGK Legend for the light chain and heavy chain sequences shown above (using Kabat):
Leader peptide (exemplary and not present in final antibody)
Framework
CDR
*-(D)-J*
Constant region

TABLE 2

Sequences for Additional Exemplary Anti-HBx Antibody Comprising the Variable Regions of HBx M19

| Antibody | Exemplary Variant of HBx M19 |
|---|---|
| Heavy Chain | EVQLQQSGPELVKPGASVKISCQASGYTFTDYYMNWVKQSHGKRLEWIGDINPNNGGTAYNQKFKGKATLTVDRSSSTAYMEVRSLTSEDSAVYFCALLAYWGQGTLVTVSAAKTTPPSVYPLAPGSAAQTNSMVTLGCLVKGYFPEPVTVTWNSGSLSSGVHTFPAVLQSDLYTLSSSVTVPSSTWPSETVTCNVAHPASSTKVDKKIVPRDCGCKPCICTVPEVSSVFIFPPKPKDVLTITLTPKVTCVVVDISKDDPEVQFSWFVDDVEVHTAQTQPREEQFNSTFRSVSELPIMHQDWLNGKEFKCRVNSAAFPAPIEKTISKTKGRPKAPQVYTIPPPKEQMAKDKVSLTCMITDFFPEDITVEWQWNGQPAENYKNTQPIMDTDGSYFVYSKLNVQKSNWEAGNTFTCSVLHEGLHNHHTEKSLSHSPGK (SEQ ID NO: 20) |
| Heavy Chain -(D)-J Sequence | WGQGTLVTVSA (SEQ ID NO: 29) |
| Heavy CDR1 Kabat | DYYMN (SEQ ID NO: 1) |
| Heavy CDR2 Kabat | DINPNNGGTAYNQKFKG (SEQ ID NO: 2) |
| Heavy CDR3 Kabat | LAY |
| Heavy CDR 1 IMGT | GYTFTDYY (SEQ ID NO: 6) |
| Heavy CDR2 IMGT | INPNNGGT (SEQ ID NO: 7) |
| Heavy CDR3 IMGT | ALLAY (SEQ ID NO: 8) |
| Heavy CDR1 Chothia | GYTFTDY (SEQ ID NO: 11) |
| Heavy CDR2 Chothia | PNNG (SEQ ID NO: 12) |
| Heavy CDR3 Chothia | A |
| Heavy CDR1 Honegger | ASGYTFTDYY (SEQ ID NO: 15) |
| Heavy CDR2 Honegger | INPNNGGTAYNQKFKGK (SEQ ID NO: 16) |
| Heavy CDR3 Honegger | LA |
| Heavy Chain Variable Region without the -(D)-J Sequence | EVQLQQSGPELVKPGASVKISCQASGYTFTDYYMNWVKQSHGKRLEWIGDINPNNGGTAYNQKFKGKATLTVDRSSSTAYMEVRSLTSEDSAVYFCALLAY (SEQ ID NO: 21) |

TABLE 2-continued

Sequences for Additional Exemplary Anti-HBx Antibody Comprising the Variable Regions of HBx M19

| Antibody | Exemplary Variant of HBx M19 |
|---|---|
| Heavy Chain Variable Region | EVQLQQSGPELVKPGASVKISCQASGYTFTDYYMNWVKQSHGKRLE WIGDINPNNGGTAYNQKFKGKATLTVDRSSSTAYMEVRSLTSEDSA VYFCALLAYWGQGTLVTVSA (SEQ ID NO: 22) |
| Heavy Chain Constant Region | AKTTPPSVYPLAPGSAAQTNSMVTLGCLVKGYFPEPVTVTWNSGSL SSGVHTFPAVLQSDLYTLSSSVTVPSSTWPSETVTCNVAHPASSTK VDKKIVPRDCGCKPCICTVPEVSSVFIFPPKPKDVLTITLTPKVTC VVVDISKDDPEVQFSWFVDDVEVHTAQTQPREEQFNSTFRSVSELP IMHQDWLNGKEFKCRVNSAAFPAPIEKTISKTKGRPKAPQVYTIPP PKEQMAKDKVSLTCMITDFFPEDITVEWQWNGQPAENYKNTQPIMD TDGSYFVYSKLNVQKSNWEAGNTFTCSVLHEGLHNHHTEKSLSHSP GK (SEQ ID NO: 33) |
| Exemplary Heavy Chain Coding Sequence (underlined sequence corresponds to the signal peptide, which may be omitted or replaced with another signal peptide) | ACCCAAGCTGGCTAGCCGCCACCATGAA<u>ATGGGTCACCTTTATCAG CCTGCTGTTCCTGTTCAGCAGCGCC</u>TACTCTGAGGTCCAGCTGCAG CAATCTGGCCCCGAGCTTGTGAAACCTGGCGCCTCTGTGAAGATCA GCTGTCAGGCCAGCGGCTACACCTTCACCGACTACTACATGAACTG GGTTAAGCAGAGCCACGGCAAGCGGCTGGAATGGATCGGCGACATC AACCCCAACAATGGCGGCACCGCCTACAACCAGAAGTTCAAGGGCA AAGCCACACTGACCGTGGACAGAAGCAGCAGCACAGCCTACATGGA AGTGCGGAGCCTGACCAGCGAAGATAGCGCCGTGTACTTCTGTGCC CTGCTGGCCTATTGGGGCCAGGGAACACTGGTTACAGTGTCCGCTG CTAAAACGACACCCCCATCTGTCTATCCACTGGCCCCTGGATCTGC TGCCCAAACTAACTCCATGGTGACCCTGGGATGCCTGGTCAAGGGC TATTTCCCTGAGCCAGTGACAGTGACCTGGAACTCTGGATCCCTGT CCAGCGGTGTGCACACCTTCCCAGCTGTCCTGCAGTCTGACCTCTA CACTCTGAGCAGCTCAGTGACTGTCCCCTCCAGCACCTGGCCCAGC GAGACCGTCACCTGCAACGTTGCCCACCCGGCCAGCAGCACCAAGG TGGACAAGAAAATTGTGCCCAGGGATTGTGGTTGTAAGCCTTGCAT ATGTACAGTCCCAGAAGTATCATCTGTCTTCATCTTCCCCCCAAAG CCCAAGGATGTGCTCACCATTACTCTGACTCCTAAGGTCACGTGTG TTGTGGTAGACATCAGCAAGGATGATCCCGAGGTCCAGTTCAGCTG GTTTGTAGATGATGTGGAGGTGCACACAGCTCAGACGCAACCCCGG GAGGAGCAGTTCAACAGCACTTTCCGCTCAGTCAGTGAACTTCCCA TCATGCACCAGGACTGGCTCAATGGCAAGGAGTTCAAATGCAGGGT CAACAGTGCAGCTTTCCCTGCCCCCATCGAGAAAACCATCTCCAAA ACCAAAGGCAGACCGAAGGCTCCgCAGGIGTACACCATTCCACCTC CCAAGGAGCAGATGGCCAAGGATAAAGTCAGTCTGACCTGCATGAT AACAGACTTCTTCCCTGAAGACATTACTGTGGAGTGGCAGTGGAAT GGGCAGCCAGCGGAGAACTACAAGAACACTCAGCCCATCATGGACA CAGATGGCTCTTACTTCGTCTACAGCAAGCTCAATGTGCAGAAGAG CAACTGGGAGGCAGGAAATACTTTCACCTGCTCTGTGTTACATGAG GGCCTGCACAACCACCATACTGAGAAGAGCCTCTCCCACTCTCCTG GTAAATGA (SEQ ID NO: 57) |
| Light Chain | DVVMTQTPLSLPVSLGDQASISCRSSQSLVYSDGNTHLHWYLQKTG QSPKLLIYKASNRFSGVPDRFSGSGSGTDFTLKISRVEAEDLGVYF CSQSTHVPLTFGAGTKLELKRADAAPTVSIFPPSSEQLTSGGASVV CFLNNFYPKDINVKWKIDGSERQNGVLNSWTDQDSKDSTYSMSSTL TLTKDEYERHNSYTCEATHKTSTSPIVKSFNRNEC (SEQ ID NO: 60) |
| Light Chain -(D)-J Sequence | FGAGTKLELK (SEQ ID NO: 32) |
| Light CDR1 Kabat | RSSQSLVYSDGNTHLH (SEQ ID NO: 3) |
| Light CDR2 Kabat | KASNRFS (SEQ ID NO: 4) |
| Light CDR3 Kabat | SQSTHVPLT (SEQ ID NO: 5) |
| Light CDR1 IMGT | QSLVYSDGNTH (SEQ ID NO: 9) |
| Light CDR2 IMGT | KAS |
| Light CDR3 IMGT | SQSTHVPLT (SEQ ID NO: 10) |
| Light CDR1 Chothia | SQSLVYSDGNTH (SEQ ID NO: 13) |
| Light CDR2 Chothia | KAS |

TABLE 2-continued

Sequences for Additional Exemplary Anti-HBx Antibody Comprising the Variable Regions of HBx M19

| Antibody | Exemplary Variant of HBx M19 |
|---|---|
| Light CDR3 Chothia | STHVPL (SEQ ID NO: 14) |
| Light CDR1 Honegger | SSQSLVYSDGNTH (SEQ ID NO: 17) |
| Light CDR2 Honegger | KASNRFSGVPDR (SEQ ID NO: 18) |
| Light CDR3 Honegger | STHVPL (SEQ ID NO: 19) |
| Light Chain Variable Region without the -(D)-J Sequence | DVVMTQTPLSLPVSLGDQASISCRSSQSLVYSDGNTHLHWYLQKTG QSPKLLIYKASNRFSGVPDRFSGSGSGTDFTLKISRVEAEDLGVYF CSQSTHVPLT (SEQ ID NO: 23) |
| Light Chain Variable Region | DVVMTQTPLSLPVSLGDQASISCRSSQSLVYSDGNTHLHWYLQKTG QSPKLLIYKASNRFSGVPDRFSGSGSGTDFTLKISRVEAEDLGVYF CSQSTHVPLTFGAGTKLELK (SEQ ID NO: 24) |
| Light Chain Constant Region | RADAAPTVSIFPPSSEQLTSGGASVVCFLNNFYPKDINVKWKIDGS ERQNGVLNSWTDQDSKDSTYSMSSTLTLTKDEYERHNSYTCEATHK TSTSPIVKSFNRNEC (SEQ ID NO: 61) |
| Exemplary Light Chain Coding Sequence (underlined sequence corresponds to the signal peptide, which may be omitted or replaced with another signal peptide) | ACCCAAGCTGGCTAGCCGCCACCATGAA<u>ATGGGTCACCTTTATCAG CCTGCTGTTCCTGTTCAGCAGCGCCTACAGC</u>GACGTGGTCATGACA CAGACCCCACTGAGCCTGCCTGTGTCTCTGGGAGATCAGGCCAGCA TCAGCTGCAGATCTAGCCAGAGCCTGGTGTACTCCGACGGCAACAC ACATCTGCACTGGTATCTGCAGAAAACCGGACAGAGCCCCAAGCTG CTGATCTACAAGGCCAGCAACAGATTCAGCGGCGTGCCCGATAGAT TTTCCGGCAGCGGCTCTGGCACCGACTTCACCCTGAAGATCTCCAG AGTGGAAGCCGAGGACCTGGGCGTGTACTTCTGTAGCCAGTCTACC CACGTGCCACTGACCTTTGGCGCCGGAACAAAGCTGGAACTGAAGC GGGCAGATGCTGCACCAACTGTATCCATCTTCCCACCATCCAGTGA GCAGTTAACATCTGGAGGTGCCTCAGTCGTGTGCTTCTTGAACAAC TTCTACCCCAAAGACATCAATGTCAAGTGGAAGATTGATGGCAGTG AACGACAAAATGGCGTCCTGAACAGTTGGACTGATCAGGACAGCAA AGACAGCACCTACAGCATGAGCAGCACCCTCACGTTGACCAAGGAC GAGTATGAACGACATAACAGCTATACCTGTGAGGCCACTCACAAGA CATCACTTCACCCATTGTCAAGAGCTTCAACAGGAATGAGTGTTA GGAATTCTGCAGATATC (SEQ ID NO: 58) |

Non-limiting examples of leader peptides that may be present at the N-terminus of the heavy chain include MGWSWVFLFLLSGTAGVLS (SEQ ID NO: 28) and MKWVTFISLLFLFSSAYS (SEQ ID NO: 59). Non-limiting examples of leader peptides that may be present at the N-terminus of the light chain include MKLPVRLL-VLMFWIPASSS (SEQ ID NO: 31) and MKWVTFISLL-FLFSSAYS (SEQ ID NO: 59). In certain embodiments, such leader peptides are cleaved and not present in the final antibody.

Also included herein are chimeras including variable or CDR sequences of HBx M19, which is a mouse monoclonal antibody. The sequences of an exemplary antibody are provided in Table 3.

TABLE 3

Sequences for Exemplary Anti-HBx Chimera Including Variable Regions of HBx M19 and Rabbit Constant Regions

| Antibody | Chimera Including M19 Variable Regions and Rabbit Constant Regions |
|---|---|
| Heavy Chain | EVQLQQSGPELVKPGASVKISCQASGYTFTDYYMNWVKQSHGKRLE WIGDINPNNGGTAYNQKFKGKATLTVDRSSSTAYMEVRSLTSEDSA VYFCALLAYWGQGTLVTVSAGQPKAPSVFPLAPCCGDTPSSTVTLG CLVKGYLPEPVTVTWNSGTLTNGVRTFPSVRQSSGLYSLSSVVSVT SSSQPVTCNVAHPATNTKVDKTVAPSTCSKPTCPPPELLGGPSVFI FPPKPKDTLMISRTPEVTCVVVDVSQDDPEVQFTWYINNEQVRTAR PPLREQQFNSTIRVVSTLPIAHQDWLRGKEFKCKVHNKALPAPIEK TISKARGQPLEPKVYTMGPPREELSSRSVSLTCMINGFYPSDISVE WEKNGKAEDNYKTTPAVLDSDGSYFLYSKLSVPTSEWQRGDVFTCS VMHEALHNHYTQKSISRSPGK (SEQ ID NO: 34) |

TABLE 3-continued

Sequences for Exemplary Anti-HBx Chimera Including Variable Regions of HBx M19 and Rabbit Constant Regions

| Antibody | Chimera Including M19 Variable Regions and Rabbit Constant Regions |
| --- | --- |
| Heavy Chain -(D)-J Sequence | WGQGTLVTVSA (SEQ ID NO: 29) |
| Heavy CDR1 Kabat | DYYMN (SEQ ID NO: 1) |
| Heavy CDR2 Kabat | DINPNNGGTAYNQKFKG (SEQ ID NO: 2) |
| Heavy CDR3 Kabat | LAY |
| Heavy CDR 1 IMGT | GYTFTDYY (SEQ ID NO: 6) |
| Heavy CDR2 IMGT | INPNNGGT (SEQ ID NO: 7) |
| Heavy CDR3 IMGT | ALLAY (SEQ ID NO: 8) |
| Heavy CDR1 | GYTFTDY (SEQ ID NO: 11) |
| Heavy CDR2 Chothia | PNNG (SEQ ID NO: 12) |
| Heavy CDR3 Chothia | A |
| Heavy CDR1 Honegger | ASGYTFTDYY (SEQ ID NO: 15) |
| Heavy CDR2 Honegger | INPNNGGTAYNQKFKGK (SEQ ID NO: 16) |
| Heavy CDR3 Honegger | LA |
| Heavy Chain Variable Region without the -(D-)J Sequence | EVQLQQSGPELVKPGASVKISCQASGYTFTDYYMNWVKQSHGKRLE WIGDINPNNGGTAYNQKFKGKATLTVDRSSSTAYMEVRSLTSEDSA VYFCALLAY (SEQ ID NO: 21) |
| Heavy Chain Variable Region | EVQLQQSGPELVKPGASVKISCQASGYTFTDYYMNWVKQSHGKRLE WIGDINPNNGGTAYNQKFKGKATLTVDRSSSTAYMEVRSLTSEDSA VYFCALLAYWGQGTLVTVSA (SEQ ID NO: 22) |
| Heavy Chain Constant Region | GQPKAPSVFPLAPCCGDTPSSTVTLGCLVKGYLPEPVTVTWNSGTL TNGVRTFPSVRQSSGLYSLSSVVSVTSSSQPVTCNVAHPATNTKVD KTVAPSTCSKPTCPPPELLGGPSVFIFPPKPKDTLMISRTPEVTCV VVDVSQDDPEVQFTWYINNEQVRTARPPLREQQFNSTIRVVSTLPI AHQDWLRGKEFKCKVHNKALPAPIEKTISKARGQPLEPKVYTMGPP REELSSRSVSLTCMINGFYPSDISVEWEKNGKAEDNYKTTPAVLDS DGSYFLYSKLSVPTSEWQRGDVFTCSVMHEALHNHYTQKSISRSPG K (SEQ ID NO: 35) |
| Exemplary Heavy Chain Coding Sequence (underlined sequence corresponds to the signal peptide, which may be omitted or replaced with another signal peptide) | ACCCAAGCTGGCTAGCCGCCACCATGAAATGGGTCACCTTTATCAG CCTGCTGTTCCTGTTCAGCAGCGCCTACTCTGAGGTCCAGCTGCAG CAATCTGGCCCCGAGCTTGTGAAACCTGGCGCCTCTGTGAAGATCA GCTGTCAGGCCAGCGGCTACACCTTCACCGACTACTACATGAACTG GGTTAAGCAGAGCCACGGCAAGCGGCTGGAATGGATCGGCGACATC AACCCCAACAATGGCGGCACCGCCTACAACCAGAAGTTCAAGGGCA AAGCCACACTGACCGTGGACAGAAGCAGCAGCACAGCCTACATGGA AGTGCGGAGCCTGACCAGCGAAGATAGCGCCGTGTACTTCTGTGCC CTGCTGGCCTATTGGGGCCAGGGAACACTGGTTACAGTGTCCGCTG GCAACCTAAGGCTCCATCAGTCTTCCCACTGGCACCATGCTGCGG TGACACACCTAGCTCCACGGTGACCCTGGGATGCCTGGTCAAAGGC TACCTCCCAGAGCCAGTGACCGTGACCTGGAACTCGGGTACACTCA CCAATGGTGTACGCACCTTCCCATCCGTCCGGCAGTCCTCAGGACT CTACTCGCTGTCGAGCGTTGTGAGCGTGACCTCAAGCAGCCAGCCT GTCACCTGCAACGTGGCTCACCCAGCTACTAACACCAAAGTGGACA AGACCGTTGCACCATCGACATGCAGCAAGCCTACGTGCCCACCTCC TGAACTCCTGGGTGGACCGTCTGTCTTCATCTTCCCTCCAAAACCT AAGGACACCCTCATGATCTCACGCACACCTGAGGTCACATGCGTTG TTGTGGACGTGAGCCAGGATGACCCAGAGGTGCAGTTCACATGGTA CATAAACAACGAGCAGGTTCGCACAGCTCGGCCTCCTCTACGAGAG CAACAGTTCAACAGCACGATCCGCGTGGTCAGCACACTCCCTATCG |

TABLE 3-continued

Sequences for Exemplary Anti-HBx Chimera Including Variable
Regions of HBx M19 and Rabbit Constant Regions

| Antibody | Chimera Including M19 Variable Regions and Rabbit Constant Regions |
|---|---|
| | CGCACCAGGACTGGCTGAGGGGTAAGGAGTTCAAGTGCAAAGTCCA<br>CAACAAGGCACTCCCTGCTCCTATCGAGAAAACCATCTCCAAAGCC<br>AGAGGTCAGCCTCTGGAGCCGAAGGTCTACACCATGGGACCTCCAC<br>GGGAGGAGCTGAGCAGCAGGTCGGTCAGCCTGACCTGCATGATCAA<br>CGGATTCTACCCTTCCGACATCTCGGTGGAGTGGGAGAAGAACGGT<br>AAGGCAGAGGACAACTACAAGACCACGCCTGCCGTGCTGGACAGCG<br>ACGGTTCCTACTTCCTCTACAGCAAGCTCTCAGTGCCTACGAGTGA<br>GTGGCAGCGGGGTGACGTCTTCACCTGCTCCGTGATGCACGAGGCC<br>TTGCACAACCACTACACGCAGAAGTCCATCTCCCGCTCTCCGGGTA<br>AGTAGGAATTCTGCAGATATCA (SEQ ID NO: 39) |
| Light Chain | DVVMTQTPLSLPVSLGDQASISCRSSQSLVYSDGNTHLHWYLQKTG<br>QSPKLLIYKASNRFSGVPDRFSGSGSGTDFTLKISRVEAEDLGVYF<br>CSQSTHVPLTFGAGTKLELKGDPVAPTVLIFPPAADQVATGTVTIV<br>CVANKYFPDVTVTWEVDGTTQTTGIENSKTPQNSADSTYNLSSTLT<br>LTSTQYNSHKEYTCKVTQGTTSVVQSFNRGDC (SEQ ID NO: 36) |
| Light Chain -(D)-J Sequence | FGAGTKLELK (SEQ ID NO: 32) |
| Light CDR1 Kabat | RSSQSLVYSDGNTHLH (SEQ ID NO: 3) |
| Light CDR2 Kabat | KASNRFS (SEQ ID NO: 4) |
| Light CDR3 Kabat | SQSTHVPLT (SEQ ID NO: 5) |
| Light CDR1 IMGT | QSLVYSDGNTH ( SEQ ID NO: 9) |
| Light CDR2 IMGT | KAS |
| Light CDR3 IMGT | SQSTHVPLT (SEQ ID NO: 10) |
| Light CDR1 Chothia | SQSLVYSDGNTH (SEQ ID NO: 13) |
| Light CDR2 Chothia | KAS |
| Light CDR3 Chothia | STHVPL (SEQ ID NO: 14) |
| Light CDR1 Honegger | SSQSLVYSDGNTH (SEQ ID NO: 17) |
| Light CDR2 Honegger | KASNRFSGVPDR (SEQ ID NO: 18) |
| Light CDR3 Honegger | STHVPL (SEQ ID NO: 19) |
| Light Chain Variable Region without the -(D)-J Sequence | DVVMTQTPLSLPVSLGDQASISCRSSQSLVYSDGNTHLHWYLQKTG<br>QSPKLLIYKASNRFSGVPDRFSGSGSGTDFTLKISRVEAEDLGVYF<br>CSQSTHVPLT (SEQ ID NO: 23) |
| Light Chain Variable Region | DVVMTQTPLSLPVSLGDQASISCRSSQSLVYSDGNTHLHWYLQKTG<br>QSPKLLIYKASNRFSGVPDRFSGSGSGTDFTLKISRVEAEDLGVYF<br>CSQSTHVPLTFGAGTKLELK (SEQ ID NO: 24) |
| Light Chain Constant Region | GDPVAPTVLIFPPAADQVATGTVTIVCVANKYFPDVTVTWEVDGTT<br>QTTGIENSKTPQNSADSTYNLSSTLTLTSTQYNSHKEYTCKVTQGT<br>TSVVQSFNRGDC (SEQ ID NO: 37) |
| Exemplary Light Chain Coding Sequence (underlined sequence corresponds to the signal peptide, which may be omitted or replaced | ACCCAAGCTGGCTAGCCGCCACCATG<u>AATGGGTCACCTTTATCAG</u><br><u>CCTGCTGTTCCTGTTCAGCAGCGCCTACAGC</u>GACGTGGTCATGACA<br>CAGACCCCACTGAGCCTGCCTGTGTCTCTGGGAGATCAGGCCAGCA<br>TCAGCTGCAGATCTAGCCAGAGCCTGGTGTACTCCGACGGCAACAC<br>ACATCTGCACTGGTATCTGCAGAAAACCGGACAGAGCCCCAAGCTG<br>CTGATCTACAAGGCCAGCAACAGATTCAGCGGCGTGCCCGATAGAT<br>TTTCCGGCAGCGGCTCTGGCACCGACTTCACCCTGAAGATCTCCAG<br>AGTGGAAGCCGAGGACCTGGGCGTGTACTTCTGTAGCCAGTCTACC<br>CACGTGCCACTGACCTTTGGCGCCGGAACAAAGCTGGAACTGAAGG |

TABLE 3-continued

Sequences for Exemplary Anti-HBx Chimera Including Variable Regions of HBx M19 and Rabbit Constant Regions

| Antibody | Chimera Including M19 Variable Regions and Rabbit Constant Regions |
|---|---|
| with another signal peptide) | GTGATCCAGTTGCACCTACTGTCCTCATCTTCCCACCAGCTGCTGA TCAGGTGGCAACTGGAACAGTCACCATCGTGTGTGTGGCGAATAAA TACTTTCCCGATGTCACCGTCACCTGGGAGGTGGATGGCACCACCC AAACAACTGGCATCGAGAACAGTAAAACACCGCAGAACTCTGCAGA TICTACCTACAACCTCAGCAGCACTCTGACACTGACCAGCACACAG TACAACAGCCACAAAGAGTACACCTGCAAGGTGACCCAGGGCACGA CCTCAGTCGTCCAGAGCTTCAACAGGGGTGACTGCTAG (SEQ ID NO: 56) |

Non-limiting examples of leader peptides that may be present at the N-terminus of the heavy chain include MGWSWVFLFLLSGTAGVLS (SEQ ID NO: 28) and MKWVTFSLLFLFSSAYS (SEQ ID NO: 59). Non-limiting examples of leader peptides that may be present at the N-terminus of the light chain include MIKLPVRLL-VLMFWPASSS (SEQ ID NO: 31) and MKWVTFISLL-FLFSSAYS (SEQ ID NO: 59). In certain embodiments, such leader peptides are cleaved and not present in the final antibody.

TABLE 4

Anti-HBx antibody M19 CDR regions according to various numbering definitions

| LIGHT1 CDR1 KARAT | LIGHT1 CDR2 KARAT | LIGHT1 CDR3 KARAT |
|---|---|---|
| RSSQSLVYSDGNTHLH (SEQ ID NO: 3) | KASNRFS (SEQ ID NO: 4) | SQSTHVPLT (SEQ ID NO: 5) |
| LIGHT1 CDR1 IMGT | LIGHT1 CDR2 IMGT | LIGHT1 CDR3 IMGT |
| QSLVYSDGNTH (SEQ ID NO: 9) | KAS | SQSTHVPLT (SEQ ID NO: 10) |
| LIGHT1 CDR1 CHOTHIA | LIGHT1 CDR2 CHOTHIA | LIGHT1 CDR3 CHOTHIA |
| SQSLVYSDGNTH (SEQ ID NO: 13) | KAS | STHVPL (SEQ ID NO: 14) |
| LIGHT1 CDR1 HONEGGER | LIGHT1 CDR2 HONEGGER | LIGHT1 CDR3 HONEGGER |
| SSQSLVYSDGNTH (SEQ ID NO: 17) | KASNRFSGVPDR (SEQ ID NO: 18) | STHVPL (SEQ ID NO: 19) |
| HEAVY1 CDR1 KABAT | HEAVY1 CDR2 KABAT | HEAVY1 CDR3 KABAT |
| DYYMN (SEQ ID NO: 1) | DINPNNGGTAYNQKFKG (SEQ ID NO: 2) | LAY |
| HEAVY1 CDR1 IMGT | HEAVY1 CDR2 IMGT | HEAVY1 CDR3 IMGT |
| GYTFTDYY (SEQ ID NO: 6) | INPNNGGT (SEQ ID NO: 7) | ALLAY (SEQ ID NO: 8) |
| HEAVY1 CDR1 CHOTHIA | HEAVY1 CDR2 CHOTHIA | HEAVY1 CDR3 CHOTHIA |
| GYTFTDY (SEQ ID NO: 11) | PNNG (SEQ ID NO: 12) | A |
| HEAVY1 CDR1 HONEGGER | HEAVY1 CDR2 HONEGGER | HEAVY1 CDR3 HONEGGER |
| ASGYTFTDYY (SEQ ID NO: 15) | INPNNGGTAYNQKFKGK (SEQ ID NO: 16) | LA |

TABLE 5

Exemplary IgG Heavy Chain Constant Region Sequences

| Species and Antibody Heavy Constant Chain Domain | Sequence |
|---|---|
| Mouse IgG | AKTTPPSVYPLAPGSAAQTNSMVTLGCLVKGYFPEPVTVTWNSGSL<br>SSGVHTFPAVLQSDLYTLSSSVTVPSSTWPSQTVTCNVAHPASSTK<br>VDKKIVPRDCGCKPCICTVPEVSSVFIFPPKPKDVLTITLTPKVTC<br>VVVDISKDDPEVQFSWFVDDVEVHTAQTKPREEQINSTFRSVSELP<br>IMHQDWLNGKEFKCRVNSAAFPAPIEKTISKTKGRPKAPQVYTIPP<br>PKEQMAKDKVSLTCMITNFFPEDITVEWQWNGQPAENYKNTQPIMD<br>TDGSYFVYSKLNVQKSNWEAGNTFTCSVLHEGLHNHHTEKSLSHSP<br>GK (SEQ ID NO: 25) |
| Rabbit IgG | GQPKAPSVFPLAPCCGDTPSSTVTLGCLVKGYLPEPVTVTWNSGTL<br>TNGVRTFPSVRQSSGLYSLSSVVSVTSSSQPVTCNVAHPATNTKVD<br>KTVAPSTCSKPTCPPPELLGGPSVFIFPPKPKDTLMISRTPEVTCV<br>VVDVSQDDPEVQFTWYINNEQVRTARPPLREQQFNSTIRVVSTLPI<br>THQDWLRGKEFKCKVHNKALPAPIEKTISKARGQPLEPKVYTMGPP<br>REELSSRSVSLTCMINGFYPSDISVEWEKNGKAEDNYKTTPAVLDS<br>DGSYFLYNKLSVPTSEWQRGDVFTCSVMHEALHNHYTQKSISRSPG<br>K (SEQ ID NO: 64) |
| Human IgG | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKKVEPKSCDKTHTCPPCPAPELLGGPSVFLFPPKPKDTLMISR<br>TPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQ<br>VYTLPPSRDELTKNQVSLTCLVKGFYPSDIAVEWESNGQPENNYKT<br>TPPVLDSDGSFFLYSKLTVDKSRWQQGNVFSCSVMHEALHNHYTQK<br>SLSLSPGK (SEQ ID NO: 65) |
| Rat IgG | AETTAPSVYPLAPGTALKSNSMVTLGCLVKGYFPEPVTVTWNSGAL<br>SSGVHTFPAVLQSGLYTLTSSVTVPSSTWSSQAVTCNVAHPASSTK<br>VDKKIVPRECNPCGCTGSEVSSVFIFPPKTKDVLTITLTPKVTCVV<br>VDISQNDPEVRFSWFIDDVEVHTAQTHAPEKQSNSTLRSVSELPIV<br>HRDWLNGKTFKCKVNSGAFPAPIEKSISKPEGTPRGPQVYTMAPPK<br>EEMTQSQVSITCMVKGFYPPDIYTEWKMNGQPQENYKNTPPTMDTD<br>GSYFLYSKLNVKKETWQQGNTFTCSVLHEGLHNHHTEKSLSHSPGK<br>(SEQ ID NO: 38) |

IV. Polynucleotides, Vectors, and Cells

This disclosure also features polynucleotides including a nucleotide sequence encoding an antibody, antigen-binding antibody fragment, chain, or binding domain described herein, vectors including such polynucleotides, and host cells (e.g., mammalian cells, insect cells, plant cells, yeast, E. coli) including such polynucleotides or expression vectors. Provided herein are polynucleotides including nucleotide sequences encoding any of the antibodies provided herein, as well as vectors including such polynucleotide sequences, e.g., expression vectors for their efficient expression in host cells, e.g., mammalian cells.

In an aspect, included herein are polynucleotides including nucleotide sequences encoding the VH, VL, or VH and VL of the antibodies disclosed herein.

In an aspect, provided herein are polynucleotides including nucleotide sequences encoding antibodies, which bind to HBx polypeptides and include an amino acid sequence as described herein.

In an aspect, included herein are polynucleotides including nucleotide sequences encoding antigen-binding antibody fragments, chains, or domains, which bind to HBx polypeptides and includes an amino acid sequence as described herein.

In an aspect, provided herein are polynucleotides including a nucleotide sequence encoding the CDRs, light chain, or heavy chain of an antibody described herein. In certain embodiments, the polynucleotides can include nucleotide sequences encoding a light chain or light chain variable domain including the VL CDRs of antibodies described herein (see, e.g., Table 1). The polynucleotides can include nucleotide sequences encoding a heavy chain or heavy chain variable domain including the VH CDRs of antibodies described herein (see, e.g., Table 1 above). In certain embodiments, a polynucleotide described herein encodes a variable light chain or light chain with the VL-CDRs including amino acid sequences set forth in Table 1. In another embodiment, a polynucleotide described herein encodes a variable heavy chain or heavy chain with VH-CDRs including amino acid sequences set forth in Table 1. In one embodiment, a polynucleotide described herein encodes a VL region including the amino acid sequence set forth in SEQ ID NO: 23 or 24. In another embodiment, a polynucleotide described herein encodes a VH region including the amino acid sequence set forth in SEQ ID NO: 21 or 22. In yet another embodiment, a polynucleotide described herein encodes a light chain including the amino acid sequence set forth in SEQ ID NO: 30. In another embodiment, a polynucleotide described herein encodes a heavy chain including the amino acid sequence set forth in SEQ ID NO: 27.

Also provided by this disclosure are polynucleotides encoding an antibody, or a chain or a fragment thereof that are optimized, e.g., by codon optimization, replacement with heterologous signal sequences, and elimination of mRNA instability elements. Methods to generate optimized nucleic acids can be carried out by adapting the methods described in, e.g., U.S. Pat. Nos. 5,965,726; 6,174,666; 6,291,664; 6,414,132; and 6,794,498.

In an aspect, provided herein is an isolated polynucleotide encoding the antibody or antigen-binding antibody fragment as described herein, or a heavy chain or light chain of the antibody, or an antigen-binding domain of the antibody. In certain embodiments, an isolated polynucleotide encoding a heavy chain of an antibody as described herein is provided. In certain embodiments, an isolated polynucleotide encoding a light chain of an antibody as described herein is provided.

Also included are polynucleotides that encode polypeptide variants of the antibody and antigen-binding antibody fragments thereof disclosed herein, as well as polynucleotide variants of polynucleotides encoding an antibody or antigen-binding antibody fragment thereof of the present disclosure, such as, e.g., intact antibodies, scFvs, heavy chains, light chains, VH regions, and VL regions. In certain embodiments, the present disclosure includes a polynucleotide variant having at least 70%, at least 75%, at least 80%, at least 85%, at least 90%, at least 95%, at least 98%, or at least 99% homology with a polynucleotide described herein. In certain embodiments, the polynucleotide includes the nucleotide sequence set forth as SEQ ID NO: 39, 56, 57, or 58, or a variant thereof.

In certain embodiments of the polynucleotides, they (or parts or subregions thereof) may be codon optimized. Codon optimization methods are known in the art and may be used, e.g., to match codon frequencies in target and host organisms, to ensure proper folding, bias GC content to increase mRNA stability or reduce secondary structures, minimize tandem repeat codons or base runs that may impair gene construction or expression, customize transcriptional and translational control regions, insert or remove protein trafficking sequences, modify ribosome binding sites and mRNA degradation sites, to adjust translational rates to allow the various domains of the protein to fold properly, or to reduce or eliminate problem secondary structures within the polynucleotide. Codon optimization tools, algorithms and services are known in the art, non-limiting examples include services from GeneArt (Life Technologies), DNA2.0 (Menlo Park Calif.) and/or proprietary methods. In one embodiment, the nucleic acid sequence is optimized using optimization algorithms. Examples of codon options for each amino acid are given in Table 6.

TABLE 6

Codon Options

| Amino Acid | Single Letter Code | Codon Options |
|---|---|---|
| Isoleucine | I | ATT, ATC, ATA |
| Leucine | L | CTT, CTC, CTA, CTG, TTA, TTG |
| Valine | V | GTT, GTC, GTA, GTG |
| Phenylalanine | F | TTT, TTC |
| Methionine | M | ATG |
| Cysteine | C | TGT, TGC |
| Alanine | A | GCT, GCC, GCA, GCG |
| Glycine | G | GGT, GGC, GGA, GGG |
| Proline | P | CCT, CCC, CCA, CCG |
| Threonine | T | ACT, ACC, ACA, ACG |
| Serine | S | TCT, TCC, TCA, TCG, AGT, AGC |
| Tyrosine | Y | TAT, TAC |
| Tryptophan | W | TGG |
| Glutamine | Q | CAA, CAG |
| Asparagine | N | AAT, AAC |
| Histidine | H | CAT, CAC |
| Glutamic acid | E | GAA, GAG |
| Aspartic acid | D | GAT, GAC |
| Lysine | K | AAA, AAG |
| Arginine | R | CGT, CGC, CGA, CGG, AGA, AGG |

TABLE 6-continued

Codon Options

| Amino Acid | Single Letter Code | Codon Options |
|---|---|---|
| Selenocysteine | Sec | UGA in mRNA in presence of Selenocystein insertion element (SECIS) |
| Stop codons | Stop | TAA, TAG, TGA |

This disclosure also provides vectors including a nucleic acid(s) disclosed herein. A vector can be of any type, for example, a recombinant vector such as an expression vector. Vectors include, but are not limited to, plasmids, cosmids, bacterial artificial chromosomes (BAC) and yeast artificial chromosomes (YAC) and vectors derived from bacteriophages or plant or animal (including human) viruses. In certain embodiments, the vector is a viral vector. In certain embodiments, the vector is anon-viral vector such as a plasmid. In certain embodiments, vectors can include an origin of replication recognized by the proposed host cell and in the case of expression vectors, promoter and other regulatory regions recognized by the host cell. In certain embodiments, a vector includes a polynucleotide encoding an antibody of the disclosure, or a chain or fragment thereof, operably linked to a promoter and optionally additional regulatory elements. Certain vectors are capable of autonomous replication in a host into which they are introduced (e.g., vectors having a bacterial origin of replication can replicate in bacteria). Other vectors can be integrated into the genome of a host upon introduction into the host, and thereby are replicated along with the host genome. Vectors include, but are not limited to, those suitable for recombinant production of the antibodies disclosed herein. In certain embodiments, a vector is combined with a cationic condensing agent such as, but not limited to, lipofectamine, polyethyleneimine, a dendrimer, chitosan, or poly-l-lysine to increase its delivery into cells.

The choice of the vector is dependent on the recombinant procedures followed and the host used. Introduction of vectors into host cells can be effected by inter alia calcium phosphate transfection, virus infection, DEAE-dextran-mediated transfection, lipofectamine transfection, or electroporation. Vectors may be autonomously replicating or may replicate together with the chromosome into which they have been integrated. In certain embodiments, the vectors contain one or more selection markers. The choice of the markers may depend on the host cells of choice. These include, but are not limited to, kanamycin, neomycin, puromycin, hygromycin, zeocin, thymidine kinase gene from Herpes simplex virus (HSV-TK), and dihydrofolate reductase gene from mouse (dhfr). Vectors including one or more nucleic acid molecules encoding the antibodies described herein, operably linked to one or more nucleic acid molecules encoding proteins or peptides that can be used to isolate the antibodies, are also covered by the present disclosure. These proteins or peptides include, but are not limited to, glutathione-S-transferase, maltose binding protein, metal-binding polyhistidine, green fluorescent protein, luciferase and beta-galactosidase.

In certain embodiments, the vector that is used is pcDNA™3.1+ (ThermoFisher, MA).

In particular embodiments, the vector is pcDNA™3.1+ (ThermoFisher, MA), which has the following sequence:

```
GACGGATCGGGAGATCTCCCGATCCCCTATGGTGCACTCTCAGTACAATCTGCTCTGATGCC

GCATAGTTAAGCCAGTATCTGCTCCCTGCTTGTGTGTTGGAGGTCGCTGAGTAGTGCGCGAG

CAAAATTTAAGCTACAACAAGGCAAGGCTTGACCGACAATTGCATGAAGAATCTGCTTAGGG

TTAGGCGTTTTGCGCTGCTTCGCGATGTACGGGCCAGATATACGCGTTGACATTGATTATTG

ACTAGTTATTAATAGTAATCAATTACGGGGTCATTAGTTCATAGCCCATATATGGAGTTCCG

CGTTACATAACTTACGGTAAATGGCCCGCCTGGCTGACCGCCCAACGACCCCCGCCCATTGA

CGTCAATAATGACGTATGTTCCCATAGTAACGCCAATAGGGACTTTCCATTGACGTCAATGG

GTGGAGTATTTACGGTAAACTGCCCACTTGGCAGTACATCAAGTGTATCATATGCCAAGTAC

GCCCCCTATTGACGTCAATGACGGTAAATGGCCCGCCTGGCATTATGCCCAGTACATGACCT

TATGGGACTTTCCTACTTGGCAGTACATCTACGTATTAGTCATCGCTATTACCATGGTGATG

CGGTTTTGGCAGTACATCAATGGGCGTGGATAGCGGTTTGACTCACGGGGATTTCCAAGTCT

CCACCCCATTGACGTCAATGGGAGTTTGTTTTGGCACCAAAATCAACGGGACTTTCCAAAAT

GTCGTAACAACTCCGCCCCATTGACGCAAATGGGCGGTAGGCGTGTACGGTGGGAGGTCTAT

ATAAGCAGAGCTCTCTGGCTAACTAGAGAACCCACTGCTTACTGGCTTATCGAAATTAATAC

GACTCACTATAGGGAGACCCAAGCTGGCTAGCGTTTAAACTTAAGCTTGGTACCGAGCTCGG

ATCCACTAGTCCAGTGTGGTGGAATTCTGCAGATATCCAGCACAGTGGCGGCCGCTCGAGTC

TAGAGGGCCCGTTTAAACCCGCTGATCAGCCTCGACTGTGCCTTCTAGTTGCCAGCCATCTG

TTGTTTGCCCCTCCCCCGTGCCTTCCTTGACCCTGGAAGGTGCCACTCCCACTGTCCTTTCC

TAATAAAATGAGGAAATTGCATCGCATTGTCTGAGTAGGTGTCATTCTATTCTGGGGGGTGG

GGTGGGGCAGGACAGCAAGGGGGAGGATTGGGAAGACAATAGCAGGCATGCTGGGGATGCGG

TGGGCTCTATGGCTTCTGAGGCGGAAAGAACCAGCTGGGGCTCTAGGGGGTATCCCCACGCG

CCCTGTAGCGGCGCATTAAGCGCGGCGGGTGTGGTGGTTACGCGCAGCGTGACCGCTACACT

TGCCAGCGCCCTAGCGCCCGCTCCTTTCGCTTTCTTCCCTTCCTTTCTCGCCACGTTCGCCG

GCTTTCCCCGTCAAGCTCTAAATCGGGGGCTCCCTTTAGGGTTCCGATTTAGTGCTTTACGG

CACCTCGACCCCAAAAAACTTGATTAGGGTGATGGTTCACGTAGTGGGCCATCGCCCTGATA

GACGGTTTTTCGCCCTTTGACGTTGGAGTCCACGTTCTTTAATAGTGGACTCTTGTTCCAAA

CTGGAACAACACTCAACCCTATCTCGGTCTATTCTTTTGATTTATAAGGGATTTTGCCGATT

TCGGCCTATTGGTTAAAAAATGAGCTGATTTAACAAAAATTTAACGCGAATTAATTCTGTGG

AATGTGTGTCAGTTAGGGTGTGGAAAGTCCCCAGGCTCCCCAGCAGGCAGAAGTATGCAAAG

CATGCATCTCAATTAGTCAGCAACCAGGTGTGGAAAGTCCCCAGGCTCCCCAGCAGGCAGAA

GTATGCAAAGCATGCATCTCAATTAGTCAGCAACCATAGTCCCGCCCCTAACTCCGCCCATC

CCGCCCCTAACTCCGCCCAGTTCCGCCCATTCTCCGCCCCATGGCTGACTAATTTTTTTTAT

TTATGCAGAGGCCGAGGCCGCCTCTGCCTCTGAGCTATTCCAGAAGTAGTGAGGAGGCTTTT

TTGGAGGCCTAGGCTTTTGCAAAAAGCTCCCGGGAGCTTGTATATCCATTTTCGGATCTGAT

CAAGAGACAGGATGAGGATCGTTTCGCATGATTGAACAAGATGGATTGCACGCAGGTTCTCC

GGCCGCTTGGGTGGAGAGGCTATTCGGCTATGACTGGGCACAACAGACAATCGGCTGCTCTG

ATGCCGCCGTGTTCCGGCTGTCAGCGCAGGGGCGCCCGGTTCTTTTTGTCAAGACCGACCTG

TCCGGTGCCCTGAATGAACTGCAGGACGAGGCAGCGCGGCTATCGTGGCTGGCCACGACGGG

CGTTCCTTGCGCAGCTGTGCTCGACGTTGTCACTGAAGCGGGAAGGGACTGGCTGCTATTGG

GCGAAGTGCCGGGGCAGGATCTCCTGTCATCTCACCTTGCTCCTGCCGAGAAAGTATCCATC

ATGGCTGATGCAATGCGGCGGCTGCATACGCTTGATCCGGCTACCTGCCCATTCGACCACCA
```

-continued

```
AGCGAAACATCGCATCGAGCGAGCACGTACTCGGATGGAAGCCGGTCTTGTCGATCAGGATG

ATCTGGACGAAGAGCATCAGGGGCTCGCGCCAGCCGAACTGTTCGCCAGGCTCAAGGCGCGC

ATGCCCGACGGCGAGGATCTCGTCGTGACCCATGGCGATGCCTGCTTGCCGAATATCATGGT

GGAAAATGGCCGCTTTTCTGGATTCATCGACTGTGGCCGGCTGGGTGTGGCGGACCGCTATC

AGGACATAGCGTTGGCTACCCGTGATATTGCTGAAGAGCTTGGCGGCGAATGGGCTGACCGC

TTCCTCGTGCTTTACGGTATCGCCGCTCCCGATTCGCAGCGCATCGCCTTCTATCGCCTTCT

TGACGAGTTCTTCTGAGCGGGACTCTGGGGTTCGAAATGACCGACCAAGCGACGCCCAACCT

GCCATCACGAGATTTCGATTCCACCGCCGCCTTCTATGAAAGGTTGGGCTTCGGAATCGTTT

TCCGGGACGCCGGCTGGATGATCCTCCAGCGCGGGATCTCATGCTGGAGTTCTTCGCCCAC

CCCAACTTGTTTATTGCAGCTTATAATGGTTACAAATAAAGCAATAGCATCACAAATTTCAC

AAATAAAGCATTTTTTTCACTGCATTCTAGTTGTGGTTTGTCCAAACTCATCAATGTATCTT

ATCATGTCTGTATACCGTCGACCTCTAGCTAGAGCTTGGCGTAATCATGGTCATAGCTGTTT

CCTGTGTGAAATTGTTATCCGCTCACAATTCCACACAACATACGAGCCGGAAGCATAAAGTG

TAAAGCCTGGGGTGCCTAATGAGTGAGCTAACTCACATTAATTGCGTTGCGCTCACTGCCCG

CTTTCCAGTCGGGAAACCTGTCGTGCCAGCTGCATTAATGAATCGGCCAACGCGCGGGGAGA

GGCGGTTTGCGTATTGGGCGCTCTTCCGCTTCCTCGCTCACTGACTCGCTGCGCTCGGTCGT

TCGGCTGCGGCGAGCGGTATCAGCTCACTCAAAGGCGGTAATACGGTTATCCACAGAATCAG

GGGATAACGCAGGAAAGAACATGTGAGCAAAAGGCCAGCAAAAGGCCAGGAACCGTAAAAAG

GCCGCGTTGCTGGCGTTTTTCCATAGGCTCCGCCCCCCTGACGAGCATCACAAAAATCGACG

CTCAAGTCAGAGGTGGCGAAACCCGACAGGACTATAAAGATACCAGGCGTTTCCCCCTGGAA

GCTCCCTCGTGCGCTCTCCTGTTCCGACCCTGCCGCTTACCGGATACCTGTCCGCCTTTCTC

CCTTCGGGAAGCGTGGCGCTTTCTCATAGCTCACGCTGTAGGTATCTCAGTTCGGTGTAGGT

CGTTCGCTCCAAGCTGGGCTGTGTGCACGAACCCCCCGTTCAGCCCGACCGCTGCGCCTTAT

CCGGTAACTATCGTCTTGAGTCCAACCCGGTAAGACACGACTTATCGCCACTGGCAGCAGCC

ACTGGTAACAGGATTAGCAGAGCGAGGTATGTAGGCGGTGCTACAGAGTTCTTGAAGTGGTG

GCCTAACTACGGCTACACTAGAAGAACAGTATTTGGTATCTGCGCTCTGCTGAAGCCAGTTA

CCTTCGGAAAAAGAGTTGGTAGCTCTTGATCCGGCAAACAAACCACCGCTGGTAGCGGTTTT

TTTGTTTGCAAGCAGCAGATTACGCGCAGAAAAAAAGGATCTCAAGAAGATCCTTTGATCTT

TTCTACGGGGTCTGACGCTCAGTGGAACGAAAACTCACGTTAAGGGATTTTGGTCATGAGAT

TATCAAAAAGGATCTTCACCTAGATCCTTTTAAATTAAAAATGAAGTTTTAAATCAATCTAA

AGTATATATGAGTAAACTTGGTCTGACAGTTACCAATGCTTAATCAGTGAGGCACCTATCTC

AGCGATCTGTCTATTTCGTTCATCCATAGTTGCCTGACTCCCCGTCGTGTAGATAACTACGA

TACGGGAGGGCTTACCATCTGGCCCCAGTGCTGCAATGATACCGCGAGACCCACGCTCACCG

GCTCCAGATTTATCAGCAATAAACCAGCCAGCCGGAAGGGCCGAGCGCAGAAGTGGTCCTGC

AACTTTATCCGCCTCCATCCAGTCTATTAATTGTTGCCGGGAAGCTAGAGTAAGTAGTTCGC

CAGTTAATAGTTTGCGCAACGTTGTTGCCATTGCTACAGGCATCGTGGTGTCACGCTCGTCG

TTTGGTATGGCTTCATTCAGCTCCGGTTCCCAACGATCAAGGCGAGTTACATGATCCCCCAT

GTTGTGCAAAAAAGCGGTTAGCTCCTTCGGTCCTCCGATCGTTGTCAGAAGTAAGTTGGCCG

CAGTGTTATCACTCATGGTTATGGCAGCACTGCATAATTCTCTTACTGTCATGCCATCCGTA

AGATGCTTTTCTGTGACTGGTGAGTACTCAACCAAGTCATTCTGAGAATAGTGTATGCGGCG
```

-continued

```
ACCGAGTTGCTCTTGCCCGGCGTCAATACGGGATAATACCGCGCCACATAGCAGAACTTTAA

AAGTGCTCATCATTGGAAAACGTTCTTCGGGGCGAAAACTCTCAAGGATCTTACCGCTGTTG

AGATCCAGTTCGATGTAACCCACTCGTGCACCCAACTGATCTTCAGCATCTTTTACTTTCAC

CAGCGTTTCTGGGTGAGCAAAAACAGGAAGGCAAAATGCCGCAAAAAAGGGAATAAGGGCGA

CACGGAAATGTTGAATACTCATACTCTTCCTTTTTCAATATTATTGAAGCATTTATCAGGGT

TATTGTCTCATGAGCGGATACATATTTGAATGTATTTAGAAAAATAAACAAATAGGGGTTCC

GCGCACATTTCCCCGAAAAGTGCCACCTGACGTC (SEQ ID NO: 40).
```

In certain embodiments, the heavy and light chain coding sequences are cloned into the NheI and EcoRI cut vector backbone. In certain embodiments, when the expressed antibody is histidine-tagged, the following coding sequence is appended to the 3' end of the last codon of the heavy chain constant region: -CAC CAT CAC CAT CAC CAT CAC CAT (SEQ ID NO: 41)- Stop codon.

The disclosure also provides host cells including a polynucleotide or a vector disclosed herein. Any of a variety of host cells or host cell lines can be used. In certain embodiments, a host cell is a prokaryotic cell, for example, E. coli. In certain embodiments, a host cell is a eukaryotic cell, for example, a mammalian cell, such as a Chinese Hamster Ovary (CHO) cell, COS cells, BHK cells, NSO cells or Bowes melanoma cells. Examples of human host cells are, inter alia, HeLa, 911, AT1080, A549, 293 and HEK293T cells. In certain embodiments, the host cell is a hepatocyte. In certain embodiments, the host cell is other than a hepatocyte. In certain embodiments, the host cell is a prokaryotic cell. In certain embodiments, the host cell is a eukaryotic cell. In certain embodiments, the host cell is an animal, fungal, or plant cell. In certain embodiments, the host cell is a mammalian cell (e.g., a mouse, rat, guinea pig, non-human primate, or isolated human cell). In certain embodiments, the host cell is an *Escherichia coli, Pseudomonas, Bacillus, Streptomyces*, yeast (e.g., *Pichia, Saccharomyces*), CHO, YB/20, NS0, PER-C6, HEK-293T, NIH-3T3, HeLa, BHK, Hep G2, SP2/0, R1.1, B-W, L-M, COS 1, COS 7, BSC1, BSC40, BMT10 cell, plant cell, insect cell, or an isolated human cell. In certain embodiments, the host cell is an *Escherichia coli* cell. In certain embodiments, the host cell is a *Pseudomonas* cell. In certain embodiments, the host cell is a *Bacillus* cell. In certain embodiments, the host cell is a *Streptomyces* cell. In certain embodiments, the host cell is a yeast cell. In certain embodiments, the host cell is a CHO cell. In certain embodiments, the host cell is a YB/20 cell. In certain embodiments, the host cell is a NSO cell. In certain embodiments, the host cell is a PER-C6 cell. In certain embodiments, the host cell is a HEK-293T cell. In certain embodiments, the host cell is a NIH-3T3 cell. In certain embodiments, the host cell is a HeLa cell. In certain embodiments, the host cell is a BHK cell. In certain embodiments, the host cell is a HepG2 cell. In certain embodiments, the host cell is a SP2/0 cell. In certain embodiments, the host cell is a R1.1 cell. In certain embodiments, the host cell is a B-W cell. In certain embodiments, the host cell is a L-M cell. In certain embodiments, the host cell is a COS 1 cell. In certain embodiments, the host cell is a COS 7 cell. In certain embodiments, the host cell is a BSC1 cell. In certain embodiments, the host cell is a BSC40 cell. In certain embodiments, the host cell is a BMT10 cell. In certain embodiments, the host cell is a plant cell. In certain embodiments, the host cell is an insect cell. In certain embodiments, the host cell is an isolated human cell. In certain embodiments, the host cell is an isolated human hepatocyte. In certain embodiments, the isolated human hepatocyte is in a population of primary hepatocytes or a cell of a hepatocyte cell line. In certain embodiments, the isolated human hepatocyte is in a population of primary hepatocytes. In certain embodiments, the isolated human hepatocyte is a cell of a hepatocyte cell line. In certain embodiments, the host cell is an isolated human hepatoma cell. In certain embodiments, the host cell is a HepG2 cell.

Cells including a polynucleotide or vector as described herein for use in treatment, diagnostic, research, drug screen, or other applications are provided. In certain embodiments, the cell is a primary cell. In certain embodiments, the cell is a cell line (e.g., an immortalized cell line). In certain embodiments, the cell is a cell that expresses recombinant HBx (e.g., a cell that is not infected with HBV and does not have HBV DNA integrated into its genome). In certain embodiments, the recombinant HBx is expressed from a vector such as a plasmid. Any of a variety of cells or cell lines can be used. In certain embodiments, a cell is a prokaryotic cell, for example, E. coli. In certain embodiments, a cell is a eukaryotic cell, for example, a mammalian cell, such as a Chinese Hamster Ovary (CHO) cell, COS cells, BHK cells, NSO cells or Bowes melanoma cells. Examples of human cells are, inter alia, HeLa, 911, AT1080, A549, 293 and HEK293T cells. In certain embodiments, the cell is a hepatocyte. In certain embodiments, the cell is other than a hepatocyte. In certain embodiments, the cell is a prokaryotic cell. In certain embodiments, the cell is a eukaryotic cell. In certain embodiments, the cell is an animal, fungal, or plant cell. In certain embodiments, the cell is a mammalian cell (e.g., a mouse, rat, guinea pig, non-human primate, or isolated human cell). In certain embodiments, the cell is an *Escherichia coli, Pseudomonas, Bacillus, Streptomyces*, yeast (e.g., *Pichia, Saccharomyces*), CHO, YB/20, NSO, PER-C6, HEK-293T, NIH-3T3, HeLa, BHK, Hep G2, SP2/0, R1.1, B-W, L-M, COS 1, COS 7, BSC1, BSC40, BMT10 cell, plant cell, insect cell, or an isolated human cell. In certain embodiments, the cell is an *Escherichia coli* cell. In certain embodiments, the cell is a *Pseudomonas* cell. In certain embodiments, the cell is a *Bacillus* cell. In certain embodiments, the cell is a *Streptomyces* cell. In certain embodiments, the cell is a yeast cell. In certain embodiments, the cell is a CHO cell. In certain embodiments, the cell is a YB/20 cell. In certain embodiments, the cell is a NSO cell. In certain embodiments, the cell is a PER-C6 cell. In certain embodiments, the cell is a HEK-293T cell. In certain embodiments, the cell is a NIH-3T3 cell. In certain embodiments, the cell is a HeLa cell. In certain embodiments, the cell is a BHK cell. In certain embodiments, the cell is a HepG2 cell. In certain embodiments, the cell is a SP2/0 cell. In certain embodiments, the cell is a R1.1 cell. In certain embodiments, the cell is a B-W cell. In certain embodiments, the cell is a L-M cell. In certain embodiments, the cell is a COS 1 cell. In certain embodiments, the cell is a COS 7 cell. In certain embodiments, the cell is a BSC1 cell. In certain embodiments, the cell is a BSC40 cell. In certain embodiments, the cell is a BMT10 cell. In certain embodiments, the cell is a plant cell. In certain embodiments, the cell is an insect cell. In certain embodiments, the cell is an isolated human cell. In certain embodiments, the cell is an isolated human hepatocyte. In certain embodiments, the isolated human hepatocyte is in a population of primary hepatocytes or a cell of a hepatocyte cell line. In certain embodiments, the isolated human hepatocyte is in a population of primary hepatocytes. In certain embodiments, the isolated human hepatocyte is a cell of a hepatocyte cell line. In certain embodiments, the cell is an isolated human hepatoma cell. In certain embodiments, the cell is a HepG2 cell. In certain embodiments, the cell is an immune cell such as a T-cell.

In an aspect is provided a chimeric antigen receptor (CAR) including an antigen-binding antibody fragment as described herein. In certain embodiments, the CAR is expressed on a T-cell or a NK cell.

In an aspect is provided a CAR T-cell including a CAR as described herein. In certain embodiments, the T-cell is a CD4+ T-cell, a CD8+ T-cell, or a combination thereof. In certain embodiments, the cell is administered to a subject. In certain embodiments, the cell is autologous. In certain embodiments, the cell is allogeneic.

V. Antibody Production Methods

In an aspect is provided a method of producing an antibody or antigen-binding antibody fragment as described herein including recombinantly expressing the antibody or antigen-binding antibody fragment in a cell as described herein.

Methods of making antibodies are very well known in the art. Methods of making bispecific antibodies are described, for example, in U.S. Pat. Nos. 5,731,168; 5,807,706; 5,821,333; and U.S. Appl. Publ. Nos. 2003/020734 and 2002/0155537. In certain embodiments, they are produced recombinantly or by chemical synthesis. For example, antibodies and antigen-binding fragments thereof may be produced synthetically or by enzymatic or chemical cleavage of intact immunoglobulins or they may be genetically engineered by recombinant DNA techniques. Such methods of production are well known in the art and are described, for example, in Antibodies: A Laboratory Manual, edited by E. Harlow and D. Lane (1988), Cold Spring Harbor Laboratory, Cold Spring Harbor, N.Y., which is incorporated herein by reference. The antibodies and antigen-binding antibody fragments may be produced synthetically or by enzymatic or chemical cleavage of intact immunoglobulins or they may be genetically engineered by recombinant DNA techniques. Illustrative methods of production are well known in the art and are described, for example, in Antibodies: A Laboratory Manual, edited by E. Harlow and D. Lane (1988), Cold Spring Harbor Laboratory, Cold Spring Harbor, N.Y. Various techniques have been developed for the production of antigen-binding antibody fragments. Traditionally, these fragments were derived via proteolytic digestion of intact antibodies (see, e.g., Morimoto et al., Journal of Biochemical and Biophysical Methods 24: 107-117 (1992); and Brennan et al., Science, 229:81 (1985)). However, these fragments can now be produced directly by recombinant host cells. Fab, Fv and scFv antigen-binding antibody fragments can all be expressed in and secreted from E. coli, thus allowing the facile production of large amounts of these fragments. Fab'-SH fragments can be directly recovered from E. coli and chemically coupled to form F(ab')$_2$ fragments (Carter et al., Bio/Technology 10: 163-167 (1992)). According to another approach, F(ab')$_2$ fragments can be isolated directly from recombinant host cell culture. Fab and F(ab')$_2$ fragment with increased in vivo half-life including a salvage receptor binding epitope residues are described in U.S. Pat. No. 5,869,046. Other techniques for the production of antibodies and antigen-binding antibody fragments will be apparent to the skilled practitioner.

In certain embodiments, an antibody or antigen-binding fragment thereof is produced by isolating the antibody or antigen-binding fragment thereof from a host cell including an expression vector that encodes the antibody or antigen-binding fragment thereof. In certain embodiments, the method further includes culturing the host cell under conditions suitable for expression of the antibody or antigen-binding fragment thereof and/or further includes introducing an expression vector encoding the antibody or antigen-binding fragment thereof into the host cell.

In an aspect is provided a method of producing an antibody or antigen-binding antibody fragment as described herein, or a heavy chain or light chain of the antibody, the method including culturing a cell under conditions such that a polynucleotide as described herein is expressed and the antibody, antigen-binding antibody fragment, or chain is produced. In certain embodiments, the cell is a host cell. In certain embodiments, the host cell includes a polynucleotide or vector as described herein. In certain embodiments, the cell is a prokaryotic cell. In certain embodiments, the cell is a eukaryotic cell. In certain embodiments, the cell is an animal, fungal, or plant cell. In certain embodiments, the cell is a mammalian cell (e.g., a mouse, rat, guinea pig, hamster, non-human primate, or isolated human cell). In certain embodiments, the cell is an insect cell.

In certain embodiments, the host cell is a eukaryotic cell, for example, a mammalian cell, such as a Chinese Hamster Ovary (CHO) cell, COS cells, BHK cells, NSO cells or Bowes melanoma cells. Examples of human host cells are, inter alia, HeLa, 911, AT1080, A549, 293 and HEK293T cells.

In certain embodiments, the host cell is an *Escherichia coli, Pseudomonas, Bacillus, Streptomyces*, yeast, CHO, YB/20, NSO, PER-C6, HEK-293T, NIH-3T3, HeLa, BHK, Hep G2, SP2/0, R1.1, B-W, L-M, COS 1, COS 7, BSC1, BSC40, BMT10 cell, plant cell, insect cell, or an isolated human cell.

In certain embodiments, the antibody or antigen-binding antibody fragment is a variant of a starting antibody with improved developability compared to the starting antibody. In certain embodiments, the antibody or antigen-binding antibody fragment is a variant of a starting antibody with reduced percent aggregation during production compared to the starting antibody. In certain embodiments, the starting antibody is HBx M19.

VI. Compositions and Kits

In an aspect, provided herein is a pharmaceutical composition including an antibody or antigen-binding antibody fragment as described herein, a polynucleotide as described herein, a vector as described herein, or a cell as described herein.

In certain embodiments, the pharmaceutical composition further includes a pharmaceutically acceptable carrier, excipient or diluent. In certain embodiments, the pharmaceutical composition further includes a pharmaceutically acceptable carrier. In certain embodiments, the pharmaceutical composition further includes an excipient. In certain embodiments, the pharmaceutical composition further includes a diluent. In certain embodiments, the pharmaceutical composition includes a therapeutically effective amount of the antibody as described herein, antigen-binding antibody fragment as described herein, polynucleotide as described herein, or cell (e.g. a CAR T-cell) as described herein.

Various pharmaceutically acceptable diluents, carriers, and excipients, and techniques for the preparation and use of pharmaceutical compositions will be known to those of skill in the art in light of the present disclosure. Illustrative pharmaceutical compositions and pharmaceutically acceptable diluents, carriers, and excipients are also described in Remington: The Science and Practice of Pharmacy 20th Ed. (Lippincott, Williams & Wilkins 2003). In certain embodiments, each carrier, diluent or excipient is "acceptable" in the sense of being compatible with the other ingredients of the pharmaceutical composition and not injurious to the subject. Often, the pharmaceutically acceptable carrier is an aqueous pH-buffered solution. Some examples of materials which can serve as pharmaceutically-acceptable carriers, diluents or excipients include: sterile water; buffers, e.g., phosphate-buffered saline; sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

In certain embodiments, pharmaceutical compositions are sterile. In certain embodiments, the pharmaceutical composition has a pH in the range of 4.5 to 8.5, 4.5 to 6.5, 6.5 to 8.5, or a pH of about 5.0, about 5.5, about 6.0, about 6.5, about 7.0, about 7.5, about 8.0 or about 8.5. In certain embodiments, the pharmaceutical composition has an osmolarity in the range of 240-260 or 250-330 mOsmol/L. In certain embodiments, the pharmaceutical composition is isotonic or near isotonic. In certain embodiments, the pharmaceutical composition is formulated for intravenous administration and has a concentration of antibody or antigen-binding fragment thereof of 10-100 mg/ml, 10-50 mg/ml, 20 to 40 mg/ml, or about 30 mg/ml. In certain embodiments, the pharmaceutical composition is formulated for subcutaneous injection and has a concentration of antibody or antigen-binding fragment thereof of 50-500 mg/ml, 50-250 mg/ml, or 100 to 150 mg/ml, and a viscosity less than 50 cP, less than 30 cP, less than 20 cP, or about 10 cP. In certain embodiments, the pharmaceutical compositions are liquids or solids. In certain embodiments, the pharmaceutical compositions are formulated for parenteral, e.g., intravenous, subcutaneous, or oral administration.

The formulation of and delivery methods of pharmaceutical compositions will generally be adapted according to the site and the disease to be treated. Exemplary formulations include, but are not limited to, those suitable for parenteral administration, e.g., intravenous, intra-arterial, intramuscular, or subcutaneous administration, including formulations encapsulated in micelles, liposomes or drug-release capsules (active agents incorporated within a biocompatible coating designed for slow-release); ingestible formulations; formulations for topical use, such as creams, ointments and gels; and other formulations such as inhalants, aerosols and sprays.

The present disclosure provides a kit including an antibody or antigen-binding fragment thereof of the present disclosure. In certain embodiments, the kit may further include instructions for use, e.g., for use in detecting HBx or treating a HBV infection. In certain embodiments, the use is for the in vitro detection and/or study of HBx, HBV infection, HBV integration, or a condition (such as cirrhosis or liver cancer) caused by HBV. In certain embodiments, the use is for the diagnostic detection or characterization of an HBV infection, HBV integration, or a condition (such as cancer) caused by HBV in a subject. In certain embodiments, the use is for the treatment of an HBV infection or a condition caused by an HBV infection (such as cirrhosis or liver cancer). The instructions for use are generally written instructions, although electronic storage media (e.g., magnetic diskette or optical disk) containing instructions are also acceptable.

Included herein is a kit including an antibody or pharmaceutical composition as described herein, and (i) a detection reagent and/or (ii) a HBx antigen. In certain embodiments, the kit includes an antibody as described herein, and (i) a detection reagent and/or (ii) a HBx antigen. In certain embodiments, the kit includes a pharmaceutical composition as described herein, and (i) a detection reagent and/or (ii) a HBx antigen.

The present disclosure also provides a pharmaceutical kit including one or more containers including an antibody or antigen-binding antibody fragment of the present disclosure. Optionally associated with such container(s) can be a notice in the form prescribed by a governmental agency regulating the manufacture, use or sale of pharmaceuticals, which notice reflects approval by the agency for the manufacture, use or sale for human administration. Each component (if there is more than one component) can be packaged in separate containers or some components can be combined in one container where cross-reactivity and shelf life permit. The kits may be in unit dosage forms, bulk packages (e.g., multi-dose packages) or sub-unit doses. Kits may also include multiple unit doses of the compounds (e.g., an antibody, antigen-binding antibody fragment, or polynucleotide) and instructions for use and be packaged in quantities sufficient for storage and use in pharmacies (e.g., hospital pharmacies and compounding pharmacies).

Also provided are articles of manufacture including a unit dosage of a compound of the present disclosure or a pharmaceutically acceptable salt thereof, in suitable packaging for use in the methods described herein. Suitable packaging is known in the art and includes, for example, vials, vessels, ampules, bottles, jars, flexible packaging and the like. An article of manufacture may further be sterilized and/or sealed.

VII. Methods of Use

Included herein are methods of detecting HBx. Such methods include contacting a sample believed to contain HBx with an antibody or antigen-binding antibody fragment as described herein, and detecting binding between HBx and the antibody or antigen-binding antibody fragment.

In certain embodiments, the sample includes a population of cells that have been contacted with (e.g., infected with) HBV, the progeny of cells that have been infected with HBV. In certain embodiments, the cells are cultured in vitro. In certain embodiments, the cells are from a sample taken from a subject, e.g., a biopsy. In certain embodiments, the sample includes the supernatant of a cell disclosed herein. In certain embodiments, the sample includes a population of cells that contains DNA or RNA that encodes HBx, e.g., recombinant HBx or integrated HBV DNA that encodes HBx. In certain embodiments, the sample includes a HBV virion, a HBV subviral particle, an extracellular vesicle, an extracellular microvesicle, an exosome, a cell that has been infected with HBV, a cell derived from a cell that was infected with HBV, a cell that expresses recombinant HBx, a cell whose genome includes integrated HBV DNA, a cell including a polynucleotide or vector that encodes recombinant HBx, or a cell including HBV viral DNA or mRNA encoding HBx. In certain embodiments, the sample includes a HBV virion. In certain embodiments, the sample includes a HBV subviral particle. In certain embodiments, the sample includes an extracellular vesicle. In certain embodiments, the sample includes an extracellular microvesicle. In certain embodiments, the sample includes an exosome. In certain embodiments, the sample includes a cell that has been infected with HBV. In certain embodiments, the sample includes a cell derived from a cell that was infected with HBV. In certain embodiments, the sample includes a cell that expresses recombinant HBx. In certain embodiments, the sample includes a cell whose genome includes integrated HBV DNA. In certain embodiments, the sample includes a cell including a polynucleotide or vector that encodes recombinant HBx. In certain embodiments, the sample includes a cell including HBV viral DNA or mRNA encoding HBx. In certain embodiments, the sample includes a cell including DNA or mRNA encoding recombinant HBx.

Also provided is a method of detecting HBx, the method including detecting whether HBx is present in a biological sample by contacting the sample with an antibody or antigen-binding antibody fragment as described herein, and detecting binding between HBx and the antibody or antigen-binding antibody fragment, wherein the biological sample is obtained from a subject.

In an aspect, provided herein are methods for detecting HBx, the method including (a) contacting a sample believed to contain HBx with an antibody or antigen-binding antibody fragment disclosed herein; and (b) (i) detecting binding between HBx and the antibody or antigen-binding antibody fragment, or (ii) immunoprecipitating the HBx with the antibody or antigen-binding antibody fragment followed by detecting the HBx. In certain embodiments, detecting the HBx includes mass spectrometry or chromatography. In certain embodiments, detecting the protein or HBx includes liquid chromatography-mass spectrometry (LC/MS) or high-performance liquid chromatography (HPLC).

In an aspect, provided herein is an immunoassay comprising contacting a sample including HBx with an antibody or antigen-binding antibody fragment disclosed herein. In certain embodiments, the immunoassay is a Western blot, an enzyme-linked immunosorbent assay (ELISA), immunocytochemistry, immunohistochemistry, or immunoelectrophoresis.

In an aspect, included herein are methods of diagnosing a HBV infection in a subject. In certain embodiments, the method includes (a) contacting a biological sample with an antibody or antigen-binding antibody fragment as described herein, wherein the sample is obtained from a subject; (b) detecting binding between HBx and the antibody or antigen-binding antibody fragment; and (c) diagnosing the subject with a HBV infection when the presence of HBx in the biological sample is detected.

In certain embodiments, the biological sample is a biopsy or cells derived from a biopsy (e.g., a primary culture of such cells or an expanded culture of such cells). In certain embodiments, the biological sample is other than a biopsy. In certain embodiments, the biological sample is a body fluid such as serum, plasma, whole blood, or urine.

In an aspect, included herein is a method of identifying genomic HBV DNA integration in a cell. In certain embodiments, the method includes (a) contacting the cell with an antibody or antigen-binding antibody fragment as described herein; (b) detecting binding between HBx and the antibody or antigen-binding antibody fragment; and (c) identifying the cell as including integrated genomic HBV DNA when the presence of HBx in the cell is detected.

In certain embodiments, the cell is a primary cell. In certain embodiments, the cell is a cell line (e.g., an immortalized cell line). In certain embodiments, the cell is a cell that expresses recombinant HBx (e.g., a cell that is not infected with HBV and does not have HBV DNA integrated into its genome). In certain embodiments, the cell is a hepatocyte. In certain embodiments, the cell is other than a hepatocyte. In certain embodiments, the cell is a prokaryotic cell. In certain embodiments, the cell is a eukaryotic cell. In certain embodiments, the cell is an animal, fungal, or plant cell. In certain embodiments, the cell is a mammalian cell (e.g., a mouse, rat, guinea pig, non-human primate, or isolated human cell).

In certain embodiments, the cell is an isolated human hepatoma cell. In certain embodiments, the cell is an isolated hepatocellular carcinoma cell. In certain embodiments, the cell is a HepG2 cell.

Also provided is a method of identifying whether a compound inhibits HBx, the method including (a) contacting a sample including a cell or a lysate thereof with an antibody or antigen-binding antibody fragment as described herein, wherein the cell has been contacted by the compound and expresses HBx; (b) detecting binding between HBx and the antibody or antigen-binding antibody fragment to determine the level of HBx in the sample; and (c) determining whether the level of HBx in the sample is lower than the level of HBx in a control sample, thereby identifying the compound as a compound that inhibits HBx.

In an aspect, provided herein is a method of identifying whether a compound inhibits HBx, the method including (a) contacting a sample including recombinant HBx with an antibody or antigen-binding antibody fragment described herein, wherein the recombinant HBx has been contacted by the compound; (b) detecting binding between recombinant HBx and the antibody or antigen-binding antibody fragment to determine the level of recombinant HBx in the sample; and (c) determining whether the level of recombinant HBx in the sample is lower than the level of recombinant HBx in a control sample, thereby identifying the compound as a compound that inhibits HBx.

In an aspect, provided herein are methods for identifying whether a compound inhibits HBx binding to an HBx-binding protein. In certain embodiments, such a method includes (a) contacting a sample including the compound, HBx, and the protein with an antibody or antigen-binding antibody fragment disclosed herein; (b) detecting binding between HBx and the protein; and (c) determining whether the level of HBx that is bound to the protein in the sample is lower than the level of HBx that is bound to the protein in a control sample, thereby identifying the compound as a compound that inhibits HBx binding. In certain embodiments, the level of HBx in the sample and the level of HBx in the control sample are about the same.

In certain embodiments, the compound is an organic compound having a molecular weight of less than 2000 daltons, less than 1000 daltons, or less than 500 daltons. In certain embodiments, the compound is an antisense oligonucleotide. In certain embodiments, the compound is an RNA interference molecule, such as an siRNA, miRNA, or shRNA molecule. In certain embodiments, the compound is an antibody or a fragment thereof, e.g., an intrabody (or a polynucleotide that expresses the intrabody).

In certain embodiments, a compound that inhibits HBx reduces HBx expression in the cell. In certain embodiments, a compound that inhibits HBx increases HBx degradation by a cell. In certain embodiments, a compound that inhibits HBx reduces a function or activity (e.g., DDB1 binding) of HBx.

In certain embodiments, a compound that inhibits HBx reduces binding between HBx to an HBx-binding protein. In certain embodiments, the compound binds to HBx. In certain embodiments, the compound binds to the protein.

In an aspect, provided herein are methods for detecting HBx binding to a protein. In certain embodiments, such a method includes (a) contacting a sample including HBx and the protein with an antibody or antigen-binding antibody fragment disclosed herein; and (b) detecting binding between HBx and the protein.

In certain embodiments, detecting binding between HBx and the protein includes detecting co-immunoprecipitation of the HBx and the protein.

In certain embodiments, detecting binding between HBx and the protein includes immunoprecipitation of the HBx with an antibody or antigen-binding antibody fragment disclosed herein followed by detecting the protein, wherein detecting the protein includes an immunoassay, mass spectrometry, or chromatography.

In certain embodiments, detecting binding between HBx and the protein includes immunoprecipitation of the protein followed by detecting HBx, wherein detecting HBx includes an immunoassay including an antibody or antigen-binding antibody fragment disclosed herein.

In certain embodiments, the immunoassay is a Western blot, an Enzyme-linked immunosorbent assay (ELISA), or immunoelectrophoresis.

In certain embodiments, detecting the protein or HBx includes liquid chromatography-mass spectrometry (LC/MS) or high-performance liquid chromatography (HPLC).

In certain embodiments, the sample does not include a cell or cell lysate. In certain embodiments, the sample includes isolated HBx. In certain embodiments, the HBx is recombinant HBx.

In certain embodiments, detecting binding between HBx and the antibody or antigen-binding antibody fragment includes contacting the antibody or antigen-binding antibody fragment with a secondary antibody with specificity for the antibody or antigen-binding antibody fragment (e.g., a Fc domain thereof). In certain embodiments, the antibody or antigen-binding antibody fragment is a rabbit monoclonal IgG, mouse monoclonal IgG, goat monoclonal IgG, rat monoclonal IgG, or chicken monoclonal IgG antibody and the secondary antibody is an anti-mouse IgG, anti-rabbit IgG, anti-goat IgG, anti-rat IgG, or anti-chicken IgG. In certain embodiments, the secondary antibody is a polyclonal antibody. In certain embodiments, the secondary antibody is conjugated to a detectable marker. In certain embodiments, the detectable marker is a colorimetric, chemiluminescent, or fluorescent compound.

In certain embodiments, the HBx is HBx genotype A or D. In certain embodiments, the HBx is HBx genotype A. In certain embodiments, the HBx is HBx genotype D. In certain embodiments, the HBx is HBx genotype B. In certain embodiments, the HBx is HBx genotype C. In certain embodiments, the HBx is HBx genotype E. In certain embodiments, the HBx is HBx genotype F. In certain embodiments, the HBx is HBx genotype G. In certain embodiments, the HBx is HBx genotype H. In certain embodiments, the HBx is HBx genotype I. In certain embodiments, the HBx is HBx genotype J.

Also provided are methods of inhibiting an increase in HBV virus titer, virus replication, virus proliferation, or human immunodeficiency virus infection in a subject. The method involves administering to the subject a therapeutically effective amount of an antibody, antigen-binding antibody fragment, polynucleotide, cell or pharmaceutical composition disclosed herein.

In an aspect, provided herein is a method of treating or preventing a HBV infection in a subject. The method includes administering to the subject an effective amount of an antibody, antigen-binding antibody fragment, polynucleotide, or cell disclosed herein (e.g., a pharmaceutical composition including the antibody, antigen-binding antibody fragment, polynucleotide, or cell). In certain embodiments, the antibody or antigen-binding antibody fragment is an intrabody.

In an aspect, included herein is a method of treating or preventing a HBV infection in a subject, the method including administering to the subject an effective amount of a polynucleotide that encodes an intrabody. In certain embodiments, the polynucleotide is a vector (e.g., a viral vector or a non-viral vector such as a plasmid). In certain embodiments, the vector is combined with a cationic condensing agent such as lipofectamine, polyethyleneimine, a dendrimer, chitosan, or poly-l-lysine. In certain embodiments, the intrabody lacks disulfide bonds. In certain embodiments, the intrabody is a fragment of an antibody. In certain embodiments, the intrabody is a single domain fragment such as an isolated VH or VL region. In certain embodiments, the intrabody is or includes a scFv. In certain embodiments, an intrabody is or includes a Fab. In certain embodiments, the intrabody includes a modification of an immunoglobulin VL region for hyperstability, is resistant to the reducing intracellular environment, and/or is expressed as a fusion protein with maltose binding protein or another stable intracellular protein. In certain embodiments, the intrabody includes the functional variable domain of a heavy-chain-only antibody of the family Camelidae (e.g., a chimeric variant of such an antibody including a variable domain described herein and/or 1, 2, 3, 4, 5, or 6 CDRs described herein), but no light chain. In certain embodiments, an intrabody includes a sub-cellular trafficking signal attached to the N or C terminus of the intrabody. In certain embodiments, the intrabody further includes a nuclear localization signal or a mitochondrial localization signal. In certain embodiments, the intrabody fragment further includes a nuclear localization signal. Non-limiting examples of nuclear localization signals include GGSGPPKKKRKV (SEQ ID NO: 42), PKKKRKV (SEQ ID NO: 43), KR[PAATKKAGQA] KKKK (SEQ ID NO: 44), KR[XXXXXXXXXX]KKKK (SEQ ID NO: 45), KKXK (SEQ ID NO: 46), KRXK (SEQ ID NO: 47), KKXR (SEQ ID NO: 48), KRXR (SEQ ID NO: 49), and AVKR-PAATKKAGQAKKKKLD (SEQ ID NO: 50), MSRRR-KANPTKLSENAKKLAKEVEN (SEQ ID NO: 51), PAAKRVKLD (SEQ ID NO: 52), PPKKKRKV (SEQ ID NO: 53), and KLKIKRPVK (SEQ ID NO: 54), where X is any amino acid. In certain embodiments, the nuclear localization signal is at an N-terminus of the intrabody. In certain embodiments, the nuclear localization signal is at a C-terminus of the intrabody. A non-limiting example of a mitochondrial localization signal includes MLSLRQ-SIRFFKPATRTLCSSRYLL (SEQ ID NO: 55). In certain embodiments, the mitochondrial localization signal is at an N-terminus of the intrabody. In certain embodiments, the mitochondrial localization signal is at a C-terminus of the intrabody.

In certain embodiments, the subject has been diagnosed with a HBV infection. In certain embodiments, the subject is believed to have been exposed to HBV. In certain embodiments, the subject is an at risk individual. In certain embodiments, the at risk individual is in a sexual relationship with someone who is infected with HBV. In certain embodiments, the at risk individual has had unprotected sex with someone who is infected with HBV. In certain embodiments, the at risk individual has shared a needle with another individual, e.g., during intravenous drug use. In certain embodiments, the at risk individual resides with someone who has a chronic HBV infection. In certain embodiments, the at risk individual is an infant whose mother has a HBV infection. In certain embodiments, the at risk individual has been exposed to human blood. In certain embodiments, the at risk individual has traveled, is traveling, or plans to travel to a region with a high infection rate of HBV within 1, 2, 3, 4, 5, or 6 days, within 1, 2, 3, 4, 5, or 6 weeks, or within 1, 2, 3, 4, 5, or 6 months. In certain embodiments, the region is Asia, a Pacific Island, Africa, or Eastern Europe.

In certain embodiments, the antibody or antigen-binding antibody fragment internalizes into a cell. In certain embodiments, the antibody or antigen-binding antibody fragment is a HBx antagonist. In certain embodiments, the antibody or antigen-binding antibody fragment is growth inhibitory. In certain embodiments, the antibody or antigen-binding antibody fragment induces apoptosis. In certain embodiments, the antibody or antigen-binding antibody fragment includes an Fc region with an effector function disclosed herein. In certain embodiments, the effector function is ADCC. In certain embodiments, the antibody or antigen-binding antibody fragment causes CDC. In certain embodiments, the antibody is a neutralizing antibody or a fragment thereof. In certain embodiments, the antibody is a non-neutralizing antibody or a fragment thereof.

In certain embodiments, a second therapeutic agent is administered to the subject. In certain embodiments, the second therapeutic agent is an antiviral agent.

In certain embodiments, the HBV is serotype adr. In certain embodiments, the HBV is serotype adw. In certain embodiments, the HBV is serotype ayr. In certain embodiments, the HBV is serotype ayw. In certain embodiments, the HBV includes genotype A. In certain embodiments, the HBV includes genotype B. In certain embodiments, the HBV includes genotype C. In certain embodiments, the HBV includes genotype D. In certain embodiments, the HBV includes genotype E. In certain embodiments, the HBV includes genotype F. In certain embodiments, the HBV includes genotype G. In certain embodiments, the HBV includes genotype H. In certain embodiments, the HBV includes genotype I. In certain embodiments, the HBV includes genotype J.

VIII. Administration

For in vivo treatment of a mammalian subject, e.g., a human, the subject may be administered or provided a pharmaceutical composition including an antibody, antigen-binding antibody fragment, polynucleotide, or cell described herein. In certain embodiments, when used for in vivo therapy, the antibodies described herein are typically administered or provided to the patient in therapeutically effective amounts (i.e., amounts that eliminate or reduce the patient's viral burden and/or viral reservoir). The antibodies are administered or provided to a mammalian subject, e.g., a human, in accord with known methods, such as, but not limited to, intravenous administration, e.g., as a bolus or by continuous infusion over a period of time, by intramuscular, intraperitoneal, intracerebrospinal, subcutaneous, intraarticular, intrasynovial, intrathecal, oral, topical, or inhalation routes. In certain embodiments, the antibodies may be administered parenterally, when possible, at the target cell site, or intravenously. In certain embodiments, administration of the antibody to the subject is via an intravenous route. In certain embodiments, administration of the antibody to the subject is via a subcutaneous route. In certain embodiments, pharmaceutical compositions of the disclosure are administered to a subject systemically, parenterally, or locally.

In certain embodiments, a vector encoding an antibody or antigen-binding antibody fragment of the present disclosure (e.g., an intrabody disclosed herein) is administered to a subject. In each embodiment described below that refers to "an antibody or antigen-binding antibody fragment" a corresponding embodiment relating to the administration of a vector that encodes the antibody or antigen-binding antibody fragment is also contemplated.

In certain embodiments, an antibody or antigen-binding antibody fragment of the present disclosure may be administered to a subject in accordance with an effective dosing regimen for a desired period of time or duration, such as at least about 1 month, at least about 2 months, at least about 3 months, at least about 6 months, or at least about 12 months or longer. In certain embodiments, the antibody or antigen-binding antibody fragment is administered on a daily, weekly, monthly or intermittent schedule for the duration of the individual's life.

In certain embodiments, the dosage or dosing frequency of an antibody or antigen-binding antibody fragment of the present disclosure may be adjusted over the course of the treatment, based on the judgment of the administering physician.

In certain embodiments, a single dose can be administered hourly, daily, or weekly. For example, a single dose can be administered once every 1, 2, 3, 4, 6, 8, 12, 16, or 24 hours. In certain embodiments, a single dose can be administered once every 1, 2, 3, 4, 5, 6, or 7 days. In certain embodiments, a single dose can be administered once every 1, 2, 3, or 4 weeks. In certain embodiments, a single dose can be administered once every week. In certain embodiments, a single dose can also be administered once every 1, 2, 3, 4, 5, or 6 months. In certain embodiments, a single dose can also be administered once every month.

The frequency of dosage of the antibody or antigen-binding antibody fragment of the present disclosure will be determined by the needs of the individual patient and can be, for example, once per day or twice, or more times, per day. In certain embodiments, administration of the antibody or antigen-binding antibody fragment continues for as long as necessary to treat the HBV infection. For example, an antibody or antigen-binding antibody fragment can be administered to a human being infected with HBV for a period of from 20 days to 180 days or, for example, for a period of from 20 days to 90 days or, for example, for a period of from 30 days to 60 days.

In certain embodiments, administration can be intermittent, with a period of several or more days during which a patient receives a daily dose of the antibody or antigen-binding antibody fragment of the present disclosure followed by a period of several or more days during which a patient does not receive a daily dose of the antibody or antigen-binding antibody fragment. For example, a patient can receive a dose of the antibody or antigen-binding antibody fragment every other day, or three times per week. Again by way of example, a patient can receive a dose of the antibody or antigen-binding antibody fragment each day for a period of from 1 to 14 days, followed by a period of 7 to 21 days during which the patient does not receive a dose of the antibody or antigen-binding antibody fragment, followed by a subsequent period (e.g., from 1 to 14 days) during which the patient again receives a daily dose of the antibody or antigen-binding antibody fragment. Alternating periods of administration of the antibody or antigen-binding antibody fragment, followed by non-administration of the antibody or antigen-binding antibody fragment, can be repeated as clinically required to treat the patient.

HBV Combination Therapies

In certain embodiments, pharmaceutical compositions including an antibody or antigen-binding antibody fragment of the present disclosure, or a pharmaceutically acceptable salt thereof, in combination with one or more (e.g., one, two, three, four, one or two, one to three, or one to four) additional therapeutic agents, and a pharmaceutically acceptable excipient are provided.

In certain embodiments, kits including an antibody or antigen-binding antibody fragment of the present disclosure, or a pharmaceutically acceptable salt thereof, in combination with one or more (e.g., one, two, three, four, one or two, one to three, or one to four) additional therapeutic agents are provided.

In certain embodiments, an antibody or antigen-binding antibody fragment of the present disclosure, or a pharmaceutically acceptable salt thereof, is combined with one, two, three, four or more additional therapeutic agents. In certain embodiments, an antibody or antigen-binding antibody fragment of the present disclosure, or a pharmaceutically acceptable salt thereof, is combined with two additional therapeutic agents. In certain embodiments, an antibody or antigen-binding antibody fragment of the present disclosure, or a pharmaceutically acceptable salt thereof, is combined with three additional therapeutic agents. In certain embodiments, an antibody or antigen-binding antibody fragment of the present disclosure, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In certain embodiments, when an antibody or antigen-binding antibody fragment of the present disclosure is combined with one or more additional therapeutic agents as described herein, the components of the composition are administered as a simultaneous or sequential regimen. When administered sequentially, the combination may be administered in two or more administrations.

Co-administration of an anti-HBx antibody or antigen-binding fragment thereof disclosed herein with one or more additional therapeutic agents generally refers to simultaneous or sequential administration of an anti-HBx antibody or antigen-binding fragment thereof disclosed herein and one or more additional therapeutic agents, such that therapeutically effective amounts of each agent are present in the body of the patient.

Co-administration includes administration of unit dosages of the anti-HBx antibodies or antigen-binding fragments disclosed herein before or after administration of unit dosages of one or more additional therapeutic agents. The antibodies and antigen-binding fragments disclosed herein may be administered within seconds, minutes, or hours of the administration of one or more additional therapeutic agents. For example, in some embodiments, a unit dose of an antibody or antigen-binding fragment disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of an antibody or antigen-binding fragment disclosed herein within seconds or minutes. In some embodiments, a unit dose of an antibody or antigen-binding fragment disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of an antibody or antigen-binding fragment disclosed herein.

In certain embodiments, an antibody or antigen-binding antibody fragment of the present disclosure is combined with one or more additional therapeutic agents in a unitary dosage form for simultaneous administration to a patient, for example as a solid dosage form for oral administration.

In certain embodiments, an antibody or antigen-binding antibody fragment of the present disclosure, is combined with one, two, three, four or more additional therapeutic agents selected from HBV combination drugs, HBV vaccines, HBV DNA polymerase inhibitors, immunomodulators, toll-like receptor (TLR) modulators, interferon alpha receptor ligands, hyaluronidase inhibitors, hepatitis b core antigen (HBcAg) inhibitors, hepatitis b surface antigen (HBsAg) inhibitors, cytotoxic T-lymphocyte-associated protein 4 (ipi4) inhibitors, cyclophilin inhibitors, HBV viral entry inhibitors, antisense oligonucleotide targeting viral mRNA, short interfering RNAs (siRNA) and ddRNAi, endonuclease modulators, ribonucelotide reductase inhibitors, HBV E antigen inhibitors, covalently closed circular DNA (cccDNA) inhibitors, farnesoid X receptor agonists, STING agonists, anti-HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2, 3-dioxygenase (IDO) pathway inhibitors, PD-1 inhibitors, PD-L1 inhibitors, recombinant thymosin alpha-1, bruton's tyrosine kinase (BTK) inhibitors, KDM inhibitors, HBV replication inhibitors, arginase inhibitors, gene therapy and cell therapy, gene editors, CAR-T cell therapy, TCR-T cell therapy, and other HBV drugs.

In certain embodiments, an anti-HBx antibody or antigen-binding antibody fragment thereof, as described herein, may be used or combined with one or more of a chemotherapeutic agent, an immunomodulator, an immunotherapeutic agent, a therapeutic antibody, a therapeutic vaccine, a bispecific antibody and "antibody-like" therapeutic protein (such as DARPins®, anti-pMHC TCR-like antibodies, DARTs®, Duobodies®, Bites®, XmAbs®, TandAbs®, Fab derivatives), an antibody-drug conjugate (ADC), gene modifiers or gene editors (such as CRISPR Cas9, zinc finger nucleases, homing endonucleases, homing meganucleases (e.g., ARCUS), synthetic nucleases, TALENs), cell therapies such as CAR-T (chimeric antigen receptor T-cell), and TCR-T (an engineered T cell receptor) agent or any combination thereof.

In certain embodiments, an anti-HBx antibody or antigen-binding antibody fragment thereof, as described herein, is combined with one, two, three, four or more additional therapeutic agents, e.g., as 3-dioxygenase (IDO) inhibitors, apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting hepatitis B core antigen (HBcAg), core protein allosteric modulators, covalently closed circular DNA (cccDNA) inhibitors, cyclophilin inhibitors, cytotoxic T-lymphocyte-associated protein 4 (ipi4) inhibitors, DNA polymerase inhibitor, endonuclease modulators, epigenetic modifiers, Farnesoid X receptor agonists, HBV DNA polymerase inhibitors, HBV replication inhibitors, HBV RNAse inhibitors, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, inhibitor of apoptosis proteins family proteins (IAPs) inhibitors, IL-2 agonist, IL-7 agonist, immunomodulators, indoleamine-2 inhibitors, inhibitors of ribonucleotide reductase, Interleukin-2 ligand, ipi4 inhibitors, lysine demethylase inhibitors, histone demethylase inhibitors, KDM1 inhibitors, KDM5 inhibitors, killer cell lectin-like receptor subfamily G member 1 inhibitors, lymphocyte-activation gene 3 inhibitors, lymphotoxin beta receptor activators, modulators of Axl, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, OX-40 receptor agonist, PD-1 inhibitors, PD-L1 inhibitors, peptidylprolyl isomerase inhibitor, phosphatidylinositol-3 kinase (PI3K) inhibitors, Retinoic acid-inducible gene 1 stimulator, Reverse transcriptase inhibitor, Ribonuclease inhibitor, RNA DNA polymerase inhibitor, SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR-3 agonists, TLR-7 agonists, TLR-9 agonists, TLR9 agonists or gene stimulator, toll-like receptor (TLR) modulators, viral ribonucleotide reductase inhibitors, and combinations thereof.

HBV Combination Drugs

Examples of combination drugs for the treatment of HBV include TRUVADA® (tenofovir disoproxil fumarate and emtricitabine); ABX-203, lamivudine, and PEG-IFNalpha; ABX-203 adefovir, and PEG-IFNalpha; and INO-1800 (INO-9112 and RG7944).

Other HBV Drugs

Examples of other drugs for the treatment of HBV include alpha-hydroxytropolones, amdoxovir, antroquinonol, beta-hydroxycytosine nucleosides, AL-034, CCC-0975, elvucitabine, ezetimibe, cyclosporin A, gentiopicrin (gentiopicroside), JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-0061A, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, UB-551, and ZH-2N, and the compounds disclosed in US20150210682, (Roche), US 2016/0122344 (Roche), WO2015173164, WO2016023877, US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche).

HBV Vaccines

HBV vaccines include both prophylactic and therapeutic vaccines. Examples of HBV prophylactic vaccines include Vaxelis, Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, ENGERIX B®, recombinant hepatitis B vaccine (intramuscular, Kangtai Biological Products), recombinant hepatitis B vaccine (Hansenual polymorpha yeast, intramuscular, Hualan Biological Engineering), recombinant hepatitis B surface antigen vaccine, Bimmugen, Euforavac, Eutravac, anrix-DTaP-IPV-Hep B, HBAI-20, Infanrix-DTaP-IPV-Hep B-Hib, Pentabio Vaksin DTP-HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPERVAX, Comvac5, Shanvac-B, Hebsulin, Recombivax HB, Revac B mcf, Revac B+, Fendrix, DTwP-HepB-Hib, DNA-001, Shan5, Shan6, rhHBsAG vaccine, HBI pentavalent vaccine, LBVD, Infanrix HeXa, and DTaP-rHB-Hib vaccine.

Examples of HBV therapeutic vaccines include HBsAG-HBIG complex, ARB-1598, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IP-321, BEVAC, Revac B mcf, Revac B+, MGN-1333, KW-2, CVI-HBV-002, AltraHepB, VGX-6200, FP-02, FP-02.2 (HepTeell), TG-1050, NU-500, HBVax, im/TriGrid/antigen vaccine, Mega-CD40L-adjuvanted vaccine, HepB-v, RG7944 (INO-1800), recombinant VLP-based therapeutic vaccine (HBV infection, VLP Biotech), AdTG-17909, AdTG-17910 AdTG-18202, ChronVac-B, TG-1050, VVX-001, and Lm HBV. HBV Arenavirus vaccines are described, e.g., in WO2017076988 and WO2017198726.

HBV DNA Polymerase Inhibitors

Examples of HBV DNA polymerase inhibitors include adefovir (HEPSERA®), emtricitabine (EMTRIVA®), tenofovir disoproxil fumarate (VREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, besifovir, entecavir (BARACLUDE®), entecavir maleate, telbivudine (TYZEKA®), filocilovir, pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234.

Immunomodulators

Examples of immunomodulators include rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), JNJ-440, WF-10, AB-452, ribavirin, IL-12, INO-9112, polymer polyethyleneimine (PEI), Gepon, VGV-1, MOR-22, CRV-431, JNJ-0535, TG-1050, ABI-H2158, BMS-936559, GS-9688, RO-7011785, RG-7854, AB-506, RO-6871765, AIC-649, and IR-103.

Toll-Like Receptor (TLR) Modulators

TLR modulators include modulators of TLR1, TLR2, TLR3, TLR4, TLR5, TLR6, TLR7, TLR8, TLR9, TLR10, TLR11, TLR12, and TLR13. Examples of TLR3 modulators include rintatolimod, poly-ICLC, RIBOXXON®, Apoxxim, RIBOXXIM®, IPH-33, MCT-465, MCT-475 and ND-1.1.

Examples of TLR7 modulators include GS-9620, GSK-2245035, imiquimod, resiquimod, DSR-6434, DSP-3025, IMO-4200, MCT-465, MEDI-9197, 3M-051, SB-9922, 3M-052, Limtop, D, telratolimod, SP-0509, TMX-30X, TMX-202, RG-7863, RG-7795, RG-7854, and the compounds disclosed in US20100143301 (Gilead Sciences), US20110098248 (Gilead Sciences), and US20090047249 (Gilead Sciences).

Examples of TLR8 modulators include motolimod, GS-9688, resiquimod, 3M-051, 3M-052, MCT-465, IMO-4200, VTX-763, VTX-1463, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), US20130251673 (Novira Therapeutics), U.S. Pat. No. 9,670,205 (Gilead Sciences, Inc.), US20160289229 (Gilead Sciences, Inc.), WO2017/048727 (Gilead Sciences, Inc.), US20180065938 (Gilead Sciences, Inc.), and US20180086755 (Gilead Sciences, Inc.).

Examples of TLR9 modulators include BB-001, BB-006, CYT-003, IMO-2055, IMO-2125, IMO-3100, IMO-8400, IR-103, IMO-9200, agatolimod, DIMS-9054, DV-1079, DV-1179, AZD-1419, leftolimod (MGN-1703), litenimod, and CYT-003-QbG10.

Examples of TLR7, TLR8 and TLR9 modulators include the compounds disclosed in WO2017047769 (Teika Seiyaku), WO2015014815 (Janssen), WO2018045150 (Gilead Sciences Inc), WO2018045144 (Gilead Sciences Inc), WO2015162075 (Roche), WO2017034986 (University of Kansas), WO2018095426 (Jiangsu Hengrui Medicine Co Ltd), WO2016091698 (Roche), WO2016075661 (GaxoSmithKline Biologicals), WO2016180743 (Roche), WO2018089695 (Dynavax Technologies), WO2016055553 (Roche), WO2015168279 (Novartis), WO2016107536 (Medshine Discovery), WO2018086593 (Livo (Shanghai) Pharmaceutical), WO2017106607 (Merck), WO2017061532 (Sumitomo Dainippon Pharma), WO2016023511 (Chia Tai Tianqing Pharmaceutical), WO2017076346 (Chia Tai Tianqing Pharmaceutical), WO2017046112 (Roche), WO2018078149 (Roche), WO2017040233 (3M Co), WO2016141092 (Gilead Sciences), WO2018049089 (BristolMyers Squibb), WO2015057655 (Eisai Co Ltd), WO2017001307 (Roche), WO2018005586 (BristolMyers Squibb), WO201704023 (3M Co), WO2017163264 (Council of Scientific and Industrial Research (India)), WO2018046460 (GlaxoSmithKline Biologicals), WO2018047081 (Novartis), WO2016142250 (Roche), WO2015168269 (Novartis), WO201804163 (Roche), WO2018038877 (3M Co), WO2015057659 (Eisai Co Ltd), WO2017202704 (Roche), WO2018026620 (BristolMyers Squibb), WO2016029077 (Janus Biotherapeutics), WO201803143 (Merck), WO2016096778 (Roche), WO2017190669 (Shanghai De Novo Pharmatech), U.S. Ser. No. 09/884,866 (University of Minnesota), WO2017219931 (Sichuan KelunBiotech Biopharmaceutical), WO2018002319 (Janssen Sciences), WO2017216054 (Roche), WO2017202703 (Roche), WO2017184735 (IFM Therapeutics), WO2017184746 (IFM Therapeutics), WO2015088045 (Takeda Pharmaceutical), WO2017038909 (Takeda Pharmaceutical), WO2015095780 (University of Kansas), WO2015023958 (University of Kansas).

In certain embodiments, an anti-HBx antibody or antigen-binding fragment, as described herein is co-administered with a TLR7, TLR8 or TLR9 agonist.

Interferon Alpha Receptor Ligands

Examples of interferon alpha receptor ligands include interferon alpha-2b (INTRON A®), pegylated interferon alpha-2a (PEGASYS®), PEGylated interferon alpha-1b, interferon alpha 1b (HAPGEN®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-INTRON®), Bioferon, Novaferon, Inmutag (Inferon), MULTIFERON, interferon alfa-n1 (HUMOFERON®), interferon beta-1a (AVONEX®), Shaferon, interferon alfa-2b (Axxo), Alfaferone, interferon alfa-2b (BioGeneric Pharma), interferon-alpha 2 (CJ), Laferonum, VIPEG, BLAUFERON-A, BLAUFERON-B, Intermax Alpha, Realdiron, Lanstion, Pegaferon, PDferon-B PDferon-B, interferon alfa-2b (IFN, Laboratorios Bioprofarma), alfainterferona 2b, Kalferon, Pegnano, Feronsure, PegiHep, interferon alfa 2b (Zydus-Cadila), interferon alfa 2a, Optipeg A, Realfa 2B, Reliferon, interferon alfa-2b (Amega), interferon alfa-2b (Virchow), ropeginterferon alfa-2b, rHSA-IFN alpha-2a (recombinant human serum albumin intereferon alpha 2a fusion protein), rHSA-IFN alpha 2b, recombinant human interferon alpha-(1b, 2a, 2b), peginterferon alfa-2b (Amega), peginterferon alfa-2a, Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINO-GEN, Fukangtai, Pegstat, rHSA-IFN alpha-2b, SFR-9216, and Interapo (Interapa).

Hyaluronidase Inhibitors

Examples of hyaluronidase inhibitors include astodrimer.

Hepatitis B Surface Antigen (HBsAg) Inhibitors

Examples of HBsAg inhibitors include AK-074, HBF-0259, PBHBV-001, PBHBV-2-15, PBHBV-2-1, REP-9AC, REP-9C, REP-9, REP-2139, REP-2139-Ca, REP-2165, REP-2055, REP-2163, REP-2165, REP-2053, REP-2031 and REP-006, and REP-9AC'.

Examples of HBsAg secretion inhibitors include BM601.

Cytotoxic T-Lymphocyte-Associated Protein 4 (Ipi4) Inhibitors

Examples of Cytotoxic T-lymphocyte-associated protein 4 (ipi4) inhibitors include AGEN-2041, AGEN-1884, ipilumimab, belatacept, PSI-001, PRS-010, Probody mAbs, tremelimumab, and JHL-1155.

Cyclophilin Inhibitors

Examples of cyclophilin inhibitors include CPI-431-32, EDP-494, OCB-030, SCY-635, NVP-015, NVP-018, NVP-019, STG-175, and the compounds disclosed in U.S. Pat. No. 8,513,184 (Gilead Sciences), US20140030221 (Gilead Sciences), US20130344030 (Gilead Sciences), and US20130344029 (Gilead Sciences).

HBV Viral Entry Inhibitors

Examples of HBV viral entry inhibitors include Myrcludex B.

Antisense Oligonucleotide Targeting Viral mRNA

Examples of antisense oligonucleotide targeting viral mRNA include ISIS-HBVRx, IONIS-HBVRx, IONIS-HBV-LRx, IONIS-GSK6-LRx, GSK-3389404, and RG-6004.

Short Interfering RNAs (siRNA) and ddRNAi

Examples of siRNA include TKM-HBV (TKM-HepB), ALN-HBV, SR-008, HepB-nRNA, ARC-520, ARC-521, ARB-1740, ARB-1467, DCR-HBVS, RG-6217, ALN-HBV-02, ARO-HBV and DCR-HBVS (DCR-S219).

Examples of DNA-directed RNA interference (ddRNAi) include BB-HB-331.

Endonuclease Modulators

Examples of endonuclease modulators include PGN-514.

Ribonucelotide Reductase Inhibitors

Examples of inhibitors of ribonucleotide reductase include Trimidox.

HBV E Antigen Inhibitors

Examples of HBV E antigen inhibitors include wogonin.

Covalently Closed Circular DNA (cccDNA) Inhibitors

Examples of cccDNA inhibitors include BSBI-25, and CHR-101.

Farnesoid X receptor agonist

Examples of farnesoid x receptor agonists include, e.g., EYP-001, GS-9674, EDP-305, MET-409, Tropifexor, AKN-083, RDX-023, BWD-100, LMB-763, INV-3, NTX-023-1, EP-024297 and GS-8670.

Additional HBV Antibodies

Examples of HBV antibodies targeting the surface antigens of the hepatitis B virus include lenvervimab (GC-1102), XTL-17, XTL-19, KN-003, IV Hepabulin SN, and fully human monoclonal antibody therapy (hepatitis B virus infection, Humabs BioMed).

Examples of HBV antibodies, including monoclonal antibodies and polyclonal antibodies, include Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products), and Fovepta (BT-088).

Examples of fully human monoclonal antibodies include HBC-34.

Antibodies against HBV viral peptide/major histocompatibility complex (MHC) class I (pMHC) complexes are described, e.g., in Sastry, et al., J Virol. 2011 March; 85(5):1935-42 and in WO2011062562.

CCR2 Chemokine Antagonists

Examples of CCR2 chemokine antagonists include propagermanium.

Thymosin Agonists

Examples of thymosin agonists include Thymalfasin, and recombinant thymosin alpha 1 (GeneScience).

Cytokines

Examples of cytokines include recombinant IL-7, CYT-107, interleukin-2 (IL-2, Immunex), recombinant human interleukin-2 (Shenzhen Neptunus), IL-15, IL-21, IL-24, and celmoleukin.

Nucleoprotein Modulators

Nucleoprotein modulators may be either HBV core or capsid protein inhibitors. Examples of nucleoprotein modulators include GS-4882, AB-423, AT-130, GLS4, NVR-1221, NVR-3778, AL-3778, BAY 41-4109, morphothiadine mesilate, ARB-168786, ARB-880, JNJ-379, RG-7907, HEC-72702, AB-506, ABI-H0731, JNJ-440, ABI-H2158 and DVR-23.

Examples of capsid inhibitors include the compounds disclosed in US20140275167 (Novira Therapeutics), US20130251673 (Novira Therapeutics), US20140343032 (Roche), WO2014037480 (Roche), US20130267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), WO2017198744 (Roche), US 20170334882 (Novira), US 20170334898 (Roche), WO2017202798 (Roche), WO2017214395 (Enanta), WO2018001944 (Roche), WO2018001952 (Roche), WO2018005881 (Novira), WO2018005883 (Novira), WO2018011100 (Roche), WO2018011160 (Roche), WO2018011162 (Roche), WO2018011163 (Roche), WO2018036941 (Roche), WO2018043747 (Kyoto Univ), US20180065929 (Janssen), WO2016168619 (Indiana University), WO2016195982 (The Penn State Foundation), WO2017001655 (Janssen), WO2017048950 (Assembly Biosciences), WO2017048954 (Assembly Biosciences), WO2017048962 (Assembly Biosciences), US20170121328 (Novira), US20170121329 (Novira).

Examples of transcript inhibitors include the compounds disclosed in WO2017013046 (Roche), WO2017016960 (Roche), WO2017017042 (Roche), WO2017017043 (Roche), WO2017061466 (Toyoma chemicals), WO2016177655 (Roche), WO2016161268 (Enanta). WO2017001853 (Redex Pharma), WO2017211791 (Roche), WO2017216685 (Novartis), WO2017216686 (Novartis), WO2018019297 (Ginkgo Pharma), WO2018022282 (Newave Pharma), US20180030053 (Novartis), WO2018045911 (Zhejiang Pharma).

Retinoic Acid-Inducible Gene 1 Stimulators

Examples of stimulators of retinoic acid-inducible gene 1 include inarigivir soproxil (SB-9200), SB-40, SB-44, ORI-7246, ORI-9350, ORI-7537, ORI-9020, ORI-9198, ORI-7170, and RGT-100.

NOD2 Stimulators

Examples of stimulators of NOD2 include inarigivir soproxil (SB-9200).

Phosphatidylinositol 3-Kinase (PI3K) Inhibitors

Examples of PI3K inhibitors include idelalisib, ACP-319, AZD-8186, AZD-8835, buparlisib, CDZ-173, CLR-457, pictilisib, neratinib, rigosertib, rigosertib sodium, EN-3342, TGR-1202, alpelisib, duvelisib, IPI-549, UCB-5857, taselisib, XL-765, gedatolisib, ME-401, VS-5584, copanlisib, CAI orotate, perifosine, RG-7666, GSK-2636771, DS-7423, panulisib, GSK-2269557, GSK-2126458, CUDC-907, PQR-309, INCB-40093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301, TAK-117, HMPL-689, tenalisib, voxtalisib, and CLR-1401.

Indoleamine-2, 3-dioxygenase (IDO) Pathway Inhibitors

Examples of IDO inhibitors include epacadostat (INCB24360), resminostat (4SC-201), indoximod, F-001287, SN-35837, NLG-919, GDC-0919, GBV-1028, GBV-1012, NKTR-218, and the compounds disclosed in US20100015178 (Incyte), US2016137652 (Flexus Biosciences, Inc.), WO2014073738 (Flexus Biosciences, Inc.), and WO2015188085 (Flexus Biosciences, Inc.).

PD-1 Inhibitors

Examples of PD-1 inhibitors include cemiplimab, nivolumab, pembrolizumab, pidilizumab, BGB-108, STI-A1014, SHR-1210, PDR-001, PF-06801591, IBI-308, GB-226, STI-1110, JNJ-63723283, CA-170, durvalumab, atezolizumab, mDX-400, JS-001, camrelizumab, sintilimab, tislelizumab, BCD-100, BGB-A333, JNJ-63723283, GLS-010 (WBP-3055), CX-072, AGEN-2034, GNS-1480 (Epidermal growth factor receptor antagonist; Programmed cell death ligand 1 inhibitor) and CS-1001.

M-7824 (PD-L1/TGF-β bifunctional fusion protein), Genolimzumab and BMS-936559.

PD-L1 Inhibitors

Examples of PD-L1 inhibitors include atezolizumab, avelumab, AMP-224, MEDI-0680, RG-7446, GX-P2, durvalumab, KY-1003, KD-033, KN-035, MSB-0010718C, TSR-042, ALN-PDL, STI-A1014, GS-4224, CX-072, and BMS-936559.

Examples of PD-1 inhibitors include the compounds disclosed in WO2017112730 (Incyte Corp), WO2017087777 (Incyte Corp), WO2017017624, WO2014151634 (BristolMyers Squibb Co), WO201317322 (BristolMyers Squibb Co), WO2018119286 (Incyte Corp), WO2018119266 (Incyte Corp), WO2018119263 (Incyte Corp), WO2018119236 (Incyte Corp), WO2018119221 (Incyte Corp), WO2018118848 (BristolMyers Squibb Co), WO20161266460 (BristolMyers Squibb Co), WO2017087678 (BristolMyers Squibb Co), WO2016149351 (BristolMyers Squibb Co), WO2015033299 (Aurigene Discovery Technologies Ltd), WO2015179615 (Eisai Co Ltd; Eisai Research Institute), WO2017066227 (BristolMyers Squibb Co), WO2016142886 (Aurigene Discovery Technologies Ltd), WO2016142852 (Aurigene Discovery Technologies Ltd), WO2016142835 (Aurigene Discovery Technologies Ltd; Individual), WO2016142833 (Aurigene Discovery Technologies Ltd), WO2018085750 (BristolMyers Squibb Co), WO2015033303 (Aurigene Discovery Technologies Ltd), WO2017205464 (Incyte Corp), WO2016019232 (3M Co; Individual; Texas A&M University System), WO2015160641 (BristolMyers Squibb Co), WO2017079669 (Incyte Corp), WO2015033301 (Aurigene Discovery Technologies Ltd), WO2015034820 (BristolMyers Squibb Co), WO2018073754 (Aurigene Discovery Technologies Ltd), WO2016077518 (BristolMyers Squibb Co), WO2016057624 (BristolMyers Squibb Co), WO2018044783 (Incyte Corp), WO2016100608 (BristolMyers Squibb Co), WO2016100285 (BristolMyers Squibb Co), WO2016039749 (BristolMyers Squibb Co), WO2015019284 (Cambridge Enterprise Ltd), WO2016142894 (Aurigene Discovery Technologies Ltd), WO2015134605 (BristolMyers Squibb Co), WO2018051255 (Aurigene Discovery Technologies Ltd), WO2018051254 (Aurigene Discovery Technologies Ltd), WO2017222976 (Incyte Corp), WO2017070089 (Incyte Corp), WO2018044963 (BristolMyers Squibb Co), WO2013144704 (Aurigene Discovery Technologies Ltd), WO2018013789 (Incyte Corp), WO2017176608 (BristolMyers Squibb Co), WO2018009505 (BristolMyers Squibb Co), WO2011161699 (Aurigene Discovery Technologies Ltd), WO2015119944 (Incyte Corp; Merck Sharp & Dohme Corp), WO2017192961 (Incyte Corp), WO2017106634 (Incyte Corp), WO2013132317 (Aurigene Discovery Technologies Ltd), WO2012168944 (Aurigene Discovery Technologies Ltd), WO2015036927 (Aurigene Discovery Technologies Ltd), WO2015044900 (Aurigene Discovery Technologies Ltd), WO2018026971 (Arising International).

OX-40 Receptor Agonists

Examples of OX-40 receptor agonists include IBI-101.

Inhibitor of Apoptosis Proteins Family Proteins (IAPs)

Examples of IAP inhibitors include APG-1387.

Recombinant Thymosin Alpha-1

Examples of recombinant thymosin alpha-1 include NL-004 and PEGylated thymosin alpha-1.

Bruton's Tyrosine Kinase (BTK) Inhibitors

Examples of BTK inhibitors include ABBV-105, acalabrutinib (ACP-196), ARQ-531, BMS-986142, dasatinib, ibrutinib, GDC-0853, PRN-1008, SNS-062, ONO-4059, BGB-3111, ML-319, MSC-2364447, RDX-022, X-022, AC-058, RG-7845, spebrutinib, TAS-5315, TP-0158, TP-4207, HM-71224, KBP-7536, M-2951, TAK-020, AC-0025, and the compounds disclosed in US20140330015 (Ono Pharmaceutical), US20130079327 (Ono Pharmaceutical), and US20130217880 (Ono Pharmaceutical).

KDM Inhibitors

Examples of KDM5 inhibitors include the compounds disclosed in WO2016057924 (Genentech/Constellation Pharmaceuticals), US20140275092 (Genentech/Constellation Pharmaceuticals), US20140371195 (Epitherapeutics), US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), and WO2014164708 (Quanticel).

Examples of KDM1 inhibitors include the compounds disclosed in U.S. Pat. No. 9,186,337B2 (Oryzon Genomics), GSK-2879552, RG-6016, and ORY-2001.

STING Agonists

Examples of STING agonists include SB-11285, AdVCA0848 and STINGVAX.

Examples of STING agonists include the compounds disclosed in WO 2018065360 ("Biolog Life Science Institute Forschungslabor und Biochemica-Vertrieb GmbH, Germany), WO 2018009466 (Aduro Biotech), WO 2017186711

(InvivoGen), WO 2017161349 (Immune Sensor), WO 2017106740 (Aduro Biotech), US 20170158724 (Glaxo Smithkline), WO 2017075477 (Aduro Biotech), US 20170044206 (Merck), WO 2014179760 (University of California), WO2018098203 (Janssn), WO2018118665 (Merck), WO2018118664 (Merck), WO2018100558 (Takeda), WO2018067423 (Merck), WO2018060323 (Boehringer).

Examples of Nonnucleoside Reverse Transcriptase Inhibitors (NNRTIs) include the compounds disclosed in WO2018118826 (Merck), WO2018080903 (Merck), WO2018119013 (Merck), WO2017100108 (Idenix), WO2017027434 (Merck), WO2017007701 (Merck), WO2008005555 (Gilead).

HBV Replication Inhibitors

Examples of hepatitis B virus replication inhibitors include isothiafludine, IQP-HBV, RM-5038, and Xingantie.

Arginase Inhibitors

Examples of Arginase inhibitors include CB-1158, C-201, and resminostat.

Gene Therapy and Cell Therapy

Gene Therapy and Cell Therapy including the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; and genetic approaches to modify cellular activity to further alter endogenous immune responsiveness against the infection.

Gene Editors

The genome editing system is selected from the group consisting of: a CRISPR/Cas9 system, a zinc finger nuclease system, a TALEN system, a homing endonucleases system, and a meganuclease system (e.g., an ARCUS system); e.g., cccDNA elimination via targeted cleavage, and altering one or more of the hepatitis B virus (HBV) viral genes. Altering (e.g., knocking out and/or knocking down) the PreC, C, X PreSI, PreS2, S, P or SP gene refers to (1) reducing or eliminating PreC, C, X PreSI, PreS2, S, P or SP gene expression, (2) interfering with Precore, Core, X protein, Long surface protein, middle surface protein, S protein (also known as HBs antigen and HBsAg), polymerase protein, and/or Hepatitis B spliced protein function (HBe, HBc, HBx, PreS1, PreS2, S, Pol, and/or HBSP or (3) reducing or eliminating the intracellular, serum and/or intraparenchymal levels of HBe, HBc, HBx, LHBs, MHBs, SHBs, Pol, and/or HBSP proteins. Knockdown of one or more of the PreC, C, X PreSI, PreS2, S, P and/or SP gene(s) is performed by targeting the gene(s) within HIBV cccDNA and/or integrated HBV DNA.

CAR-T Cell Therapy

CAR-T cell therapy includes a population of immune effector cells engineered to express a chimeric antigen receptor (CAR), wherein the CAR includes an HBV antigen-binding domain. In certain embodiments, the antigen-binding domain is a domain disclosed herein. In certain embodiments, the antigen-binding domain is other than a domain disclosed herein. The immune effector cell is a T-cell or an NK cell. In certain embodiments, the T-cell is a CD4+ T-cell, a CD8+ T-cell, or a combination thereof. Cells can be autologous or allogeneic.

TCR-T Cell Therapy

TCR-T cell therapy includes T cells expressing HBV-specific T cell receptors. TCR-T cells are engineered to target HBV derived peptides presented on the surface of virus-infected cells.

TCR-T cell therapy includes T-Cells expressing HBV surface antigen (HBsAg)-specific TCR.

TCR-T cell therapy includes TCR-T therapy directed to treatment of HBV, such as LTCR-H2-1.

In another specific embodiment, an anti-HBx antibody or antigen-binding fragment disclosed herein, or a pharmaceutically acceptable salt thereof, is combined with an HBV DNA polymerase inhibitor, one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2, and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In another specific embodiment, an anti-HBx antibody or antigen-binding fragment disclosed herein, or a pharmaceutically acceptable salt thereof, is combined with at least a second additional therapeutic agent selected from the group consisting of: HBV DNA polymerase inhibitors, immunomodulator, TLR modulators, HBsAg inhibitors, HBV therapeutic vaccines, HBV antibodies including HBV antibodies targeting the surface antigens of the hepatitis B virus and bispecific antibodies and "antibody-like" therapeutic proteins (such as DARPins®, anti-pMHC TCR-like antibodies, DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2.

In another specific embodiment, an anti-HBx antibody or antigen-binding fragment disclosed herein, or a pharmaceutically acceptable salt thereof, is combined with at least a second additional therapeutic agent selected from the group consisting of: HBV DNA polymerase inhibitors, HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein inhibitors).

In a particular embodiment, an anti-HBx antibody or antigen-binding fragment disclosed herein, or a pharmaceutically acceptable salt thereof, is combined with compounds such as those disclosed in U.S. Publication No. 2010/0143301 (Gilead Sciences), U.S. Publication No. 2011/0098248 (Gilead Sciences), U.S. Publication No. 2009/0047249 (Gilead Sciences), U.S. Pat. No. 8,722,054 (Gilead Sciences), U.S. Publication No. 2014/0045849 (Janssen), U.S. Publication No. 2014/0073642 (Janssen), WO2014/056953 (Janssen), WO2014/076221 (Janssen), WO2014/128189 (Janssen), U.S. Publication No. 2014/0350031 (Janssen), WO2014/023813 (Janssen), U.S. Publication No. 2008/0234251 (Array Biopharma), U.S. Publication No. 2008/0306050 (Array Biopharma), U.S. Publication No. 2010/0029585 (Ventirx Pharma), U.S. Publication No. 2011/

0092485 (Ventirx Pharma), US2011/0118235 (Ventirx Pharma), U.S. Publication No. 2012/0082658 (Ventirx Pharma), U.S. Publication No. 2012/0219615 (Ventirx Pharma), U.S. Publication No. 2014/0066432 (Ventirx Pharma), U.S. Publication No. 2014/0088085 (Ventirx Pharma), U.S. Publication No. 2014/0275167 (Novira Therapeutics), U.S. Publication No. 2013/0251673 (Novira Therapeutics), U.S. Pat. No. 8,513,184 (Gilead Sciences), U.S. Publication No. 2014/0030221 (Gilead Sciences), U.S. Publication No. 2013/0344030 (Gilead Sciences), U.S. Publication No. 2013/0344029 (Gilead Sciences), US20140275167 (Novira Therapeutics), US20130251673 (Novira Therapeutics), U.S. Publication No. 2014/0343032 (Roche), WO2014037480 (Roche), U.S. Publication No. 2013/0267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), US20100015178 (Incyte), US2016137652 (Flexus Biosciences, Inc.), WO2014073738 (Flexus Biosciences, Inc.), WO2015188085 (Flexus Biosciences, Inc.), U.S. Publication No. 2014/0330015 (Ono Pharmaceutical), U.S. Publication No. 2013/0079327 (Ono Pharmaceutical), U.S. Publication No. 2013/0217880 (Ono pharmaceutical), WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel), U.S. Pat. No. 9,186,337B2 (Oryzon Genomics), and other drugs for treating HBV, and combinations thereof.

In certain embodiments, an anti-HBx antibody or antigen-binding fragment disclosed herein, or a pharmaceutically acceptable salt thereof, is combined with 5-30 mg tenofovir alafenamide fumarate, tenofovir alafenamide hemifumarate, or tenofovir alafenamide. In certain embodiments, an anti-HBx antibody or antigen-binding fragment disclosed herein, or a pharmaceutically acceptable salt thereof, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide. In certain embodiments, an anti-HBx antibody or antigen-binding fragment disclosed herein, or a pharmaceutically acceptable salt thereof, is combined with 10 mg tenofovir alafenamide fumarate, tenofovir alafenamide hemifumarate, or tenofovir alafenamide. In certain embodiments, an anti-HBx antibody or antigen-binding fragment disclosed herein, or a pharmaceutically acceptable salt thereof, is combined with 25 mg tenofovir alafenamide fumarate, tenofovir alafenamide hemifumarate, or tenofovir alafenamide. An anti-HBx antibody or antigen-binding fragment as disclosed herein may be combined with the agents provided herein in any dosage amount of the compound (e.g., from 50 mg to 500 mg of compound) the same as if each combination of dosages were specifically and individually listed.

In certain embodiments, an anti-HBx antibody or antigen-binding fragment disclosed herein, or a pharmaceutically acceptable salt thereof, is combined with 100-400 mg tenofovir disoproxil fumarate, tenofovir disoproxil hemifumarate, or tenofovir disoproxil. In certain embodiments, an anti-HBx antibody or antigen-binding fragment disclosed herein, or a pharmaceutically acceptable salt thereof, is combined with 100-150; 100-200, 100-250; 100-300; 100-350; 150-200; 150-250; 150-300; 150-355; 150-400; 200-250; 200-300; 200-350; 200-400; 250-350; 250-400; 350-400 or 300-400 mg tenofovir disoproxil fumarate, tenofovir disoproxil hemifumarate, or tenofovir disoproxil. In certain embodiments, an anti-HBx antibody or antigen-binding fragment disclosed herein, or a pharmaceutically acceptable salt thereof, is combined with 300 mg tenofovir disoproxil fumarate, tenofovir disoproxil hemifumarate, or tenofovir disoproxil. In certain embodiments, an anti-HBx antibody or antigen-binding fragment disclosed herein, or a pharmaceutically acceptable salt thereof, is combined with 250 mg tenofovir disoproxil fumarate, tenofovir disoproxil hemifumarate, or tenofovir disoproxil. In certain embodiments, an anti-HBx antibody or antigen-binding fragment disclosed herein, or a pharmaceutically acceptable salt thereof, is combined with 150 mg tenofovir disoproxil fumarate, tenofovir disoproxil hemifumarate, or tenofovir disoproxil. An anti-HBx antibody or antigen-binding fragment as disclosed herein may be combined with the agents provided herein in any dosage amount of the compound (e.g., from 50 mg to 500 mg of compound) the same as if each combination of dosages were specifically and individually listed.

IX. Examples

The following examples are provided to better illustrate the disclosure and are not to be interpreted as limiting the scope of the disclosure. To the extent that specific materials are mentioned, it is merely for purposes of illustration and is not intended to limit the disclosure. One skilled in the art can develop equivalent means or reactants without the exercise of inventive capacity and without departing from the scope of the disclosure.

Example 1. Inhibition of Hepatitis B Virus X Protein Leads to the Reappearance of the Smc5/6 Complex in HBV-Infected Primary Human Hepatocytes Summary The host structural maintenance of chromosome 5/6 complex (Smc5/6) suppresses cccDNA transcription (Decorsière A, et al. Nature 2016; 531:386-9; 2. Murphy C, et al. Cell Rep 2016; 16:2846-54). HBV counters this restriction by expressing HBx, which redirects the cellular DDB1-containing E3 ubiquitin ligase to target Smc5/6 for degradation (Decorsière A, et al. Nature 2016; 531:386-9; 2. Murphy C, et al. Cell Rep 2016; 16:2846-54). HBx is an attractive therapeutic target because inhibition of this key viral protein has the potential to transcriptionally silence cccDNA. However, it is challenging to evaluate the impact of different therapeutic approaches on this important viral protein due to the lack of a highly specific HBx antibody. The disclosures below describe the spatiotemporal analysis of HBx in HBV-infected primary human hepatocytes (PHH) using a novel monoclonal antibody. An additional objective is to determine if various therapeutic approaches reduce HBx levels.

Recombinant proteins and HepG2 cells transduced with a lentivirus expressing HBx were analyzed by Western blot. PHH were infected with wild-type HBV, HBx-negative HBV (HBVΔX), or were mock-infected. In certain experiments, PHH were transfected with siRNA targeting DDB1 (siDDB1), the HBx region of HBV RNA (siHBV) or a non-targeting control (siCtrl) at day 3 post-infection. HBx, HBV core, Hepatitis B s antigen (HBsAg) and Smc6 were measured by confocal microscopy at various times post-infection.

An antibody that selectively detects recombinant HBx as well as HBx over-expressed in HepG2 cells was selected for confocal imaging studies. HBx exhibited a diffuse nuclear staining pattern in HBV-infected PHH and was not detected in the cytoplasm. Nuclear HBx positively correlated with HBV core and HBsAg and inversely correlated with the presence of Smc6. HBx was not detected in PHH infected with HBVΔX. Consistent with a previous study that characterized the kinetics of Smc6 degradation in HBV-infected PHH, HBx was expressed 2 days after infection. Cycloheximide studies revealed that HBx, but not HBV core, has a very short half-life in HBV-infected PHH. Treatment with siHBV (which reduces all HBV RNAs, including HBx mRNA) and siDDB1 (which blocks HBx function) decreased HBx levels and was associated with the reappearance of Smc6 in the nuclei of HBV-infected PHH over time.

Using a novel monoclonal antibody, it was demonstrated that HBx is localized to the nucleus and is expressed early after HBV infection of PHH. It was also determined that reduction of HBx protein levels in HBV-infected PHH by siRNA treatment leads to the reappearance of Smc6. These data suggest that cccDNA transcriptional silencing by the Smc5/6 complex may be restored by therapeutic approaches that reduce HBx levels or inhibit HBx function.

Methods

Reagents

The HepAD38 and the HepG2-H1.3x-stable cell lines have been described (Lucifora, et al., *J Hepatol* (2011) 55:996-1003, Ladner, et al., *Antimicrob Agents Chemother* (1997) 41:1715-20) and were obtained from Avid Therapeutics and Ulrike Protzer, respectively. Cryopreserved PHH isolated from deceased donor livers were purchased from Life Technologies (Grand Island, N.Y.). Consent was obtained from the donor or the donor's legal next of kin for use of these samples and their derivatives for research purposes using IRB-approved authorizations. Rabbit polyclonal anti-HBV core (Agilent, Santa Clara, Calif.), rabbit monoclonal anti-HBV core (clone 366-2) (Gilead Sciences, Foster City, Calif.), rabbit polyclonal anti-Smc6 (MilliporeSigma, St. Louis, Mo.), mouse monoclonal anti-Smc6 (M01) (Abgent, San Diego, Calif.), rabbit monoclonal anti-HBsAg (ViroStat, Westbrook, Me.), mouse monoclonal anti-Myc (9E10) (LifeSpan Biosciences, Inc., Seattle, Wash.), rabbit anti-GAPDH (14C10) (Cell Signaling, Danvers, Mass.) were used for Western blotting and confocal imaging. Alhydrogel (ALD; InvivoGen, San Diego, Calif.) and muramyl dipeptide (MDP; MilliporeSigma) were used as an adjuvant for mouse immunizations. Entecavir was purchased from Selleck Chem (Houston, Tex.). All lentiviruses were produced by System Biosciences (Palo Alto, Calif.). All siRNAs were obtained from Dharmacon (Boulder, Colo.). The HBV (siHBx 1 and siHBx2), DDB1 (siDDB1) and control (siCtrl1) siRNAs have been previously described (Decorsière, et al., *Nature* (2016) 531:386-389, Shin, et al., *Virus Res* (2006) 119:146-53). In the original description, siHBx 1 was referred to as "HBx-1" and siHBx2 was referred to as "HBx-3" (Shin, et al., *Virus Res* (2006) 119:146-53). The primers and probes for quantitative PCR (qPCR) were synthesized by IDT (Coralville, Iowa) (HBV) and Life Technologies (β-actin).

Monoclonal Antibody Production

Mouse monoclonal anti-HBx antibodies were developed by Antibody Solutions (Sunnyvale, Calif.). Antibody candidates were screened by enzyme-linked immunosorbent assay (ELISA) using recombinant HBx-DDB1 fusion protein and then by confocal microscopy on HBV infected PHH.

Five peptide sequence of approximately 20 residues in length spanning various region on HBx (excluding the HBx-DDB1 interacting region) were analyzed for solubility, secondary structure as well as antigenic potential using established methods (Hopp, et al., *Proc Natl Acad Sci USA* (1981) 78:3824-8; Parker, et al., *Biochemistry* (1986) 25:5425-32). Two of these HBx peptides were individually conjugated to BSA and three NZB/W, three CD-1, and three BALB/c mice were immunized with 10 g peptide-BSA conjugate plus 1 g adjuvant (ALD and MDP in a 1:1 ratio). Biweekly injections were performed using a "rapid" immunization protocol developed by Antibody Solutions. The HBx AD38 (genotype D) residue 27-50 peptide (HBx27-50) was immunogenic in CD-1 mice and the resulting hybridomas were evaluated for binding to recombinant HBx-DDB1 fusion protein by ELISA. The top 50 candidates were further evaluated by confocal imaging of HBV-infected PHH. Monoclonal antibodies (mAb) were developed from the two most selective and sensitive hybridoma clones (M14 and M19). The top antibody clone (M19) was selected after Western blot analysis of lentivirus-expressed HBx in PHH.

To generate a rabbit anti-HBx antibody, the variable domain of the heavy (VH) and light (VL) chain of the mouse HBx antibody were PCR amplified with primers encompassing 15 nucleotide overhangs to the rabbit immunoglobulin heavy and kappa constant region coding sequence. The VH and VL PCR bands were gel extracted using the QIAquick Gel extraction kit (Qiagen, Valencia, Calif.) and cloned into the pcDNA3.1 expression vector with the rabbit immunoglobulin heavy and kappa constant PCR band, respectively, using InFusion® HD Cloning kit (Takara Bio USA, Mountain View, Calif.). The heavy and light chain expression plasmids were then transfected into Expi293F™ cells following the manufacturer's protocol (ThermoFisher Scientific, Waltham Mass.). Four days post-transfection, the cells were pelleted by centrifugation and the media was collected. The rabbit anti-HBx antibody was purified from the media by Protein A chromatography.

HBx ELISA

Antibody candidates were screened by ELISA. Briefly, sulfhydryl plates were coated with 36 ng/mL recombinant HBx-DDB1 fusion protein, blocked and then incubated with 50 µL of undiluted hybridoma supernatant. Signal was detected colorimetrically with a goat anti-mouse-HRP antibody (Jackson Immuno Research, West Grove, Pa.) and incubation with TMB substrate solution (MossBio, Pasadena, Mass.). Signal strength was measured as absorbance at 450 nM. ELISA profiling of mAbs was performed using 100 ng/mL antibody with varying concentrations of recombinant HBx-DDB1 fusion protein or HBx peptide.

HBV Virion Production and PHH Infection

HBV preparations were generated by PEG-concentrating supernatant from HepAD38 cells (which produce wild-type HBV) or HepG2-H1.3x cells (which produce HBVΔX virus due to an early stop codon in the HBx gene) (Lucifora, J et al. J Hepatol 2011; 55:996-1003).

Production of wild-type HBV virions (genotype D) from HepAD38 cells and HBVΔX virions (genotype D) from the HepG2-H1.3x-stable cell line was performed as previously described (Decorsière, et al., *Nature* (2016) 531:386-389, Niu, et al., *PLoS One* (2017) 12:e0169648). PHH were infected with HBV or HBVΔX (1000 genomic equivalents/cell) or transduced with lentiviruses as described previously (Niu, et al., *PLoS One* (2017) 12:e0169648).

siRNA transfections were performed using Lipofectamine RNAiMax. For the RNA interference studies, PHH were transfected with 25 nM siRNA using Lipofectamine RNAiMax (ThermoFisher Scientific) according to the manufacturer's instructions.

Western Blotting

For Western blotting experiments, PHH were transduced with Myc-HBx-expressing lentivirus or were infected with wild-type HBV, HBx-negative HBV (HBVΔX), or were mock-infected.

Rabbit polyclonal anti-Core (Agilent), rabbit polyclonal anti-Smc6 (Sigma Aldrich), rabbit monoclonal anti-HBsAg (Virostat), and mouse monoclonal anti-Myc (LifeSpan Biosciences) were used for Western blotting and confocal microscopy.

Western blotting was performed as previously described (Decorsière, et al., *Nature* (2016) 531:386-389). Briefly, PHH were transduced with a lentivirus expressing 3×Myc-HBx (HBV genotype A, B, C, D or E) or infected with wild-type HBV, HBVΔX, or mock-infected. On the indicated day post-transduction or post-infection, lysates were collected by adding 0.25 mL 1× cell lysis buffer (Cell Signaling) combined with protease inhibitor cocktail (ThermoFisher Scientific) and scraping to remove the cells from the plates. Membranes were probed with 1:250 diluted mouse monoclonal anti-Smc6 (Abgent), 1:1000 diluted mouse monoclonal c-Myc (LifeSpan Biosciences), 1:250 diluted mouse monoclonal anti-HBx mAb (15 µg/mL final concentration), and 1:2000 diluted rabbit monoclonal anti-GAPDH (Cell Signaling). IRDye 680RD goat anti-rabbit or IRDye 800CW goat anti-mouse IgG (LI-COR, Lincoln, Nebr.) at a 1:5000 dilution were used as secondary antibodies. Blots were visualized using an Odyssey Infrared Imaging System (LI-COR).

Confocal Microscopy

PHH were seeded onto glass coverslips (Corning BioCoat Poly-D-Lysine/Laminin 12 mm, Corning, N.Y.) in 12-well Corning Cellbind plates and were infected or transduced on the following day. On the indicated day post-infection or post-transduction, cells were fixed for 10 minutes using Perfusion Fixative Reagent (ThermoFisher Scientific) and washed three times in Dulbecco's Phosphate-Buffered Salt Solution (DPBS) (Corning). All steps of the immunostaining protocol were performed at room temperature. Cells were then permeabilized in 0.3% Triton X-100 (MilliporeSigma) for 15 minutes following by blocking in DPBS with 3% bovine serum albumin (BSA) (MilliporeSigma) and 10% HyClone Fetal Bovine Serum (FBS) (MilliporeSigma) for 60 minutes. The final concentrations of primary antibodies were 0.2 µg/mL for mouse anti-HBx mAb, 1 µg/mL for rabbit anti-HBx mAb, 1 g/mL for rabbit anti-Smc6 (MilliporeSigma), 1 µg/mL for mouse anti-Smc6 (Abgent), 1:500 dilution for rabbit anti-HBsAg antibody (ViroStat), 0.5 µg/mL for rabbit anti-HBV core antibody (Gilead Sciences), 1:1000 dilution for rabbit anti-HBV core antibody (Agilent). Secondary antibodies conjugated with either Alexa Fluor 488 (goat anti-rabbit IgG, ThermoFisher Scientific) or Alexa Fluor 647 (donkey anti-mouse IgG (H+L), ThermoFisher Scientific) were used at 2 µg/mL. All antibodies were diluted in DPBS containing 1.5% BSA. Primary and secondary antibodies were applied for 90 minutes and 60 minutes, respectively. The coverslips with stained cells were mounted on the glass microscopic slides (VWR International, Radnor, Pa.) with a drop of ProLong Gold antifade reagent containing DAPI (ThermoFisher Scientific). The samples were imaged with confocal laser scanning microscope Leica SP8 (Leica Microsystems Inc., Wetzlar, Germany). All images within each sample set were captured using identical instrument settings. The acquisition was performed in two sequences to minimize bleed-through artifacts. During the first sequence, DAPI was excited at 405 nm with UV laser and detected at 415-494 nm while Alexa Fluor 647 was excited at 647 nm and detected at 657-800 nm. During the second sequence, Alexa Fluor 488 was excited at 499 nm and detected at 504-648 nm. Lentivirus-expressed HBx was stained with Alexa Fluor 555 due to the presence of GFP in the construct. In this case, the detection was performed in three sequences by adding a sequence to measure Alexa Fluor 555 signal by exciting the fluorophore at 555 nm and detecting the fluorescence at 565-640 nm.

The percentage of cells expressing proteins of interest were quantified using Imaris Image Analysis Software.

The images were analyzed with Image J 1.51u (NIH, Bethesda, Md.). Batch processing to identify cells positive for HBx, Smc6, nuclear HBV core or HBsAg was performed with image analysis software Imaris 9.1.2 (Bitplane, Belfast, UK) using algorithm based on Cell Detection function (smooth filter width: 0.0401 µm, diameter of seed points: 5 µm). The HBx, HBV core and HBsAg background was calculated as the mean+2×standard deviations of the background signal in mock-infected PHH. The Smc6 background was calculated as the mean−2×standard deviations of the Smc6 level in mock-infected PHH. Values above these limits were considered positive and values below were considered negative. For HBx, HBV core and Smc6 proteins in HBV-infected PHH, these measurements were restricted to nucleoplasm defined by DNA staining with DAPI. For lentivirus-expressed HBx, the average intensity of cytoplasmic and nuclear fluorescence signal was determined using ImageJ by manually selecting the corresponding areas (based on nuclear staining, cell edges and excluding regions with staining artifacts). For visualization of the spatial localization of HBx and Smc6 within a nucleus, a series of Z-stacks was acquired with the step of 200 nm (the pixel size was 50.1 nm) and volumetric rendering was performed using Imaris 9.1.2 by defying the boundaries of the objects and applying Surfaces function. Images were adjusted equally within each data set for brightness and contrast using PowerPoint 2010 (Microsoft, Redmond, Wash., USA).

Protein Stability Assay

PHH were infected with HBV as described previously (Niu, et al., *PLoS One* (2017) 12:e0169648). At day 5 post-infection, 100 µg/mL cycloheximide was added to stop protein translation. The cells were then fixed as described above at various times post-cycloheximide addition. Protein signal intensity was measured by confocal imaging and normalized to a signal obtained for an untreated sample fixed simultaneously. The data were plotted as percentage initial signal vs. time (hours) post-cycloheximide addition and fit to a first-order exponential decay equation ($[A]=[A]0 e^{(-kt)}$) using GraphPad Prism version 7.03 (GraphPad Software, San Diego, Calif.) to calculate the decay constant $(-k)$. The half-life for each protein $(t_{1/2})$ was calculated in hours using $\ln 2/k$.

Extracellular HBeAg and HBV DNA Quantification

Extracellular HBeAg and HBV DNA were measured as previously described (Niu, et al., *PLoS One* (2017) 12:e0169648, 29). HBeAg levels were measured by enzyme-linked immunosorbent assay or electrochemiluminescence assay (Meso Scale Discovery, Rockville, Md.).

Extracellular HBV DNA was purified from cell-culture medium using a DNeasy 96 Blood & Tissue Kit (Qiagen) and quantified by qPCR on a QuantStudio 7 Flex Real-Time PCR System (ThermoFisher Scientific) using primers and a probe designed to the HBx region of the HBV genome; forward primer: 5'-CCG TCT GTG CCT TCT CAT CTG-3'; reverse primer: 5'-AGT CCA AGA GTY CTC TTA TGY AAG ACC TT-3'; probe: 5/56-FAM/CCG TGT GCA/ZEN/ CTT CGC TTC ACC TCT GC/3IABkFQ/3'. HBV DNA levels were normalized to β-actin.

Statistical Analysis

Data is expressed as mean standard error of the mean (SEM). Statistical significance was tested using a two-tailed t-test (for two sample comparisons) or one-way ANOVA with multiple comparison correction (for multiple comparisons) using GraphPad Prism version 7.03 (GraphPad Software). A value of $p<0.05$ was considered significant.

Results

Development and Validation of a Novel HBx Antibody

Figures 2A, 2B:
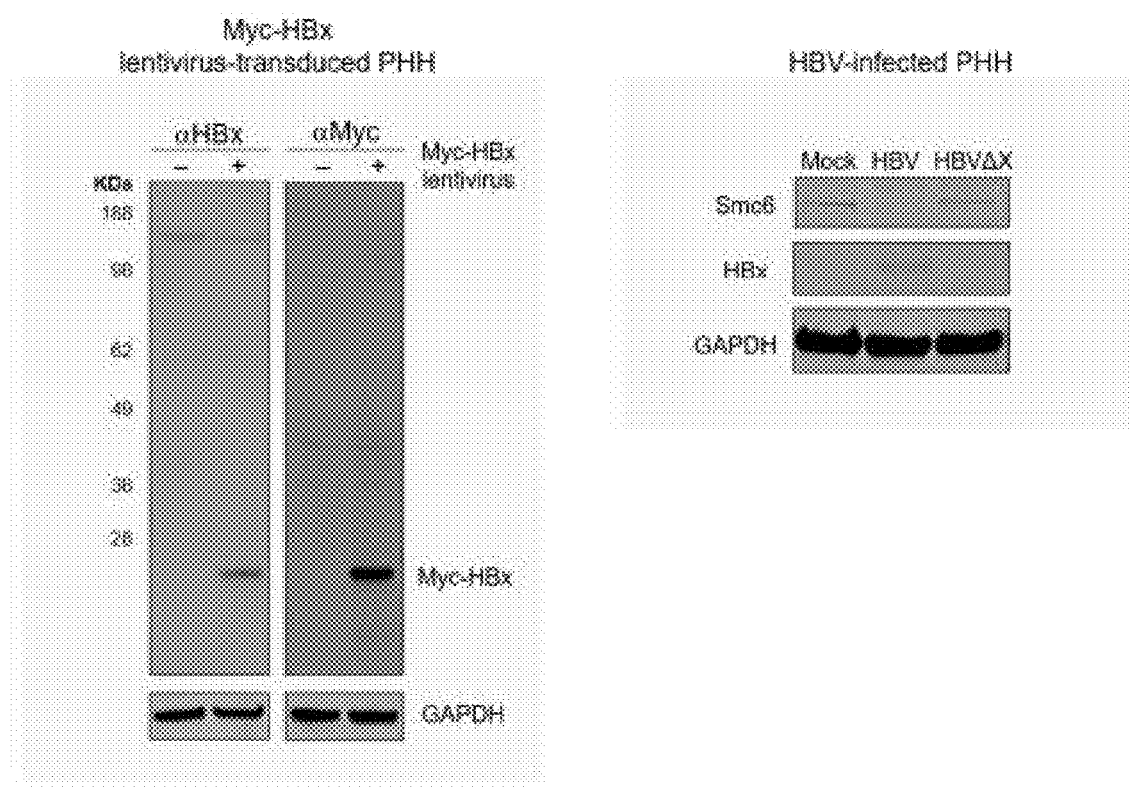

A novel monoclonal antibody against HBx (αHBx mAb; HBx M19) was developed. The αHBx mAb detected HBx by Western blot in PHH transduced with a Myc-HBx lentivirus (FIG. 2A) as well as in HBV-infected PHH (FIG. 2B).

In order to perform a spatiotemporal analysis of HBx in HBV-infected PHH, we first developed a highly-specific and sensitive HBx monoclonal antibody (mAb). Mice were immunized with a peptide corresponding to genotype D HBx residues 27-50 (HBx27-50) and the resulting hybridomas evaluated by ELISA and confocal microscopy. The two hybridoma clones with the best signal-to-noise ratio (as measured by confocal imaging) were selected for monoclonal antibody production. The top mAb was chosen because it displayed superior sensitivity in a Western blot analysis. This anti-HBx mAb potently bound the HBx27-50 peptide but did not bind the HBx69-87 control peptide (FIG. 2C). This antibody also bound a recombinant HBx-DDB1 fusion protein (FIG. 2C). Binding to this protein is notable because we have found that HBx adopts a physiologically relevant conformation when expressed in this context.

The HBx mAb was subsequently evaluated by Western blotting. The antibody detected a 17 kDa protein (the predicted size of Myc-HBx) in lysates from PHH transduced with a lentivirus expressing Myc-tagged HBx (genotype D) (FIG. 2A). This band was confirmed to be HBx using a Myc antibody (FIG. 2A). Consistent with substantial inter-genotype sequence variation in the HBx27-50 sequence (FIG. 2D), we determined that the HBx mAb primarily recognizes genotype D HBx (FIG. 2E). Accordingly, genotype D HBV was used for all subsequent studies. We next demonstrated that the HBx mAb detects a 17 kDa band in lysate from HBV-infected PHH, but not in lysate from mock-infected or HBx negative virus (HBVΔX)-infected PHH (FIG. 2B). Smc6 levels were only reduced in HBV-infected PHH, consistent with expression of functional HBx protein (FIG. 2B). Collectively, these data demonstrate that the anti-HBx mAb is selective for genotype D HBx, and is able to detect physiologically relevant levels of HBx protein in the context of natural infection.

HBx Localizes to the Nucleus of HBV-Infected Hepatocytes

Figure 3A:
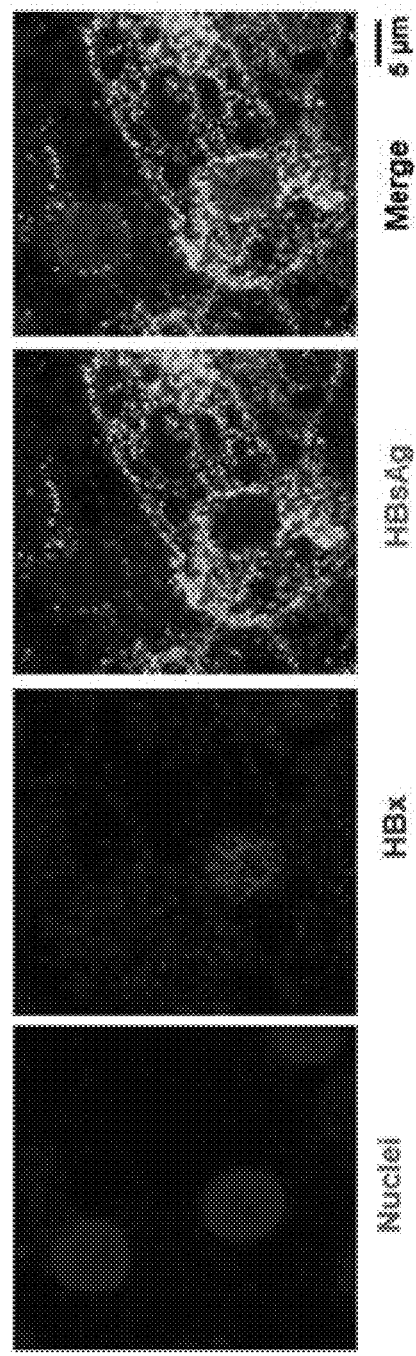
FIGS. 3A and 3B illustrate that HBx positively correlates with HBsAg and HBV core in HBV-infected PHH. Depicted are fluorescence microscopy images showing that HBx exhibits a diffuse nuclear staining pattern in HBV-infected PHH. PHH were infected with HBV for 13 days. PHH were infected with HBV and analyzed by confocal microscopy at day 13 post-infection. PHH were stained for HBx (red), (A) HBsAg (green) or (B) HBV core (green). Nuclei were stained with DAPI (blue).
Figure 3B:
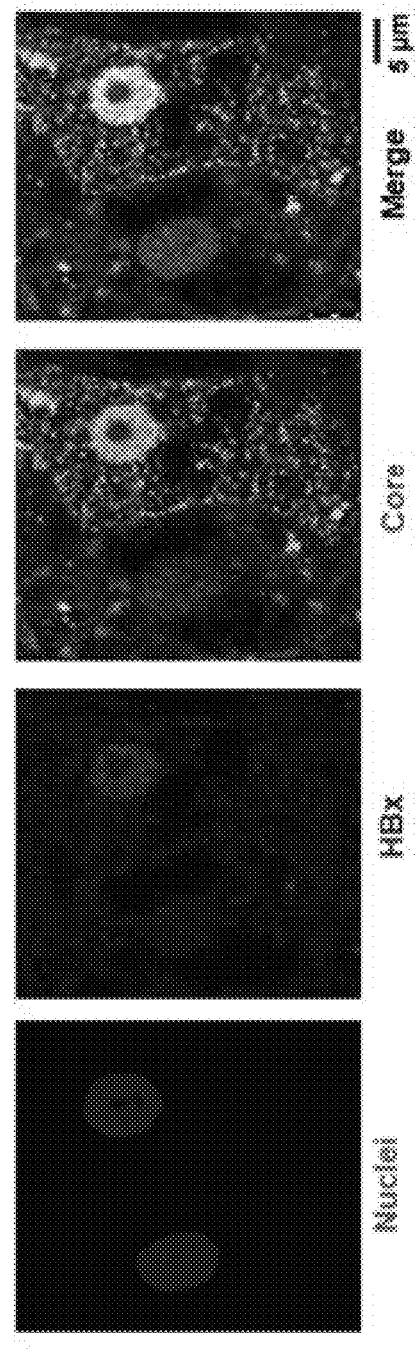
Figure 4A:
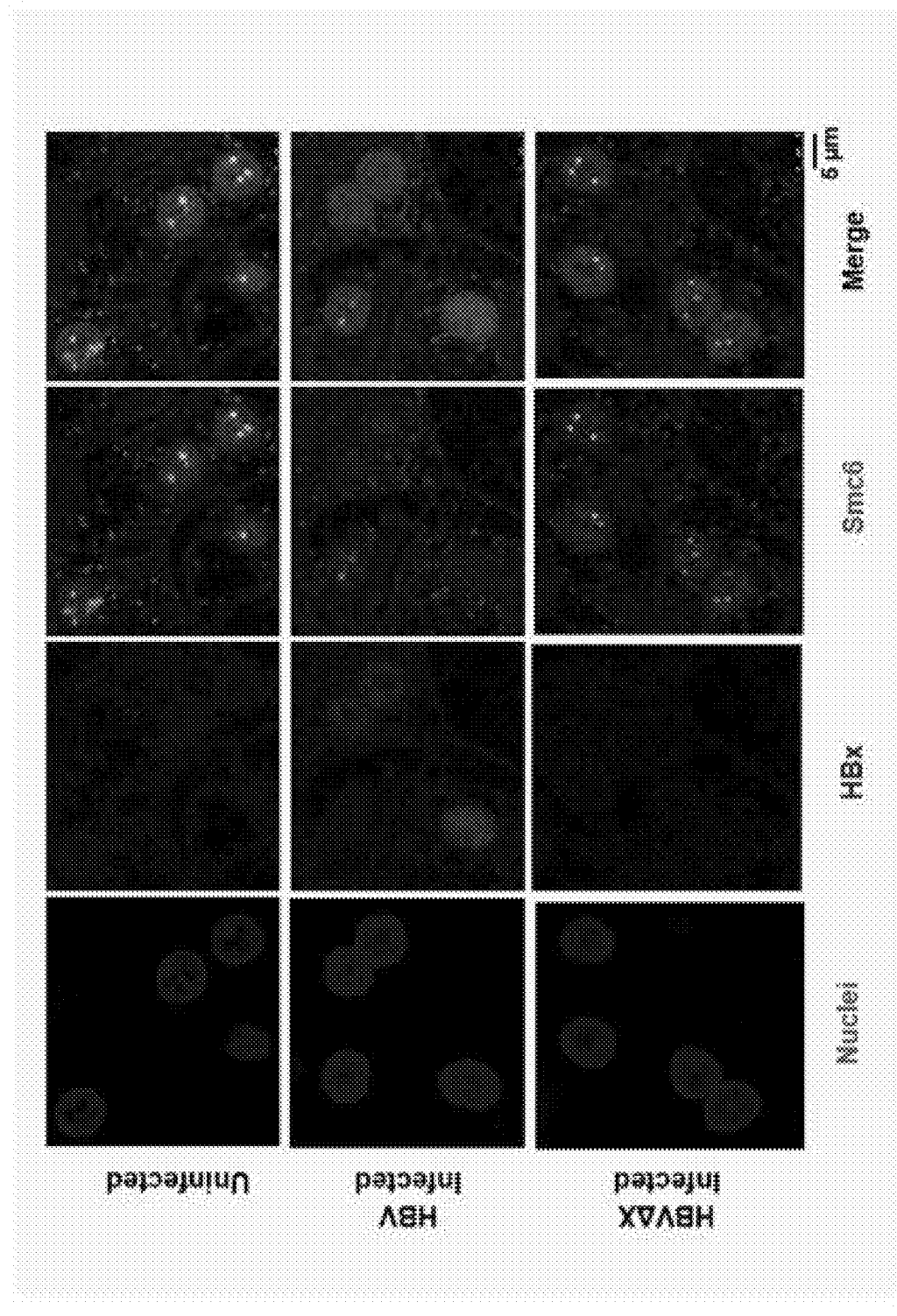
FIGS. 4A-4B illustrate that HBx localizes to the nucleus and inversely correlates with Smc6 in HBV-infected PHH. Depicted is a set of fluorescence microscopy images

HBx exhibited a diffuse nuclear staining pattern in HBV-infected PHH and was not detected in the cytoplasm (FIG. 3). Nuclear HBx positively correlated with the presence of HBV core (FIGS. 3B and 5A) and HBsAg (FIGS. 3A and 5B) and negatively correlated with Smc6 (FIGS. 4 and 5C). HBx was not detected in PHH infected with HBVΔX (FIG. 4A).

Figure 4B:
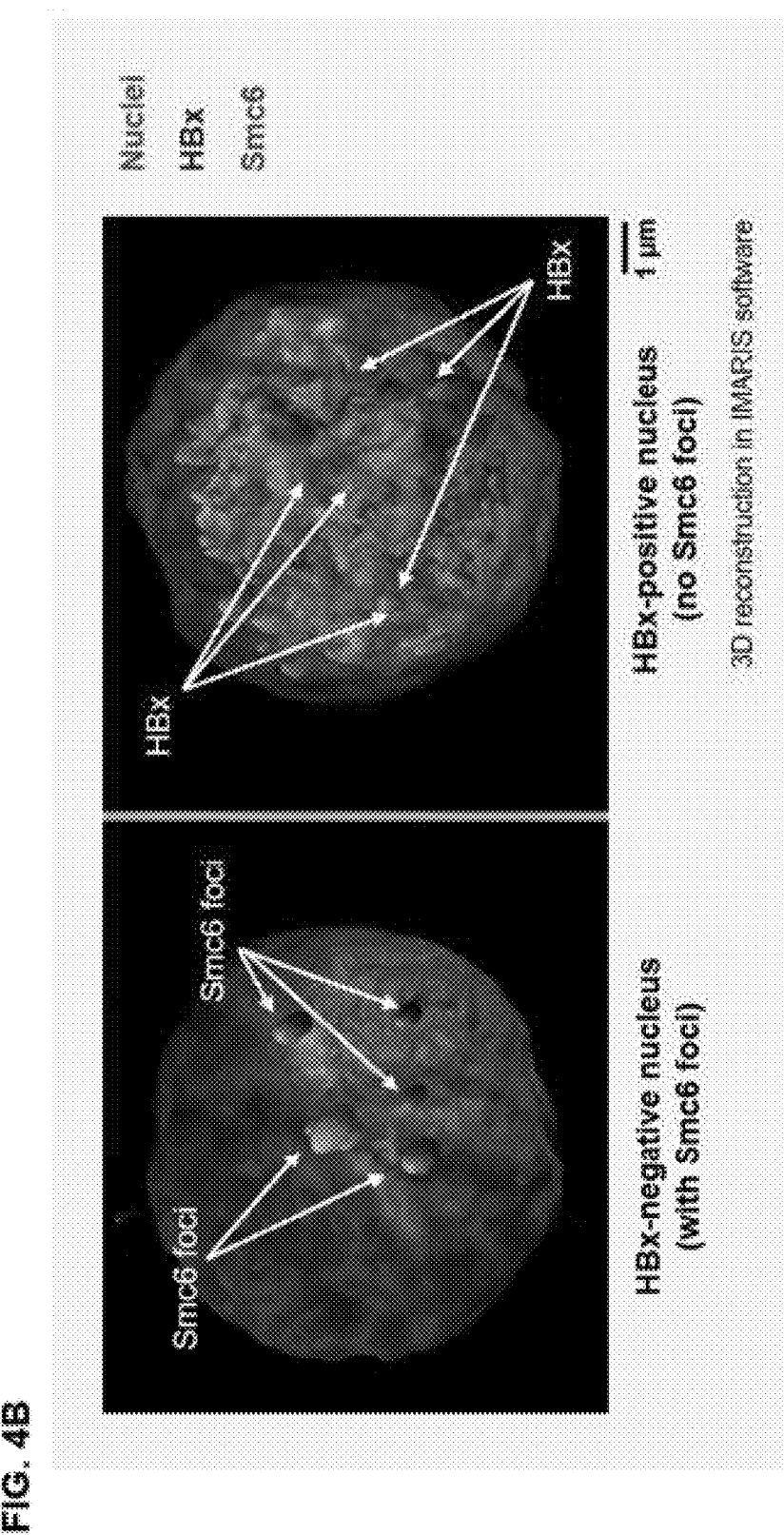

After confirming the selectivity of the HBx mAb by ELISA and Western blot, we used this new reagent to evaluate the spatial distribution of HBx in a natural infection system. In HBV-infected PHH, single cell analysis revealed that HBx is predominantly located in the nucleus where it exhibits a diffuse staining pattern (FIGS. 4A and 4B). HBx was not detected in PHH that were mock-infected or infected with an HBx-negative virus (HBVΔX) (FIG. 4A). The presence of HBx inversely correlated with the presence of Smc6 (FIG. 4A). Consistent with previous studies (Decorsière, et al., *Nature* (2016) 531:386-389, Niu, et al., *PLoS One* (2017) 12:e0169648), almost all the uninfected PHH were Smc6-positive, whereas the majority of HBV-infected PHH were Smc6-negative and HBx-positive (FIG. 5C). There was good concordance between the percentage of HBV-infected PHH that were Smc6-negative (92%) and those that were HBx-positive (85%). HBx expression positively correlated with the presence of both HBsAg and HBV core in HBV-infected PHH (FIGS. 3A and 5A-B), although there was superior concordance between HBx and core than between HBx and HBsAg (FIGS. 5A-B). This is in line with previous studies comparing Smc6, core and HBsAg levels in HBV-infected PHH (Niu, et al., *PLoS One* (2017) 12:e0169648).

HBx is Expressed Early after HBV Infection

Figure 6:
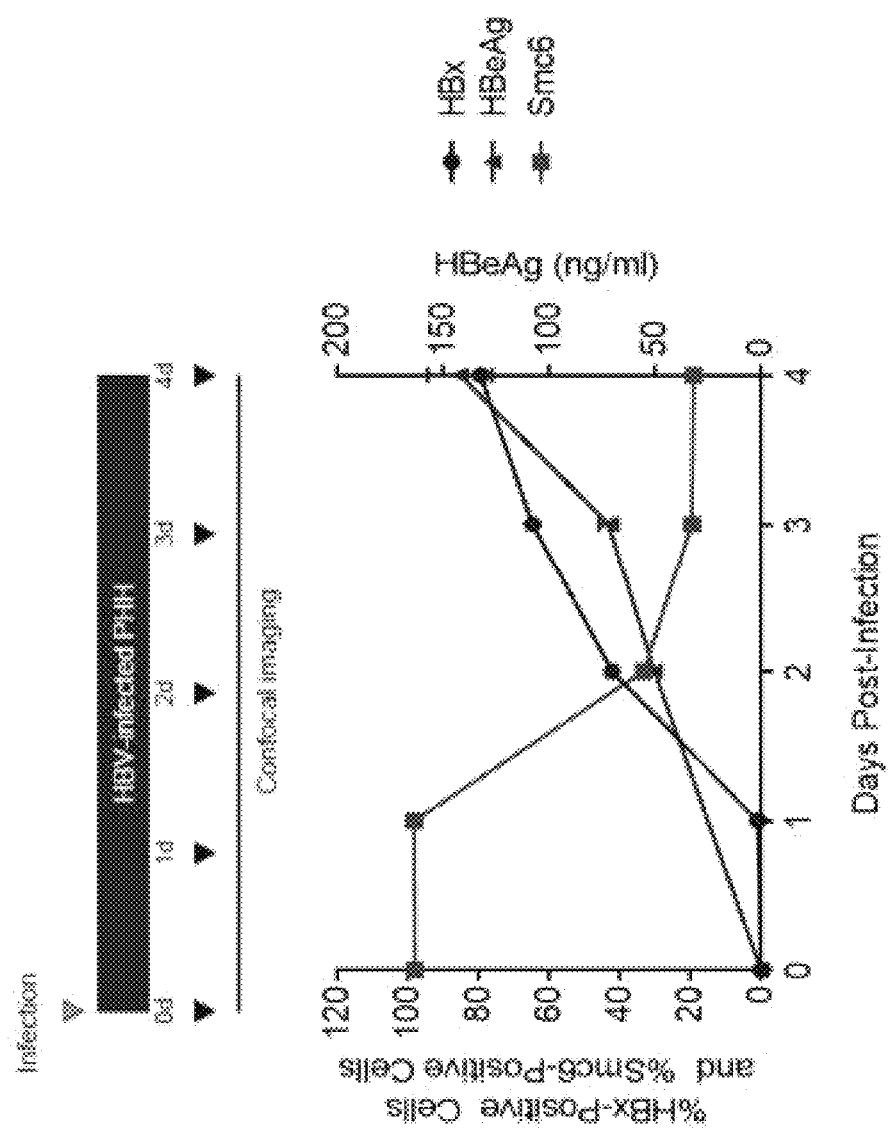
FIG. 6 illustrates that HBx is expressed shortly after HBV infection and has a short half-life in PHH. Depicted is a graph showing temporal changes in intracellular HBx and Smc6 and extracellular HBeAg levels after HBV infection. PHH were fixed on various days post-infection with HBV. The percentage of cells positive for each protein was determined by confocal microscopy (n≥100 cells for each condition). HBeAg levels were measured by MSD on various days post-infection with HBV. PHH were infected with HBV and nuclear HBx and Smc6 mean fluorescence intensity levels were measured on the indicated days post-infection by confocal microscopy. HBeAg levels were measured by MSD on the indicated days post-infection. HBV core and Smc6 status of HBV-infected PHH was determined using background levels calculated from time-matched mock-infected controls.

Consistent with a previous study that characterized the kinetics of Smc6 degradation in HBV-infected PHH (Niu et al. PLoS One 2017; 12: e0169648), HBx was expressed 2 days after infection (FIG. 6). As expected, viral antigen production displayed slower kinetics, with substantial HBeAg (>100 ng/mL) detected from day 4 post-infection (FIG. 6).

In Niu, et al., we reported that HBx is expressed early after HBV infection using Smc6 degradation as a functional read-out of HBx expression (Niu et al., supra). However, we were unable to directly measure the kinetics of HBx expression in these prior experiments. We therefore performed a series of imaging studies to characterize the kinetics of HBx expression in HBV-infected PHH. This revealed that a few HBx-positive cells could be detected at 24 hours post-infection, with the percentage of HBx-positive cells increasing rapidly thereafter (FIG. 6). In line with our previous study, the percentage of Smc6-positive cells sharply declined by day 2 post-infection (FIG. 6). Interestingly, there were more Smc6-negative cells (80%) than HBx-positive cells (40%) at day 2 post-infection, whereas there was good concordance between these measures on days 3 and 4 post-infection. These data suggest that very low levels of HBx (i.e. below the detection limit of this assay) are able to target Smc6 for degradation.

HBx has a Short Half-Life in HBV-Infected PHH

HBx, but not HBV core, has a short half-life in HBV-infected PHH (FIG. 7).

The half-life of HBx has been evaluated in various experimental systems (Henkler, et al., *J Gen Virol* (2001) 82:871-82; Hoare, et al., *J Med Virol* (2001) 64:419-26; Schek, et al., *Oncogene* (1991) 6:1735-44), but never in the context of natural infection. In order to do so, the levels of HBx and core protein in the nucleus of HBV-infected PHH were measured by confocal microscopy at various times after treatment with the translation inhibitor cycloheximide. This revealed that HBx has a half-life of approximately 3 to 4.5 hours in HBV-infected PHH (FIG. 7A). In contrast, nuclear HBV core was extremely stable with a half-life greater than 24 hours (FIG. 7B).

The HBx half-life in HBV-infected PHH is relatively short given that some proteins in PHH have half-lives on the order of days (Mathieson, et al., *Nature Communications* (2018) 9:689). In light of this short half-life, the observation that HBx was detected in HBV-infected PHH at 13-21 days post-infection suggests that HBx is continuously expressed after infection. This is consistent with the requirement for HBx for both the initiation and maintenance of HBV replication after infection (Lucifora, et al., *J Hepatol* (2011) 55:996-1003). DDB1 is also required for HBV replication, by virtue of its role in HBx function (Decorsière, et al., *Nature* (2016) 531:386-389, Li, et al., *Nat Struct Mol Biol* (2011) 17:105-11). It was reported that HBx is stabilized by the interaction with DDB1 in Chang cells (Bergametti, et al., *J Virol* (2002) 76:6495-501). Our observation that the cellular localization of HBx is influenced by the interaction with DDB1 provides a potential explanation for why DDB1 binding alters HBx stability.

Reducing HBV mRNA or Inhibiting HBx Function Decreases HBx Protein Levels and Leads to Reappearance of Smc6 in HBV-Infected Hepatocytes Treatment with siHBV (which reduces all HBV RNAs, including HBx mRNA) (FIGS. 8 and 10) and siDDB1 (which blocks HBx function) (FIGS. 9 and 10) decreased HBx levels and was associated with the reappearance of Smc6 in the nuclei of HBV-infected PHH over time.

A number of siRNAs are currently in preclinical and clinical development for the treatment of CHB (Gish, et al., *Antiviral Res* (2015) 121:97-108; Schinazi, et al., *Liver Int* (2018) 38 Suppl 1:102-114). Inhibiting HBx by RNA interference is a promising therapeutic strategy since restoration of Smc5/6 should lead to transcriptional silencing of cccDNA. In addition, since the HBx mRNA sequence is co-terminal with all other HBV RNAs, an siRNA trigger in HBx mRNA should target all HBV RNAs for degradation. However, the overlap of the HBV RNA sequences precludes the selective detection of HBx mRNA by qRT-PCR. Moreover, it is very challenging to measure HBx mRNA levels by Northern Blot (Niu et al. PLoS One 2017; 12: e0169648). Therefore, while it is widely expected that HBx siRNA treatment would reduce HBx levels, it has never (to our knowledge) been directly demonstrated.

Figure 8A:
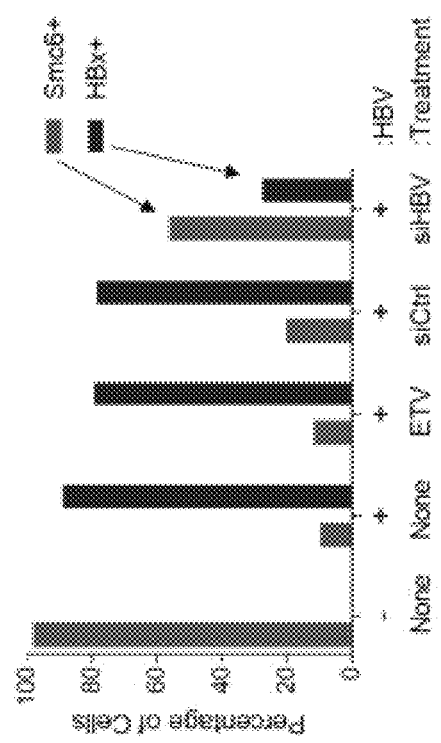
FIGS. 8A and 8B are graphs showing that siHBV (also called siHBx1 herein) treatment reduces HBx levels. PHH were treated with ETV (160 pM), siHBV, or a non-targeting siRNA control (siCtrl) from days 6 through 17 post-infection. Extracellular HBV DNA levels were measured 17 days post-infection. The percentage of PHH positive for HBx and Smc6 at day 17 post-infection was determined by confocal microscopy (n≥112 cells per condition).
Figure 8B:
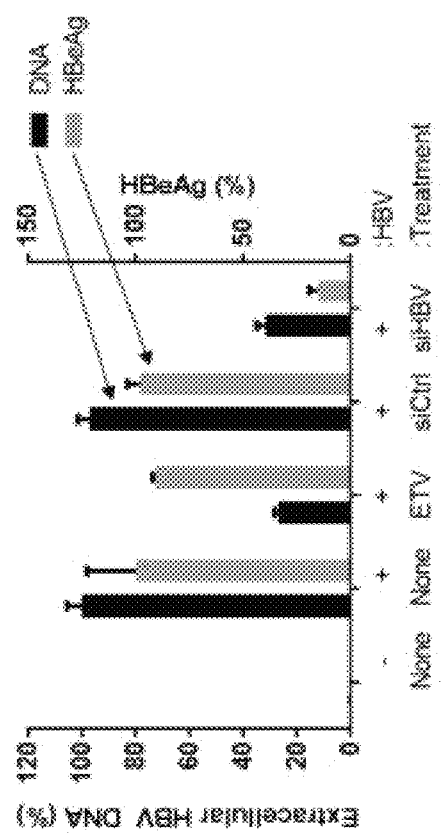
Figure 10A:
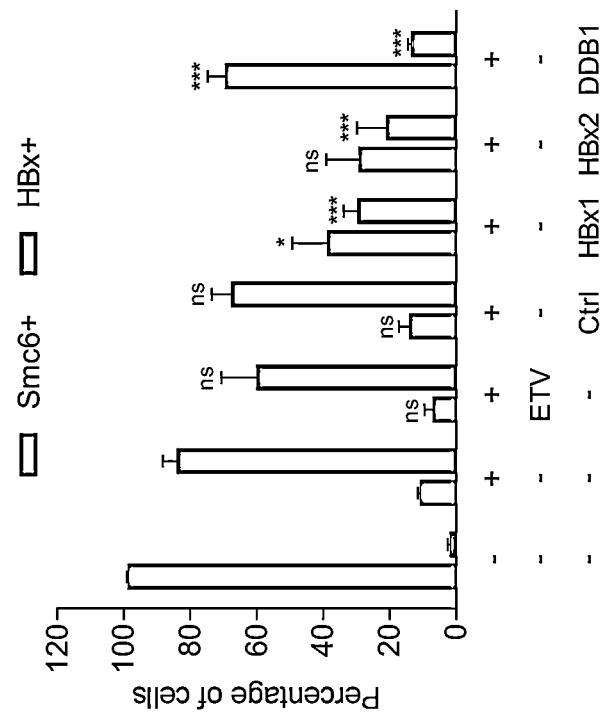
FIGS. 10A and 10B illustrate inhibition of HBx and reappearance of Smc6 after treatment of HBV-infected PHH with siRNA that target HBx or DDB1. HBV-infected PHH were transfected with siRNA to the indicated gene or a non-targeting control siRNA (Ctrl) or were mock-transfected on day 6 post-infection or were treated with 1 nM entecavir (ETV) from day 6-21 post-infection. Mock-infected (uninfected) PHH were included as a control. (A) Plot shows extracellular HBV DNA and HBeAg at day 21 post-infection. Data are expressed as a percentage of the no treatment control; the bar height indicates the mean of n=3 independent experiments and the errors bars represent the SEM. (B) PHH were analyzed by confocal microscopy at day 21 post-infection. Data from n=3 independent experiments is shown; the bar height indicates the mean and the errors bars represent the SEM. At least n=92 nuclei were analyzed per condition. Statistical significance relative to the no treatment control was calculated by one-way ANOVA with Dunnett's multiple comparison correction. *p<0.05, ***p<0.001, ns: not significant (p>0.05). Data from uninfected PHH were not included in the statistical analysis.
Figure 10B:
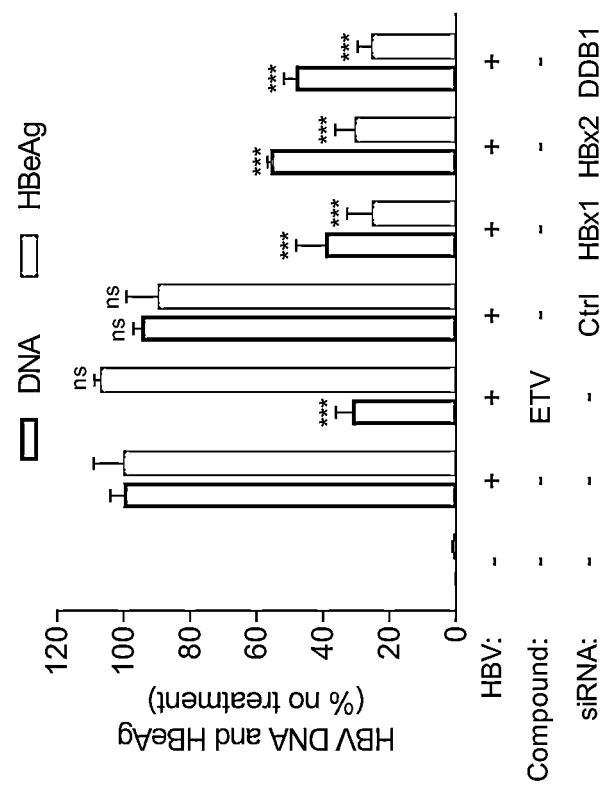

We therefore determined if HBx protein levels could be reduced by RNA interference and whether this would lead to the reappearance of the Smc5/6 complex and silencing of cccDNA transcription. HBV-infected PHH were treated with either the nucleoside analogue entecavir (ETV) or were transfected with a non-targeting control siRNA (siCtrl), an siRNA targeting the HBx open reading frame (siHBx1 (also called siHBV herein) and siHBx2) or an siRNA targeting the HBx binding partner DDB1 (siDDB1). The siRNAs were transfected into HBV-infected PHH at day 6 post-infection, by which time Smc6 has been degraded in the majority of infected cells (FIG. 6) (Niu et al. PLoS One 2017; 12: e0169648). As expected, ETV significantly reduced extracellular HBV DNA levels, but not HBeAg levels, and siCtrl had no antiviral activity (FIGS. 8A, 9A and 10A). Neither ETV nor siCtrl significantly reduced the percentage of HBx-positive cells or increased the percentage of Smc6-positive cells (FIGS. 8B and 10B). In contrast, treatment with siHBx1 or siHBx2 significantly reduced extracellular HBV DNA and HBeAg levels (FIGS. 8A and 10A), as well as the percentage of HBx-positive cells (FIGS. 8B and 10B). However, while about 30% cells were still HBx-positive after treatment with these siRNA, about 40% cells became Smc6-positive. Thus, there was a sizeable population of PHH (~30% for siHBx1, 50% for siHBx2) which remained Smc6-negative after siHBx treatment, but had no detectable HBx (i.e. below the detection limit of this assay). This observation is in line with the viral kinetics data suggesting that low levels of HBx are sufficient to target Smc5/6 for degradation (FIG. 6).

As previously reported (Decorsière, et al., *Nature* (2016) 531:386-389), inhibiting HBx function with siDDB1 significantly reduced extracellular HBV DNA and HBeAg (FIGS. 9A and 10A). This siRNA also significantly reduced the number of HBx-positive cells (FIGS. 9B and 10B). In contrast to siHBx1 and siHBx2, the majority of cells (70%) became Smc6-positive after siDDB1 treatment (FIG. 10B). Collectively these data demonstrate that although siRNAs targeting HBx can significantly decrease HBx levels in HBV-infected PHH, restoration of Smc5/6 requires very potent HBx reduction. As an alternative approach, inhibiting HBx function—modelled here by siDDB1 treatment—may be an efficient way to induce cccDNA transcriptional silencing by the Smc5/6 complex. Indeed, inhibiting the HBx-DDB1 interaction is a promising therapeutic strategy because it alters HBx cellular localization (FIG. 11) and reduces HBx stability (Bergametti, et al., *J Virol* (2002) 76:6495-501), in addition to inhibiting HBx function (FIG. 12).

The data from this study also facilitates the rational development of new RNAi therapeutics for CHB. Inhibiting HBx by RNA interference is a promising therapeutic strategy since restoration of Smc5/6 is expected to lead to transcriptional silencing of cccDNA. To-date, selection of HBx siRNA triggers has typically relied on measurement of surrogate viral endpoints (e.g., HBV DNA, levels of secreted viral antigens) to infer anti-HBx activity. However, the current study indicates that neither reduction of standard HBV replication endpoints (FIG. 12A) nor decrease in intracellular HBx levels (FIG. 12B) are good predictors of HBx functional inhibition by siRNA triggers. Instead, our data are consistent with the conclusion that restoration of structural maintenance of chromosomes 6 (SMC6) (Gene ID No. 79677) levels (or other subunits of the Smc5/6 complex, e.g., including without limitation, structural maintenance of chromosomes 5 (SMC5) (Gene ID No. 23137), NSE1 homolog, SMC5-SMC6 complex component (NSMCE1) (Gene ID No. 197370), NSE2 (MMS21) homolog, SMC5-SMC6 complex SUMO ligase (NSMCE2) (Gene ID No. 286053), NSE3 homolog, SMC5-SMC6 complex component (NSMCE3) (Gene ID No. 56160) and/or NSE4 homolog A, SMC5-SMC6 complex component (NSMCE4A) (Gene ID No. 54780)) in HBV-infected hepatocytes is an additional criterion for consideration when selecting siRNAs for clinical development.

HBx Interaction with DDB1 Promotes Nuclear Localization

Figure 11A:
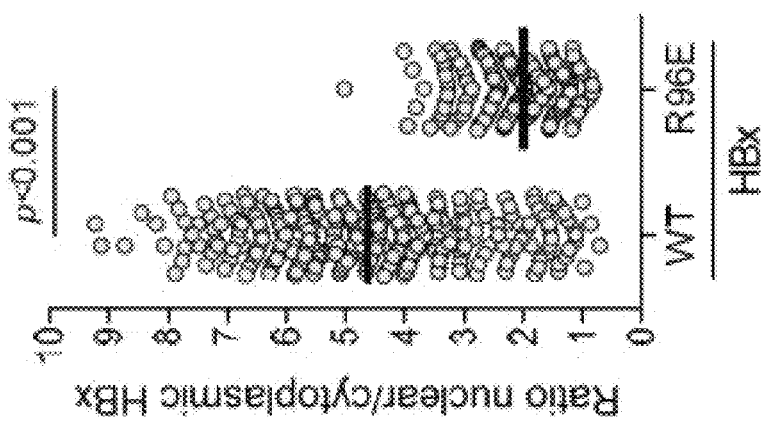
FIGS. 11A and 11B illustrate that DDB1 binding alters HBx localization. PHH were transduced with lentivirus expressing wild-type HBx or the DDB1-binding mutant HBx R96E and analyzed by confocal microscopy at day 3 post-transduction. (A) PHH were stained for HBx (red) and nuclei were stained with DAPI (blue). Representative confocal images from n=3 independent experiments are shown. Scale bar represents 10 m. Nuclei are outlined by white dotted lines in all images. (B) Single cell quantitation was performed to determine the HBx-specific fluorescence signal in the nucleus and the cytoplasm of transduced cells. The plot shows the ratio of nuclear to cytoplasmic HBx. Each point represents an individual cell and the line represents the mean. Data is combined from three independent experiments; ≥56 cells were analyzed per condition in each experiment. Non-expressing cells were excluded from the analysis after they were identified using cut-off values based on the nuclear HBx-specific fluorescence signal in PHH transduced with a control (GFP only) lentivirus. Statistical significance was calculated by unpaired t-test.
Figure 11B:
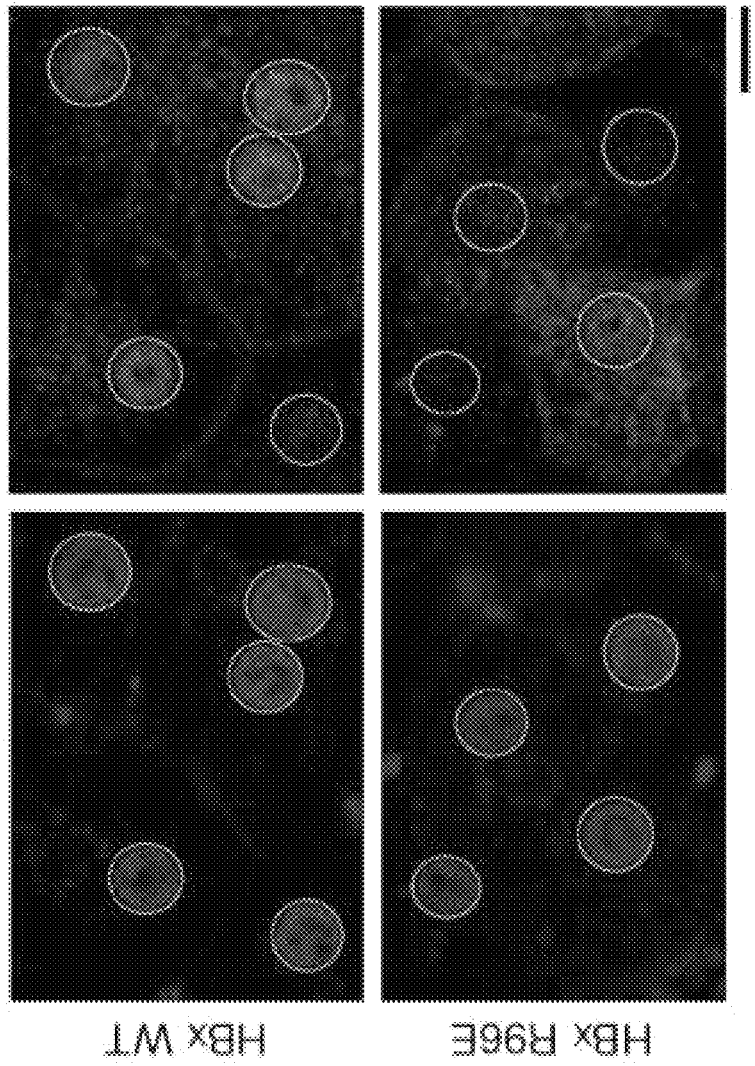
Figure 12A:
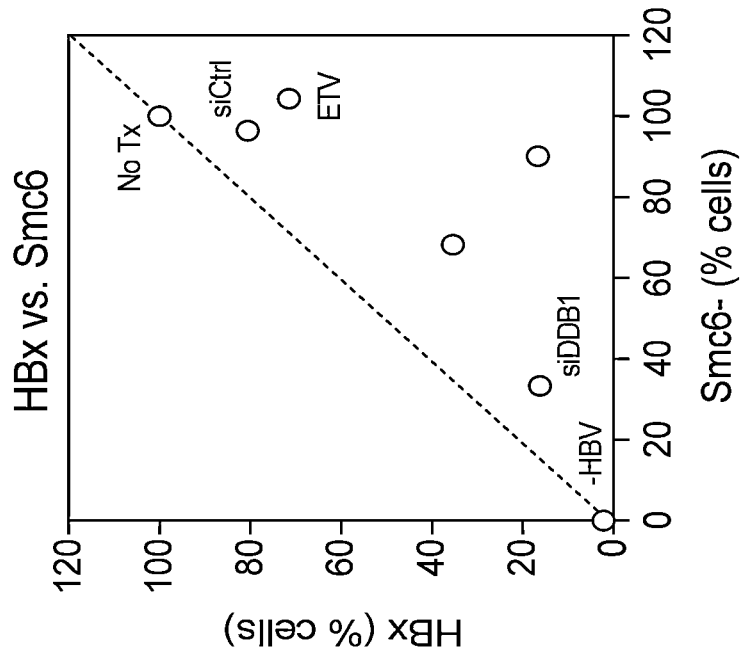
FIGS. 12A and 12B illustrate that HBeAg or HBx reduction alone are poor indicators of whether HBx function has been effectively inhibited (i.e. the Smc5/6 complex has been restored; cells are Smc6+) by siRNA targeting of the HBx region. % Smc6− levels plotted on the x-axis were calculated by subtracting background levels (% of Smc6+ cells after HBV infection, no Tx); normalization to uninfected cells (% of Smc6+ cells) and then conversion to % Smc6− cells by subtracting from 100. Tx, treatment. Data in the right plot is derived from FIG. 10B. In both plots, the green circle depicts uninfected (−HBV) cells. The orange circle depicts HBV-infected PHH with no treatment (no Tx). The blue circle depicts control siRNA (siCtrl). The purple circle depicts siRNA targeting DDB1 (siDDB1). Each grey circle represents an individual siRNA targeting the HBx region of the HBV genome. In the right plot, the dark red circle depicts tenofovir treated PHH.
Figure 12B:
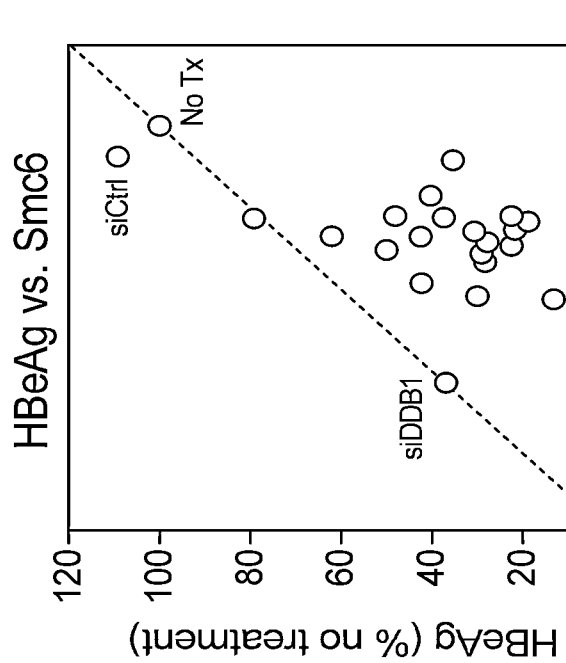

We have previously demonstrated that Smc5/6 localizes with ND10 in the nuclei of uninfected PHH, and that HBV infection does not induce degradation of ND10 structural components PML and Sp100 (Niu, et al., *PLoS One* (2017) 12:e0169648). The diffuse nuclear staining pattern of HBx indicates that it does not predominantly localize to these intranuclear structures. We therefore attempted to determine whether HBx instead co-localizes with DDB1 in HBV-infected PHH. Unfortunately, we were not successful in identifying a DDB1-selective antibody that was suitable for immunofluorescence. As an alternative approach, we compared the spatial distribution of lentivirus expressed wild-type HBx with a DDB1-binding mutant HBx R96E (Lin-Marq, et al., *Virology* (2001) 287:266-74; Li, et al., *Nat Struct Mol Biol* (2010) 17:105-11). Consistent with the spatial distribution of HBx expressed in the context of natural infection, wild-type (WT) HBx predominantly localized to the nucleus of PHH (FIG. 11A). Conversely, HBx R96E was detected in the cytoplasm as well as the nucleus (FIG. 11A). Quantitative single cell analysis demonstrated that the HBx R96E mutant has a significantly lower nuclear to cytoplasmic signal ratio than wild-type HBx (mean 2.0 vs. 4.6, respectively), confirming that the DDB1-binding mutant is more evenly distributed between these cellular compartments (FIG. 11). Taken together, these data suggest that the interaction with DDB1 plays a role in the nuclear localization of HBx. In addition, the observation that the HBx R96E mutant is present in the nucleus but does not induce Smc6 degradation or rescue HBVΔX transcription, underlines the importance of the HBx-DDB1 interaction for HBx function as well as localization (Decorsière, et al., Nature (2016) 531:386-389, Leupin, et al., J Virol (2005) 79:4238-45).

Using a novel monoclonal HBx antibody, it was demonstrated that HBx localizes to the nucleus, is expressed early after HBV infection of PHH, and has a short half life. The described anti-HBx antibody has yielded new insights into virus-host interactions, and also has utility for evaluating new therapeutic agents.

It was also determined that inhibition of HBx function or reduction of HBx mRNA levels in HBV-infected PHH leads to the reappearance of Smc6.

These data suggest that cccDNA transcriptional silencing by the Smc5/6 complex may be restored by therapeutic targeting of HBx.

Example 2 (Prophetic). Detection of the Presence of HBx in Hepatoma Cell Lines with Integrated HBV The expression of HBx is measured in five HBV-associated hepatoma cell lines by confocal microscopy using a monoclonal antibody that has the VH and VL regions disclosed in Table 1. The cell lines do not contain cccDNA and/or are not releasing HBV virions. A subset of the HBV hepatoma cell lines are found to express HBx.

Genomic sequencing confirms that each of the cells that express HBx have integrated HBV DNA that encodes the HBx gene.

Example 3 (Prophetic). Detection of the HBx in the Livers of Humanized Mice (Immunodeficient Mice Containing Human Hepatocytes) Infected with HBV Immunodeficient mice containing human hepatocytes are infected with HBV. Infected mice are euthanized at 5, 10, and 15 weeks after infection, and their livers are collected. The level of HBx is measured in the livers by IHC or Western blot analysis using a monoclonal antibody having the VH and VL regions disclosed in Table 1.

HBx expression is detected in the livers of the infected mice, and the amount of HBx increases over time.

Example 4 (Prophetic). Detection of the Presence of HBx in Biopsies from HBV-Infected Patients and Patients with HBV-Associated HCC Liver tissue biopsies are collected from a first group of patients that has been diagnosed with chronic HBV infection and a second group of patients who have been diagnosed with HBV-associated HCC.

IHC and Western blot analysis using a monoclonal antibody having the VH and VL regions disclosed in Table 1 is performed on FFPE and lysates, respectively, from the biopsies.

HBx expression is detected in the first patient group and a subset of the second patient group. HBx expression is higher in HCC tumors compared to HBV-infected cells.

Example 5 (Prophetic). An Intrabody Including the Variable Regions of HBx M19 Inhibits cccDNA Transcription when Expressed in HBV-Infected PHH PHH cells are transfected with a plasmid that directs the expression of an intrabody. The intrabody includes a scFv and a nuclear localization signal. The scFv includes the VH and VL regions disclosed in Table 1. PHH cells that are transfected with an empty plasmid serve as controls.

The transfected PHH are then infected with HBV, and cccDNA transcription is detected at various timepoints post-infection. cccDNA transcription is detected by measuring intracellular HBV RNA, extracellular HBeAg, extracellular HBsAg, HBV DNA, and/or intracellular core.

The infected PHH that express the intrabody show less cccDNA transcription than the infected PHH that do not express the intrabody.

Although the foregoing disclosure has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant disclosure and a reference provided herein, the instant disclosure shall dominate.

SEQUENCE LISTING

<160> NUMBER OF SEQ ID NOS: 76

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      Heavy CDR1 Kabat

<400> SEQUENCE: 1

Asp Tyr Tyr Met Asn
1               5

```
<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      Heavy CDR2 Kabat

<400> SEQUENCE: 2

Asp Ile Asn Pro Asn Asn Gly Gly Thr Ala Tyr Asn Gln Lys Phe Lys
1               5                   10                  15

Gly

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      Light CDR1 Kabat

<400> SEQUENCE: 3

Arg Ser Ser Gln Ser Leu Val Tyr Ser Asp Gly Asn Thr His Leu His
1               5                   10                  15

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      Light CDR2 Kabat

<400> SEQUENCE: 4

Lys Ala Ser Asn Arg Phe Ser
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      Light CDR3 Kabat

<400> SEQUENCE: 5

Ser Gln Ser Thr His Val Pro Leu Thr
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      Heavy CDR1 IMGT

<400> SEQUENCE: 6

Gly Tyr Thr Phe Thr Asp Tyr Tyr
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
      Heavy CDR2 IMGT

<400> SEQUENCE: 7

Ile Asn Pro Asn Asn Gly Gly Thr
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      Heavy CDR3 IMGT

<400> SEQUENCE: 8

Ala Leu Leu Ala Tyr
1               5

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      Light CDR1 IMGT

<400> SEQUENCE: 9

Gln Ser Leu Val Tyr Ser Asp Gly Asn Thr His
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      Light CDR3 IMGT

<400> SEQUENCE: 10

Ser Gln Ser Thr His Val Pro Leu Thr
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      Heavy CDR1 Chothia

<400> SEQUENCE: 11

Gly Tyr Thr Phe Thr Asp Tyr
1               5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      Heavy CDR2 Chothia

<400> SEQUENCE: 12

Pro Asn Asn Gly
1

<210> SEQ ID NO 13
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      Light CDR1 Chothia

<400> SEQUENCE: 13

Ser Gln Ser Leu Val Tyr Ser Asp Gly Asn Thr His
1               5                   10

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      Light CDR3 Chothia

<400> SEQUENCE: 14

Ser Thr His Val Pro Leu
1               5

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      Heavy CDR1 Honegger

<400> SEQUENCE: 15

Ala Ser Gly Tyr Thr Phe Thr Asp Tyr Tyr
1               5                   10

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      Heavy CDR2 Honegger

<400> SEQUENCE: 16

Ile Asn Pro Asn Asn Gly Gly Thr Ala Tyr Asn Gln Lys Phe Lys Gly
1               5                   10                  15

Lys

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      Light CDR1 Honegger

<400> SEQUENCE: 17

Ser Ser Gln Ser Leu Val Tyr Ser Asp Gly Asn Thr His
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      Light CDR2 Honegger
```

```
<400> SEQUENCE: 18

Lys Ala Ser Asn Arg Phe Ser Gly Val Pro Asp Arg
1               5                   10

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      Light CDR3 Honegger

<400> SEQUENCE: 19

Ser Thr His Val Pro Leu
1               5

<210> SEQ ID NO 20
<211> LENGTH: 436
<212> TYPE: PRT
<213> ORGANISM: Artificial Sequence
<220> FEATURE:
<223> OTHER INFORMATION: Description of Artificial Sequence: Synthetic
      Variant of HBx M19 Heavy Chain

<400> SEQUENCE: 20

Glu Val Gln Leu Gln Gln Ser Gly Pro Glu Leu Val Lys Pro Gly Ala
1               5                   10                  15

Ser Val Lys Ile Ser Cys Gln Ala Ser Gly Tyr Thr Phe Thr Asp Tyr
            20                  25                  30

Tyr Met Asn Trp Val Lys Gln Ser His Gly Lys Arg Leu Glu Trp Ile
        35                  40                  45

Gly Asp Ile Asn Pro Asn Asn Gly Gly Thr Ala Tyr Asn Gln Lys Phe
    50                  55                  60

Lys Gly Lys Ala Thr Leu Thr Val Asp Arg Ser Ser Ser Thr Ala Tyr
65                  70                  75                  80

Met Glu Val Arg Ser Leu Thr Ser Glu Asp Ser Ala Val Tyr Phe Cys
                85                  90                  95

Ala Leu Leu Ala Tyr Trp Gly Gln Gly Thr Leu Val Thr Val Ser Ala
            100                 105                 110

Ala Lys Thr Thr Pro Pro Ser Val Tyr Pro Leu Ala Pro Gly Ser Ala
        115                 120                 125

Ala Gln Thr Asn Ser Met Val Thr Leu Gly Cys Leu Val Lys Gly Tyr
    130                 135                 140

Phe Pro Glu Pro Val Thr Val Thr Trp Asn Ser Gly Ser Leu Ser Ser
145                 150                 155                 160

Gly Val His Thr Phe Pro Ala Val Leu Gln Ser Asp Leu Tyr Thr Leu
                165                 170                 175

Ser Ser Ser Val Thr Val Pro Ser Ser Thr Trp Pro Ser Glu Thr Val
            180                 185                 190

Thr Cys Asn Val Ala His Pro Ala Ser Ser Thr Lys Val Asp Lys Lys
        195                 200                 205

Ile Val Pro Arg Asp Cys Gly Cys Lys Pro Cys Ile Cys Thr Val Pro
    210                 215                 220

Glu Val Ser Ser Val Phe Ile Phe Pro Pro Lys Pro Lys Asp Val Leu
225                 230                 235                 240

Thr Ile Thr Leu Thr Pro Lys Val Thr Cys Val Val Val Asp Ile Ser
                245                 250                 255

Lys Asp Asp Pro Glu Val Gln Phe Ser Trp Phe Val Asp Asp Val Glu
```

```
                    260                 265                 270
Val His Thr Ala Gln Thr Gln Pro Arg Glu Glu Gln Phe Asn Ser Thr
            275                 280                 285

Phe Arg Ser Val Ser Glu Leu Pro Ile Met His Gln Asp Trp Leu Asn
        290                 295                 300

Gly Lys Glu Phe Lys Cys Arg Val Asn Ser Ala Ala Phe Pro Ala Pro
305                 310                 315                 320

Ile Glu Lys Thr Ile Ser Lys Thr Lys Gly Arg Pro Lys Ala Pro Gln
                325                 330                 335

Val Tyr Thr Ile Pro Pro Pro Lys Glu Gln Met Ala Lys Asp Lys Val
            340                 345                 350

Ser Leu Thr Cys Met Ile Thr Asp Phe Phe Pro Glu Asp Ile Thr Val
        355                 360                 365

Glu Trp Gln Trp Asn Gly Gln Pro Ala Glu Asn Tyr Lys Asn Thr Gln
370                 375                 380

Pro Ile Met Asp Thr Asp Gly Ser Tyr Phe Val Tyr Ser Lys Leu Asn
385                 390                 395                 400

Val Gln Lys Ser Asn Trp Glu Ala Gly Asn Thr Phe Thr Cys Ser Val
                405                 410                 415

Leu His Glu Gly Leu His Asn His His Thr Glu Lys Ser Leu Ser His
            420                 425                 430

Ser Pro Gly Lys
        435

<210> SEQ ID NO 21
<211> LENGTH: 101
<212> TYPE: PRT
<213> ORGANISM: Artificial Sequence
<220> FEATURE:
<223> OTHER INFORMATION: Description of Artificial Sequence: Synthetic
      Heavy Chain Variable Region without -(D)-J Sequence

<400> SEQUENCE: 21

Glu Val Gln Leu Gln Gln Ser Gly Pro Glu Leu Val Lys Pro Gly Ala
1               5                   10                  15

Ser Val Lys Ile Ser Cys Gln Ala Ser Gly Tyr Thr Phe Thr Asp Tyr
            20                  25                  30

Tyr Met Asn Trp Val Lys Gln Ser His Gly Lys Arg Leu Glu Trp Ile
        35                  40                  45

Gly Asp Ile Asn Pro Asn Asn Gly Gly Thr Ala Tyr Asn Gln Lys Phe
    50                  55                  60

Lys Gly Lys Ala Thr Leu Thr Val Asp Arg Ser Ser Ser Thr Ala Tyr
65                  70                  75                  80

Met Glu Val Arg Ser Leu Thr Ser Glu Asp Ser Ala Val Tyr Phe Cys
                85                  90                  95

Ala Leu Leu Ala Tyr
            100

<210> SEQ ID NO 22
<211> LENGTH: 112
<212> TYPE: PRT
<213> ORGANISM: Artificial Sequence
<220> FEATURE:
<223> OTHER INFORMATION: Description of Artificial Sequence: Synthetic
      Heavy Chain Variable Region

<400> SEQUENCE: 22

Glu Val Gln Leu Gln Gln Ser Gly Pro Glu Leu Val Lys Pro Gly Ala
```

```
               1               5                  10                 15
            Ser Val Lys Ile Ser Cys Gln Ala Ser Gly Tyr Thr Phe Thr Asp Tyr
                           20                 25                 30

Tyr Met Asn Trp Val Lys Gln Ser His Gly Lys Arg Leu Glu Trp Ile
                           35                 40                 45

Gly Asp Ile Asn Pro Asn Asn Gly Gly Thr Ala Tyr Asn Gln Lys Phe
                           50                 55                 60

Lys Gly Lys Ala Thr Leu Thr Val Asp Arg Ser Ser Thr Ala Tyr
            65                 70                 75                 80

Met Glu Val Arg Ser Leu Thr Ser Glu Asp Ser Ala Val Tyr Phe Cys
                           85                 90                 95

Ala Leu Leu Ala Tyr Trp Gly Gln Gly Thr Leu Val Thr Val Ser Ala
                          100                105                110

<210> SEQ ID NO 23
<211> LENGTH: 102
<212> TYPE: PRT
<213> ORGANISM: Artificial Sequence
<220> FEATURE:
<223> OTHER INFORMATION: Description of Artificial Sequence: Synthetic
      Light Chain Variable Region without -(D)-J Sequence

<400> SEQUENCE: 23

Asp Val Val Met Thr Gln Thr Pro Leu Ser Leu Pro Val Ser Leu Gly
1               5                  10                 15

Asp Gln Ala Ser Ile Ser Cys Arg Ser Ser Gln Ser Leu Val Tyr Ser
                20                 25                 30

Asp Gly Asn Thr His Leu His Trp Tyr Leu Gln Lys Thr Gly Gln Ser
                35                 40                 45

Pro Lys Leu Leu Ile Tyr Lys Ala Ser Asn Arg Phe Ser Gly Val Pro
            50                 55                 60

Asp Arg Phe Ser Gly Ser Gly Ser Gly Thr Asp Phe Thr Leu Lys Ile
65                 70                 75                 80

Ser Arg Val Glu Ala Glu Asp Leu Gly Val Tyr Phe Cys Ser Gln Ser
                85                 90                 95

Thr His Val Pro Leu Thr
            100

<210> SEQ ID NO 24
<211> LENGTH: 112
<212> TYPE: PRT
<213> ORGANISM: Artificial Sequence
<220> FEATURE:
<223> OTHER INFORMATION: Description of Artificial Sequence: Synthetic
      Light Chain Variable Region

<400> SEQUENCE: 24

Asp Val Val Met Thr Gln Thr Pro Leu Ser Leu Pro Val Ser Leu Gly
1               5                  10                 15

Asp Gln Ala Ser Ile Ser Cys Arg Ser Ser Gln Ser Leu Val Tyr Ser
                20                 25                 30

Asp Gly Asn Thr His Leu His Trp Tyr Leu Gln Lys Thr Gly Gln Ser
                35                 40                 45

Pro Lys Leu Leu Ile Tyr Lys Ala Ser Asn Arg Phe Ser Gly Val Pro
            50                 55                 60

Asp Arg Phe Ser Gly Ser Gly Ser Gly Thr Asp Phe Thr Leu Lys Ile
65                 70                 75                 80

Ser Arg Val Glu Ala Glu Asp Leu Gly Val Tyr Phe Cys Ser Gln Ser
```

```
                      85                  90                  95
Thr His Val Pro Leu Thr Phe Gly Ala Gly Thr Lys Leu Glu Leu Lys
                100                 105                 110

<210> SEQ ID NO 25
<211> LENGTH: 324
<212> TYPE: PRT
<213> ORGANISM: Artificial Sequence
<220> FEATURE:
<223> OTHER INFORMATION: Description of Artificial Sequence: Synthetic
      Mouse IgG

<400> SEQUENCE: 25

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
                20                  25                  30

Phe Pro Glu Pro Val Thr Val Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60

Ser Ser Ser Val Thr Val Pro Ser Ser Thr Trp Pro Ser Gln Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
                100                 105                 110

Glu Val Ser Ser Val Phe Ile Phe Pro Pro Lys Pro Lys Asp Val Leu
            115                 120                 125

Thr Ile Thr Leu Thr Pro Lys Val Thr Cys Val Val Val Asp Ile Ser
        130                 135                 140

Lys Asp Asp Pro Glu Val Gln Phe Ser Trp Phe Val Asp Asp Val Glu
145                 150                 155                 160

Val His Thr Ala Gln Thr Lys Pro Arg Glu Glu Gln Ile Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
        210                 215                 220

Val Tyr Thr Ile Pro Pro Lys Glu Gln Met Ala Lys Asp Lys Val
225                 230                 235                 240

Ser Leu Thr Cys Met Ile Thr Asn Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys
```

```
<210> SEQ ID NO 26
<211> LENGTH: 107
<212> TYPE: PRT
<213> ORGANISM: Artificial Sequence
<220> FEATURE:
<223> OTHER INFORMATION: Description of Artificial Sequence: Synthetic
      Light Chain Constant Region

<400> SEQUENCE: 26

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Gly Glu Cys
            100                 105

<210> SEQ ID NO 27
<211> LENGTH: 436
<212> TYPE: PRT
<213> ORGANISM: Artificial Sequence
<220> FEATURE:
<223> OTHER INFORMATION: Description of Artificial Sequence: Synthetic
      Heavy Chains of HBx M19

<400> SEQUENCE: 27

Glu Val Gln Leu Gln Gln Ser Gly Pro Glu Leu Val Lys Pro Gly Ala
1               5                   10                  15

Ser Val Lys Ile Ser Cys Gln Ala Ser Gly Tyr Thr Phe Thr Asp Tyr
            20                  25                  30

Tyr Met Asn Trp Val Lys Gln Ser His Gly Lys Arg Leu Glu Trp Ile
        35                  40                  45

Gly Asp Ile Asn Pro Asn Asn Gly Gly Thr Ala Tyr Asn Gln Lys Phe
    50                  55                  60

Lys Gly Lys Ala Thr Leu Thr Val Asp Arg Ser Ser Ser Thr Ala Tyr
65                  70                  75                  80

Met Glu Val Arg Ser Leu Thr Ser Glu Asp Ser Ala Val Tyr Phe Cys
                85                  90                  95

Ala Leu Leu Ala Tyr Trp Gly Gln Gly Thr Leu Val Thr Val Ser Ala
            100                 105                 110

Ala Lys Thr Thr Pro Pro Ser Val Tyr Pro Leu Ala Pro Gly Ser Ala
        115                 120                 125

Ala Gln Thr Asn Ser Met Val Thr Leu Gly Cys Leu Val Lys Gly Tyr
    130                 135                 140

Phe Pro Glu Pro Val Thr Val Thr Trp Asn Ser Gly Ser Leu Ser Ser
145                 150                 155                 160

Gly Val His Thr Phe Pro Ala Val Leu Gln Ser Asp Leu Tyr Thr Leu
                165                 170                 175

Ser Ser Ser Val Thr Val Pro Ser Ser Thr Trp Pro Ser Gln Thr Val
            180                 185                 190

Thr Cys Asn Val Ala His Pro Ala Ser Ser Thr Lys Val Asp Lys Lys
```

```
                195                 200                 205
Ile Val Pro Arg Asp Cys Gly Cys Lys Pro Cys Ile Cys Thr Val Pro
        210                 215                 220

Glu Val Ser Ser Val Phe Ile Phe Pro Pro Lys Pro Lys Asp Val Leu
225                 230                 235                 240

Thr Ile Thr Leu Thr Pro Lys Val Thr Cys Val Val Val Asp Ile Ser
                245                 250                 255

Lys Asp Asp Pro Glu Val Gln Phe Ser Trp Phe Val Asp Asp Val Glu
                260                 265                 270

Val His Thr Ala Gln Thr Lys Pro Arg Glu Glu Gln Ile Asn Ser Thr
            275                 280                 285

Phe Arg Ser Val Ser Glu Leu Pro Ile Met His Gln Asp Trp Leu Asn
            290                 295                 300

Gly Lys Glu Phe Lys Cys Arg Val Asn Ser Ala Ala Phe Pro Ala Pro
305                 310                 315                 320

Ile Glu Lys Thr Ile Ser Lys Thr Lys Gly Arg Pro Lys Ala Pro Gln
                325                 330                 335

Val Tyr Thr Ile Pro Pro Pro Lys Glu Gln Met Ala Lys Asp Lys Val
                340                 345                 350

Ser Leu Thr Cys Met Ile Thr Asn Phe Phe Pro Glu Asp Ile Thr Val
            355                 360                 365

Glu Trp Gln Trp Asn Gly Gln Pro Ala Glu Asn Tyr Lys Asn Thr Gln
            370                 375                 380

Pro Ile Met Asp Thr Asp Gly Ser Tyr Phe Val Tyr Ser Lys Leu Asn
385                 390                 395                 400

Val Gln Lys Ser Asn Trp Glu Ala Gly Asn Thr Phe Thr Cys Ser Val
                405                 410                 415

Leu His Glu Gly Leu His Asn His His Thr Glu Lys Ser Leu Ser His
            420                 425                 430

Ser Pro Gly Lys
            435

<210> SEQ ID NO 28
<211> LENGTH: 19
<212> TYPE: PRT
<213> ORGANISM: Artificial Sequence
<220> FEATURE:
<223> OTHER INFORMATION: Description of Artificial Sequence: Synthetic
      Leader peptide that may be present at the N-terminus of a heavy
      chain

<400> SEQUENCE: 28

Met Gly Trp Ser Trp Val Phe Leu Phe Leu Leu Ser Gly Thr Ala Gly
1               5                   10                  15

Val Leu Ser

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      Heavy Chain -(D)-J Sequence

<400> SEQUENCE: 29

Trp Gly Gln Gly Thr Leu Val Thr Val Ser Ala
1               5                   10
```

<210> SEQ ID NO 30
<211> LENGTH: 219
<212> TYPE: PRT
<213> ORGANISM: Artificial Sequence
<220> FEATURE:
<223> OTHER INFORMATION: Description of Artificial Sequence: Synthetic
      Light Chain

<400> SEQUENCE: 30

```
Asp Val Val Met Thr Gln Thr Pro Leu Ser Leu Pro Val Ser Leu Gly
1               5                   10                  15

Asp Gln Ala Ser Ile Ser Cys Arg Ser Gln Ser Leu Val Tyr Ser
            20                  25                  30

Asp Gly Asn Thr His Leu His Trp Tyr Leu Gln Lys Gly Gln Ser
        35                  40                  45

Pro Lys Leu Leu Ile Tyr Lys Ala Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
                100                 105                 110

Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
                180                 185                 190

Arg His Asn Ser Tyr Thr Cys Glu Ala Thr His Lys Thr Ser Thr Ser
            195                 200                 205

Pro Ile Val Lys Ser Phe Asn Arg Gly Glu Cys
    210                 215
```

<210> SEQ ID NO 31
<211> LENGTH: 19
<212> TYPE: PRT
<213> ORGANISM: Artificial Sequence
<220> FEATURE:
<223> OTHER INFORMATION: Description of Artificial Sequence: Synthetic
      Leader peptide that may be present at the N-terminus of a light
      chain

<400> SEQUENCE: 31

```
Met Lys Leu Pro Val Arg Leu Leu Val Leu Met Phe Trp Ile Pro Ala
1               5                   10                  15

Ser Ser Ser
```

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      Light Chain -(D)-J Sequence

<400> SEQUENCE: 32

```
Phe Gly Ala Gly Thr Lys Leu Glu Leu Lys
1               5                  10

<210> SEQ ID NO 33
<211> LENGTH: 324
<212> TYPE: PRT
<213> ORGANISM: Artificial Sequence
<220> FEATURE:
<223> OTHER INFORMATION: Description of Artificial Sequence: Synthetic
      Heavy Chain Constant Region

<400> SEQUENCE: 33

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
                20                  25                  30

Phe Pro Glu Pro Val Thr Val Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 34
```

<211> LENGTH: 435
<212> TYPE: PRT
<213> ORGANISM: Artificial Sequence
<220> FEATURE:
<223> OTHER INFORMATION: Description of Artificial Sequence: Synthetic Heavy Chain

<400> SEQUENCE: 34

```
Glu Val Gln Leu Gln Gln Ser Gly Pro Glu Leu Val Lys Pro Gly Ala
1               5                   10                  15

Ser Val Lys Ile Ser Cys Gln Ala Ser Gly Tyr Thr Phe Thr Asp Tyr
            20                  25                  30

Tyr Met Asn Trp Val Lys Gln Ser His Gly Lys Arg Leu Glu Trp Ile
        35                  40                  45

Gly Asp Ile Asn Pro Asn Asn Gly Gly Thr Ala Tyr Asn Gln Lys Phe
    50                  55                  60

Lys Gly Lys Ala Thr Leu Thr Val Asp Arg Ser Ser Thr Ala Tyr
65                  70                  75                  80

Met Glu Val Arg Ser Leu Thr Ser Glu Asp Ser Ala Val Tyr Phe Cys
                85                  90                  95

Ala Leu Leu Ala Tyr Trp Gly Gln Gly Thr Leu Val Thr Val Ser Ala
            100                 105                 110

Gly Gln Pro Lys Ala Pro Ser Val Phe Pro Leu Ala Pro Cys Cys Gly
        115                 120                 125

Asp Thr Pro Ser Ser Thr Val Thr Leu Gly Cys Leu Val Lys Gly Tyr
    130                 135                 140

Leu Pro Glu Pro Val Thr Val Thr Trp Asn Ser Gly Thr Leu Thr Asn
145                 150                 155                 160

Gly Val Arg Thr Phe Pro Ser Val Arg Gln Ser Ser Gly Leu Tyr Ser
                165                 170                 175

Leu Ser Ser Val Val Ser Val Thr Ser Ser Ser Gln Pro Val Thr Cys
            180                 185                 190

Asn Val Ala His Pro Ala Thr Asn Thr Lys Val Asp Lys Thr Val Ala
        195                 200                 205

Pro Ser Thr Cys Ser Lys Pro Thr Cys Pro Pro Pro Glu Leu Leu Gly
    210                 215                 220

Gly Pro Ser Val Phe Ile Phe Pro Pro Lys Pro Lys Asp Thr Leu Met
225                 230                 235                 240

Ile Ser Arg Thr Pro Glu Val Thr Cys Val Val Val Asp Val Ser Gln
                245                 250                 255

Asp Asp Pro Glu Val Gln Phe Thr Trp Tyr Ile Asn Asn Glu Gln Val
            260                 265                 270

Arg Thr Ala Arg Pro Pro Leu Arg Glu Gln Gln Phe Asn Ser Thr Ile
        275                 280                 285

Arg Val Val Ser Thr Leu Pro Ile Ala His Gln Asp Trp Leu Arg Gly
    290                 295                 300

Lys Glu Phe Lys Cys Lys Val His Asn Lys Ala Leu Pro Ala Pro Ile
305                 310                 315                 320

Glu Lys Thr Ile Ser Lys Ala Arg Gly Gln Pro Leu Glu Pro Lys Val
                325                 330                 335

Tyr Thr Met Gly Pro Pro Arg Glu Glu Leu Ser Ser Arg Ser Val Ser
            340                 345                 350

Leu Thr Cys Met Ile Asn Gly Phe Tyr Pro Ser Asp Ile Ser Val Glu
        355                 360                 365

Trp Glu Lys Asn Gly Lys Ala Glu Asp Asn Tyr Lys Thr Thr Pro Ala
```

```
                    370                 375                 380
Val Leu Asp Ser Asp Gly Ser Tyr Phe Leu Tyr Ser Lys Leu Ser Val
385                 390                 395                 400

Pro Thr Ser Glu Trp Gln Arg Gly Asp Val Phe Thr Cys Ser Val Met
                405                 410                 415

His Glu Ala Leu His Asn His Tyr Thr Gln Lys Ser Ile Ser Arg Ser
                420                 425                 430

Pro Gly Lys
        435

<210> SEQ ID NO 35
<211> LENGTH: 323
<212> TYPE: PRT
<213> ORGANISM: Artificial Sequence
<220> FEATURE:
<223> OTHER INFORMATION: Description of Artificial Sequence: Synthetic
      Heavy Chain Constant Region

<400> SEQUENCE: 35

Gly Gln Pro Lys Ala Pro Ser Val Phe Pro Leu Ala Pro Cys Cys Gly
1               5                   10                  15

Asp Thr Pro Ser Ser Thr Val Thr Leu Gly Cys Leu Val Lys Gly Tyr
                20                  25                  30

Leu Pro Glu Pro Val Thr Val Thr Trp Asn Ser Gly Thr Leu Thr Asn
            35                  40                  45

Gly Val Arg Thr Phe Pro Ser Val Arg Gln Ser Ser Gly Leu Tyr Ser
        50                  55                  60

Leu Ser Ser Val Val Ser Val Thr Ser Ser Ser Gln Pro Val Thr Cys
65                  70                  75                  80

Asn Val Ala His Pro Ala Thr Asn Thr Lys Val Asp Lys Thr Val Ala
                85                  90                  95

Pro Ser Thr Cys Ser Lys Pro Thr Cys Pro Pro Pro Glu Leu Leu Gly
            100                 105                 110

Gly Pro Ser Val Phe Ile Phe Pro Pro Lys Pro Lys Asp Thr Leu Met
        115                 120                 125

Ile Ser Arg Thr Pro Glu Val Thr Cys Val Val Val Asp Val Ser Gln
    130                 135                 140

Asp Asp Pro Glu Val Gln Phe Thr Trp Tyr Ile Asn Asn Glu Gln Val
145                 150                 155                 160

Arg Thr Ala Arg Pro Pro Leu Arg Glu Gln Gln Phe Asn Ser Thr Ile
                165                 170                 175

Arg Val Val Ser Thr Leu Pro Ile Ala His Gln Asp Trp Leu Arg Gly
            180                 185                 190

Lys Glu Phe Lys Cys Lys Val His Asn Lys Ala Leu Pro Ala Pro Ile
        195                 200                 205

Glu Lys Thr Ile Ser Lys Ala Arg Gly Gln Pro Leu Glu Pro Lys Val
    210                 215                 220

Tyr Thr Met Gly Pro Pro Arg Glu Glu Leu Ser Ser Arg Ser Val Ser
225                 230                 235                 240

Leu Thr Cys Met Ile Asn Gly Phe Tyr Pro Ser Asp Ile Ser Val Glu
                245                 250                 255

Trp Glu Lys Asn Gly Lys Ala Glu Asp Asn Tyr Lys Thr Thr Pro Ala
            260                 265                 270

Val Leu Asp Ser Asp Gly Ser Tyr Phe Leu Tyr Ser Lys Leu Ser Val
        275                 280                 285
```

```
Pro Thr Ser Glu Trp Gln Arg Gly Asp Val Phe Thr Cys Ser Val Met
    290                 295                 300

His Glu Ala Leu His Asn His Tyr Thr Gln Lys Ser Ile Ser Arg Ser
305                 310                 315                 320

Pro Gly Lys

<210> SEQ ID NO 36
<211> LENGTH: 216
<212> TYPE: PRT
<213> ORGANISM: Artificial Sequence
<220> FEATURE:
<223> OTHER INFORMATION: Description of Artificial Sequence: Synthetic
      Light Chain

<400> SEQUENCE: 36

Asp Val Val Met Thr Gln Thr Pro Leu Ser Leu Pro Val Ser Leu Gly
1               5                   10                  15

Asp Gln Ala Ser Ile Ser Cys Arg Ser Gln Ser Leu Val Tyr Ser
            20                  25                  30

Asp Gly Asn Thr His Leu His Trp Tyr Leu Gln Lys Thr Gly Gln Ser
        35                  40                  45

Pro Lys Leu Leu Ile Tyr Lys Ala Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
            100                 105                 110

Gly Asp Pro Val Ala Pro Thr Val Leu Ile Phe Pro Pro Ala Ala Asp
        115                 120                 125

Gln Val Ala Thr Gly Thr Val Thr Ile Val Cys Val Ala Asn Lys Tyr
    130                 135                 140

Phe Pro Asp Val Thr Val Thr Trp Glu Val Asp Gly Thr Thr Gln Thr
145                 150                 155                 160

Thr Gly Ile Glu Asn Ser Lys Thr Pro Gln Asn Ser Ala Asp Ser Thr
                165                 170                 175

Tyr Asn Leu Ser Ser Thr Leu Thr Leu Thr Ser Thr Gln Tyr Asn Ser
            180                 185                 190

His Lys Glu Tyr Thr Cys Lys Val Thr Gln Gly Thr Thr Ser Val Val
        195                 200                 205

Gln Ser Phe Asn Arg Gly Asp Cys
    210                 215

<210> SEQ ID NO 37
<211> LENGTH: 104
<212> TYPE: PRT
<213> ORGANISM: Artificial Sequence
<220> FEATURE:
<223> OTHER INFORMATION: Description of Artificial Sequence: Synthetic
      Light Chain Constant Region

<400> SEQUENCE: 37

Gly Asp Pro Val Ala Pro Thr Val Leu Ile Phe Pro Pro Ala Ala Asp
1               5                   10                  15

Gln Val Ala Thr Gly Thr Val Thr Ile Val Cys Val Ala Asn Lys Tyr
            20                  25                  30

Phe Pro Asp Val Thr Val Thr Trp Glu Val Asp Gly Thr Thr Gln Thr
```

```
                35                  40                  45
Thr Gly Ile Glu Asn Ser Lys Thr Pro Gln Asn Ser Ala Asp Ser Thr
 50                  55                  60

Tyr Asn Leu Ser Ser Thr Leu Thr Leu Thr Ser Thr Gln Tyr Asn Ser
 65                  70                  75                  80

His Lys Glu Tyr Thr Cys Lys Val Thr Gln Gly Thr Thr Ser Val Val
                 85                  90                  95

Gln Ser Phe Asn Arg Gly Asp Cys
                100

<210> SEQ ID NO 38
<211> LENGTH: 322
<212> TYPE: PRT
<213> ORGANISM: Artificial Sequence
<220> FEATURE:
<223> OTHER INFORMATION: Description of Artificial Sequence: Synthetic
      Rat IgG

<400> SEQUENCE: 38

Ala Glu Thr Thr Ala Pro Ser Val Tyr Pro Leu Ala Pro Gly Thr Ala
  1               5                  10                  15

Leu Lys Ser Asn Ser Met Val Thr Leu Gly Cys Leu Val Lys Gly Tyr
                 20                  25                  30

Phe Pro Glu Pro Val Thr Val Thr Trp Asn Ser Gly Ala Leu Ser Ser
                 35                  40                  45

Gly Val His Thr Phe Pro Ala Val Leu Gln Ser Gly Leu Tyr Thr Leu
 50                  55                  60

Thr Ser Ser Val Thr Val Pro Ser Ser Thr Trp Ser Ser Gln Ala Val
 65                  70                  75                  80

Thr Cys Asn Val Ala His Pro Ala Ser Ser Thr Lys Val Asp Lys Lys
                 85                  90                  95

Ile Val Pro Arg Glu Cys Asn Pro Cys Gly Cys Thr Gly Ser Glu Val
                100                 105                 110

Ser Ser Val Phe Ile Phe Pro Pro Lys Thr Lys Asp Val Leu Thr Ile
                115                 120                 125

Thr Leu Thr Pro Lys Val Thr Cys Val Val Val Asp Ile Ser Gln Asn
                130                 135                 140

Asp Pro Glu Val Arg Phe Ser Trp Phe Ile Asp Asp Val Glu Val His
145                 150                 155                 160

Thr Ala Gln Thr His Ala Pro Glu Lys Gln Ser Asn Ser Thr Leu Arg
                165                 170                 175

Ser Val Ser Glu Leu Pro Ile Val His Arg Asp Trp Leu Asn Gly Lys
                180                 185                 190

Thr Phe Lys Cys Lys Val Asn Ser Gly Ala Phe Pro Ala Pro Ile Glu
                195                 200                 205

Lys Ser Ile Ser Lys Pro Glu Gly Thr Pro Arg Gly Pro Gln Val Tyr
                210                 215                 220

Thr Met Ala Pro Pro Lys Glu Glu Met Thr Gln Ser Gln Val Ser Ile
225                 230                 235                 240

Thr Cys Met Val Lys Gly Phe Tyr Pro Pro Asp Ile Tyr Thr Glu Trp
                245                 250                 255

Lys Met Asn Gly Gln Pro Gln Glu Asn Tyr Lys Asn Thr Pro Pro Thr
                260                 265                 270

Met Asp Thr Asp Gly Ser Tyr Phe Leu Tyr Ser Lys Leu Asn Val Lys
                275                 280                 285
```

```
Lys Glu Thr Trp Gln Gln Gly Asn Thr Phe Thr Cys Ser Val Leu His
    290                 295                 300

Glu Gly Leu His Asn His His Thr Glu Lys Ser Leu Ser His Ser Pro
305             310                 315                 320

Gly Lys
```

<210> SEQ ID NO 39
<211> LENGTH: 1402
<212> TYPE: DNA
<213> ORGANISM: Artificial Sequence
<220> FEATURE:
<223> OTHER INFORMATION: Description of Artificial Sequence: Synthetic
      Heavy Chain Coding Sequence

<400> SEQUENCE: 39

```
acccaagctg gctagccgcc accatgaaat gggtcacctt tatcagcctg ctgttcctgt    60
tcagcagcgc ctactctgag gtccagctgc agcaatctgg ccccgagctt gtgaaacctg   120
gcgcctctgt gaagatcagc tgtcaggcca gcggctacac cttcaccgac tactacatga   180
actgggttaa gcagagccac ggcaagcggc tggaatggat cggcgacatc aaccccaaca   240
atggcggcac cgcctacaac cagaagttca agggcaaagc cacactgacc gtggacagaa   300
gcagcagcac agcctacatg gaagtgcgga gcctgaccag cgaagatagc gccgtgtact   360
tctgtgccct gctggcctat ggggccagg gaacactggt tacagtgtcc gctgggcaac   420
ctaaggctcc atcagtcttc ccactggcac catgctgcgg tgacacacct agctccacgg   480
tgaccctggg atgcctggtc aaaggctacc tcccagagcc agtgaccgtg acctggaact   540
cgggtacact caccaatggt gtacgcacct tcccatccgt ccggcagtcc tcaggactct   600
actcgctgtc gagcgttgtg agcgtgacct caagcagcca gcctgtcacc tgcaacgtgg   660
ctcacccagc tactaacacc aaagtggaca agaccgttgc caatcgaca tgcagcaagc   720
ctacgtgccc acctcctgaa ctcctgggtg gaccgtctgt cttcatcttc cctccaaaac   780
ctaaggacac cctcatgatc tcacgcacac ctgaggtcac atgcgttgtt gtggacgtga   840
gccaggatga cccagaggtg cagttcacat ggtacataaa caacgagcag gttcgcacag   900
ctcggcctcc tctacgagag caacagttca acagcacgat ccgcgtggtc agcacactcc   960
ctatcgcgca ccaggactgg ctgagggta aggagttcaa gtgcaaagtc cacaacaagg  1020
cactccctgc tcctatcgag aaaaccatct ccaaagccag aggtcagcct ctggagccga  1080
aggtctacac catgggacct ccacgggagg agctgagcag caggtcggtc agcctgacct  1140
gcatgatcaa cggattctac ccttccgaca tctcggtgga gtgggagaag aacggtaagg  1200
cagaggacaa ctacaagacc acgcctgccg tgctggacag cgacggttcc tacttcctct  1260
acagcaagct ctcagtgcct acgagtgagt ggcagcgggg tgacgtcttc acctgctccg  1320
tgatgcacga ggccttgcac aaccactaca cgcagaagtc catctcccgc tctccgggta  1380
agtaggaatt ctgcagatat ca                                           1402
```

<210> SEQ ID NO 40
<211> LENGTH: 5428
<212> TYPE: DNA
<213> ORGANISM: Artificial Sequence
<220> FEATURE:
<223> OTHER INFORMATION: Description of Artificial Sequence: Synthetic
      vector pcDNA?3.1+

<400> SEQUENCE: 40

```
gacggatcgg gagatctccc gatccccta t ggtgcactct cagtacaatc tgctctgatg    60
```

```
ccgcatagtt aagccagtat ctgctccctg cttgtgtgtt ggaggtcgct gagtagtgcg        120
cgagcaaaat ttaagctaca acaaggcaag gcttgaccga caattgcatg aagaatctgc        180
ttagggttag gcgttttgcg ctgcttcgcg atgtacgggc cagatatacg cgttgacatt        240
gattattgac tagttattaa tagtaatcaa ttacggggtc attagttcat agcccatata        300
tggagttccg cgttacataa cttacggtaa atggcccgcc tggctgaccg cccaacgacc        360
cccgcccatt gacgtcaata atgacgtatg ttcccatagt aacgccaata gggactttcc        420
attgacgtca atgggtggag tatttacggt aaactgccca cttggcagta catcaagtgt        480
atcatatgcc aagtacgccc cctattgacg tcaatgacgg taaatggccc gcctggcatt        540
atgcccagta catgacctta tgggactttc ctacttggca gtacatctac gtattagtca        600
tcgctattac catggtgatg cggttttggc agtacatcaa tgggcgtgga tagcggtttg        660
actcacgggg atttccaagt ctccacccca ttgacgtcaa tgggagtttg ttttggcacc        720
aaaatcaacg ggactttcca aaatgtcgta acaactccgc cccattgacg caaatgggcg        780
gtaggcgtgt acggtgggag gtctatataa gcagagctct ctggctaact agagaaccca        840
ctgcttactg gcttatcgaa attaatacga ctcactatag ggagacccaa gctggctagc        900
gtttaaactt aagcttggta ccgagctcgg atccactagt ccagtgtggt ggaattctgc        960
agatatccag cacagtggcg gccgctcgag tctagagggc ccgtttaaac ccgctgatca        1020
gcctcgactg tgccttctag ttgccagcca tctgttgttt gcccctcccc cgtgccttcc        1080
ttgaccctgg aaggtgccac tcccactgtc ctttcctaat aaaatgagga aattgcatcg        1140
cattgtctga gtaggtgtca ttctattctg gggggtgggg tggggcagga cagcaagggg        1200
gaggattggg aagacaatag caggcatgct ggggatgcgg tgggctctat ggcttctgag        1260
gcggaaagaa ccagctgggg ctctaggggg tatccccacg cgccctgtag cggcgcatta        1320
agcgcggcgg gtgtggtggt tacgcgcagc gtgaccgcta cacttgccag cgccctagcg        1380
cccgctcctt tcgctttctt cccttccttt ctcgccacgt tcgccggctt tccccgtcaa        1440
gctctaaatc gggggctccc tttagggttc cgatttagtg ctttacgca cctcgacccc        1500 aaaaaacttg attagggtga tggttcacgt agtgggccat cgccctgata acggttttt         1560 cgcccttga cgttggagtc cacgttcttt aatagtggac tcttgttcca aactggaaca         1620
acactcaacc ctatctcggt ctattctttt gatttataag ggattttgcc gatttcggcc        1680
tattggttaa aaatgagct gatttaacaa aaatttaacg cgaattaatt ctgtggaatg         1740
tgtgtcagtt agggtgtgga aagtccccag gctccccagc aggcagaagt atgcaaagca        1800
tgcatctcaa ttagtcagca accaggtgtg gaaagtcccc aggctcccca gcaggcagaa        1860
gtatgcaaag catgcatctc aattagtcag caaccatagt cccgccccta actccgccca        1920
tcccgcccct aactccgccc agttccgccc attctccgcc ccatggctga ctaatttttt        1980
ttatttatgc agaggccgag gccgcctctg cctctgagct attccagaag tagtgaggag        2040
gcttttttgg aggcctaggc ttttgcaaaa agctcccggg agcttgtata tccatttcg         2100 gatctgatca agagacagga tgaggatcgt ttcgcatgat tgaacaagat ggattgcacg        2160
caggttctcc ggccgcttgg gtggagaggc tattcggcta tgactgggca acagacaa          2220 tcggctgctc tgatgccgcc gtgttccggc tgtcagcgca ggggcgcccg gttcttttttg       2280 tcaagaccga cctgtccggt gccctgaatg aactgcagga cgaggcagcg cggctatcgt        2340
ggctggccac gacgggcgtt ccttgcgcag ctgtgctcga cgttgtcact gaagcgggaa        2400
```

```
gggactggct gctattgggc gaagtgccgg ggcaggatct cctgtcatct caccttgctc    2460
ctgccgagaa agtatccatc atggctgatg caatgcggcg gctgcatacg cttgatccgg    2520
ctacctgccc attcgaccac caagcgaaac atcgcatcga gcgagcacgt actcggatgg    2580
aagccggtct tgtcgatcag gatgatctgg acgaagagca tcagggctc gcgccagccg     2640 aactgttcgc caggctcaag gcgcgcatgc ccgacggcga ggatctcgtc gtgacccatg    2700
gcgatgcctg cttgccgaat atcatggtgg aaaatggccg cttttctgga ttcatcgact    2760
gtggccggct gggtgtggcg gaccgctatc aggacatagc gttggctacc cgtgatattg    2820
ctgaagagct tggcggcgaa tgggctgacc gcttcctcgt gctttacggt atcgccgctc    2880
ccgattcgca gcgcatcgcc ttctatcgcc ttcttgacga gttcttctga gcgggactct    2940
ggggttcgaa atgaccgacc aagcgacgcc caacctgcca tcacgagatt tcgattccac    3000
cgccgccttc tatgaaaggt tgggcttcgg aatcgttttc cgggacgccg gctggatgat    3060
cctccagcgc ggggatctca tgctggagtt cttcgcccac cccaacttgt ttattgcagc    3120
ttataatggt tacaaataaa gcaatagcat cacaaatttc acaaataaag cattttttc     3180 actgcattct agttgtggtt tgtccaaact catcaatgta tcttatcatg tctgtatacc    3240
gtcgacctct agctagagct tggcgtaatc atggtcatag ctgtttcctg tgtgaaattg    3300
ttatccgctc acaattccac acaacatacg agccggaagc ataaagtgta agcctggggg    3360
tgcctaatga gtgagctaac tcacattaat tgcgttgcgc tcactgcccg ctttccagtc    3420
gggaaacctg tcgtgccagc tgcattaatg aatcggccaa cgcgcgggga gaggcggttt    3480
gcgtattggg cgctcttccg cttcctcgct cactgactcg ctgcgctcgg tcgttcggct    3540
gcggcgagcg gtatcagctc actcaaaggc ggtaatacgg ttatccacag aatcagggga    3600
taacgcagga aagaacatgt gagcaaaagg ccagcaaaag gccaggaacc gtaaaaaggc    3660
cgcgttgctg gcgttttcc ataggctccg ccccctgac gagcatcaca aaaatcgacg     3720
ctcaagtcag aggtggcgaa acccgacagg actataaaga taccaggcgt ttccccctgg    3780
aagctccctc gtgcgctctc ctgttccgac cctgccgctt accggatacc tgtccgcctt    3840
tctcccttcg ggaagcgtgg cgctttctca tagctcacgc tgtaggtatc tcagttcggt    3900
gtaggtcgtt cgctccaagc tgggctgtgt gcacgaaccc cccgttcagc ccgaccgctg    3960
cgccttatcc ggtaactatc gtcttgagtc caacccggta agacacgact tatcgccact    4020
ggcagcagcc actggtaaca ggattagcag agcgaggtat gtaggcggtg ctacagagtt    4080
cttgaagtgg tggcctaact acggctacac tagaagaaca gtatttggta tctgcgctct    4140
gctgaagcca gttaccttcg aaaaagagt tggtagctct tgatccggca acaaaccac     4200 cgctggtagc ggttttttg tttgcaagca gcagattacg cgcagaaaaa aaggatctca     4260
agaagatcct ttgatctttt ctacggggtc tgacgctcag tggaacgaaa actcacgtta    4320 agggatttg gtcatgagat tatcaaaaag gatcttcacc tagatccttt taaattaaaa     4380
atgaagtttt aaatcaatct aaagtatata tgagtaaact tggtctgaca gttaccaatg    4440
cttaatcagt gaggcaccta tctcagcgat ctgtctattt cgttcatcca tagttgcctg    4500
actccccgtc gtgtagataa ctacgatacg ggagggctta ccatctggcc ccagtgctgc    4560
aatgataccg cgagacccac gctcaccggc tccagattta tcagcaataa accagccagc    4620
cggaagggcc gagcgcagaa gtggtcctgc aactttatcc gcctccatcc agtctattaa    4680
ttgttgccgg gaagctagag taagtagttc gccagttaat agtttgcgca acgttgttgc    4740
cattgctaca ggcatcgtgg tgtcacgctc gtcgtttggt atggcttcat tcagctccgg    4800
```

```
ttcccaacga tcaaggcgag ttacatgatc ccccatgttg tgcaaaaaag cggttagctc    4860
cttcggtcct ccgatcgttg tcagaagtaa gttggccgca gtgttatcac tcatggttat    4920
ggcagcactg cataattctc ttactgtcat gccatccgta agatgctttt ctgtgactgg    4980
tgagtactca accaagtcat tctgagaata gtgtatgcgg cgaccgagtt gctcttgccc    5040
ggcgtcaata cgggataata ccgcgccaca tagcagaact taaaagtgc tcatcattgg     5100 aaaacgttct tcggggcgaa aactctcaag gatcttaccg ctgttgagat ccagttcgat    5160
gtaacccact cgtgcaccca actgatcttc agcatctttt actttcacca gcgtttctgg    5220
gtgagcaaaa acaggaaggc aaaatgccgc aaaaaaggga ataagggcga cacggaaatg    5280
ttgaatactc atactcttcc tttttcaata ttattgaagc atttatcagg gttattgtct    5340
catgagcgga tacatatttg aatgtattta gaaaaataaa caaatagggg ttccgcgcac    5400
atttccccga aaagtgccac ctgacgtc                                      5428
```

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      Coding sequence is appended to the 3' end of the last codon of
      the heavy chain constant region

<400> SEQUENCE: 41
caccatcacc atcaccatca ccat                                          24

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      nuclear localization signal

<400> SEQUENCE: 42

Gly Gly Ser Gly Pro Pro Lys Lys Lys Arg Lys Val
1               5                   10

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      nuclear localization signal

<400> SEQUENCE: 43

Pro Lys Lys Lys Arg Lys Val
1               5

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      nuclear localization signal

<400> SEQUENCE: 44

Lys Arg Pro Ala Ala Thr Lys Lys Ala Gly Gln Ala Lys Lys Lys Lys
1               5                   10                  15

```
<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      nuclear localization signal
<220> FEATURE:
<221> NAME/KEY: MOD_RES
<222> LOCATION: (3)..(12)
<223> OTHER INFORMATION: Any amino acid

<400> SEQUENCE: 45

Lys Arg Xaa Xaa Xaa Xaa Xaa Xaa Xaa Xaa Xaa Xaa Lys Lys Lys Lys
1               5                   10                  15

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      nuclear localization signal
<220> FEATURE:
<221> NAME/KEY: MOD_RES
<222> LOCATION: (3)..(3)
<223> OTHER INFORMATION: Any amino acid

<400> SEQUENCE: 46

Lys Lys Xaa Lys
1

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
      nuclear localization signal
<220> FEATURE:
<221> NAME/KEY: MOD_RES
<222> LOCATION: (3)..(3)
<223> OTHER INFORMATION: Any amino acid

<400> SEQUENCE: 47

Lys Arg Xaa Lys
1

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence: Synthetic
      nuclear localization signal
<220> FEATURE:
<221> NAME/KEY: MOD_RES
<222> LOCATION: (3)..(3)
<223> OTHER INFORMATION: Any amino acid

<400> SEQUENCE: 48

Lys Lys Xaa Arg
1

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: Synthetic
``` nuclear localization signal
<220> FEATURE:
<221> NAME/KEY: MOD_RES
<222> LOCATION: (3)..(3)
<223> OTHER INFORMATION: Any amino acid

<400> SEQUENCE: 49

Lys Arg Xaa Arg
1

<210> SEQ ID NO 50
<211> LENGTH: 20
<212> TYPE: PRT
<213> ORGANISM: Artificial Sequence
<220> FEATURE:
<223> OTHER INFORMATION: Description of Artificial Sequence: Synthetic
       nuclear localization signal

<400> SEQUENCE: 50

Ala Val Lys Arg Pro Ala Ala Thr Lys Lys Ala Gly Gln Ala Lys Lys
1               5                   10                  15

Lys Lys Leu Asp
            20

<210> SEQ ID NO 51
<211> LENGTH: 25
<212> TYPE: PRT
<213> ORGANISM: Artificial Sequence
<220> FEATURE:
<223> OTHER INFORMATION: Description of Artificial Sequence: Synthetic
       nuclear localization signal

<400> SEQUENCE: 51

Met Ser Arg Arg Arg Lys Ala Asn Pro Thr Lys Leu Ser Glu Asn Ala
1               5                   10                  15

Lys Lys Leu Ala Lys Glu Val Glu Asn
            20                  25

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
       nuclear localization signal

<400> SEQUENCE: 52

Pro Ala Ala Lys Arg Val Lys Leu Asp
1               5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
       nuclear localization signal

<400> SEQUENCE: 53

Pro Pro Lys Lys Lys Arg Lys Val
1               5

<210> SEQ ID NO 54
<211> LENGTH: 9
<212> TYPE: PRT
<213> ORGANISM: Artificial Sequence
<220> FEATURE:

<223> OTHER INFORMATION: Description of Artificial Sequence: Synthetic
nuclear localization signal

<400> SEQUENCE: 54

Lys Leu Lys Ile Lys Arg Pro Val Lys
1               5

<210> SEQ ID NO 55
<211> LENGTH: 25
<212> TYPE: PRT
<213> ORGANISM: Artificial Sequence
<220> FEATURE:
<223> OTHER INFORMATION: Description of Artificial Sequence: Synthetic
mitochondrial localization signal

<400> SEQUENCE: 55

Met Leu Ser Leu Arg Gln Ser Ile Arg Phe Phe Lys Pro Ala Thr Arg
1               5                   10                  15

Thr Leu Cys Ser Ser Arg Tyr Leu Leu
            20                  25

<210> SEQ ID NO 56
<211> LENGTH: 728
<212> TYPE: DNA
<213> ORGANISM: Artificial Sequence
<220> FEATURE:
<223> OTHER INFORMATION: Description of Artificial Sequence: Synthetic
Light Chain Coding Sequence

<400> SEQUENCE: 56
acccaagctg gctagccgcc accatgaaat gggtcacctt tatcagcctg ctgttcctgt     60
tcagcagcgc ctacagcgac gtggtcatga cacagacccc actgagcctg cctgtgtctc    120
tgggagatca ggccagcatc agctgcagat ctagccagag cctggtgtac tccgacggca    180
acacacatct gcactggtat ctgcagaaaa ccggacagag ccccaagctg ctgatctaca    240
aggccagcaa cagattcagc ggcgtgcccg atagattttc cggcagcggc tctggcaccg    300
acttcaccct gaagatctcc agagtggaag ccgaggacct gggcgtgtac ttctgtagcc    360
agtctaccca cgtgccactg acctttggcg ccggaacaaa gctggaactg aagggtgatc    420
cagttgcacc tactgtcctc atcttcccac cagctgctga tcaggtggca actggaacag    480
tcaccatcgt gtgtgtggcg aataaatact ttcccgatgt caccgtcacc tgggaggtgg    540
atggcaccac ccaaacaact ggcatcgaga acagtaaaac accgcagaac tctgcagatt    600
ctacctacaa cctcagcagc actctgacac tgaccagcac acagtacaac agccacaaag    660
agtacacctg caaggtgacc cagggcacga cctcagtcgt ccagagcttc aacaggggtg    720
actgctag                                                             728

<210> SEQ ID NO 57
<211> LENGTH: 1388
<212> TYPE: DNA
<213> ORGANISM: Artificial Sequence
<220> FEATURE:
<223> OTHER INFORMATION: Description of Artificial Sequence: Synthetic
Heavy Chain Coding Sequence

<400> SEQUENCE: 57
acccaagctg gctagccgcc accatgaaat gggtcacctt tatcagcctg ctgttcctgt     60
tcagcagcgc ctactctgag gtccagctgc agcaatctgg ccccgagctt gtgaaacctg    120
gcgcctctgt gaagatcagc tgtcaggcca gcggctacac cttcaccgac tactacatga    180

```
actgggttaa gcagagccac ggcaagcggc tggaatggat cggcgacatc aaccccaaca    240
atggcggcac cgcctacaac cagaagttca agggcaaagc cacactgacc gtggacagaa    300
gcagcagcac agcctacatg gaagtgcgga gcctgaccag cgaagatagc gccgtgtact    360
tctgtgccct gctggcctat tggggccagg gaacactggt tacagtgtcc gctgctaaaa    420
cgacaccccc atctgtctat ccactggccc ctggatctgc tgcccaaact aactccatgg    480
tgaccctggg atgcctggtc aagggctatt ccctgagcc agtgacagtg acctggaact    540
ctggatccct gtccagcggt gtgcacacct cccagctgt cctgcagtct gacctctaca    600
ctctgagcag ctcagtgact gtcccctcca gcacctggcc cagcgagacc gtcacctgca    660
acgttgccca cccggccagc agcaccaagg tggacaagaa aattgtgccc agggattgtg    720
gttgtaagcc ttgcatatgt acagtcccag aagtatcatc tgtcttcatc ttccccccaa    780
agcccaagga tgtgctcacc attactctga ctcctaaggt cacgtgtgtt gtggtagaca    840
tcagcaagga tgatcccgag gtccagttca gctggtttgt agatgatgtg gaggtgcaca    900
cagctcagac gcaaccccgg gaggagcagt tcaacagcac tttccgctca gtcagtgaac    960
ttcccatcat gcaccaggac tggctcaatg gcaaggagtt caaatgcagg gtcaacagtg   1020
cagctttccc tgcccccatc gagaaaacca tctccaaaac caaaggcaga ccgaaggctc   1080
cgcaggtgta caccattcca cctcccaagg agcagatggc caaggataaa gtcagtctga   1140
cctgcatgat aacagacttc ttccctgaag acattactgt ggagtggcag tggaatgggc   1200
agccagcgga gaactacaag aacactcagc ccatcatgga cacagatggc tcttacttcg   1260
tctacagcaa gctcaatgtg cagaagagca actgggaggc aggaaatact ttcacctgct   1320
ctgtgttaca tgagggcctg cacaaccacc atactgagaa gagcctctcc cactctcctg   1380
gtaaatga                                                            1388

<210> SEQ ID NO 58
<211> LENGTH: 753
<212> TYPE: DNA
<213> ORGANISM: Artificial Sequence
<220> FEATURE:
<223> OTHER INFORMATION: Description of Artificial Sequence: Synthetic
      Light Chain Coding Sequence

<400> SEQUENCE: 58
acccaagctg gctagccgcc accatgaaat gggtcacctt tatcagcctg ctgttcctgt     60
tcagcagcgc ctacagcgac gtggtcatga cacagacccc actgagcctg cctgtgtctc    120
tgggagatca ggccagcatc agctgcagat ctagccagag cctggtgtac tccgacggca    180
acacacatct gcactggtat ctgcagaaaa ccggacagag ccccaagctg ctgatctaca    240
aggccagcaa cagattcagc ggcgtgcccg atagatttc cggcagcggc tctggcaccg    300
acttcaccct gaagatctcc agagtggaag ccgaggacct gggcgtgtac ttctgtagcc    360
agtctaccca cgtgccactg acctttggcg ccggaacaaa gctggaactg aagcgggcag    420
atgctgcacc aactgtatcc atcttcccac catccagtga gcagttaaca tctggaggtg    480
cctcagtcgt gtgcttcttg aacaacttct accccaaaga catcaatgtc aagtggaaga    540
ttgatggcag tgaacgacaa aatggcgtcc tgaacagttg gactgatcag gacagcaaag    600
acagcaccta cagcatgagc agcaccctca cgttgaccaa ggacgagtat gaacgacata    660
acagctatac ctgtgaggcc actcacaaga catcaacttc acccattgtc aagagcttca    720
acaggaatga gtgttaggaa ttctgcagat atc                                 753
```

<210> SEQ ID NO 59
<211> LENGTH: 18
<212> TYPE: PRT
<213> ORGANISM: Artificial Sequence
<220> FEATURE:
<223> OTHER INFORMATION: Description of Artificial Sequence: Synthetic
      Leader peptide that may be present at the N-terminus of a heavy
      chain

<400> SEQUENCE: 59

Met Lys Trp Val Thr Phe Ile Ser Leu Leu Phe Leu Phe Ser Ser Ala
1               5                   10                  15

Tyr Ser

<210> SEQ ID NO 60
<211> LENGTH: 219
<212> TYPE: PRT
<213> ORGANISM: Artificial Sequence
<220> FEATURE:
<223> OTHER INFORMATION: Description of Artificial Sequence: Synthetic
      Light Chain

<400> SEQUENCE: 60

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val Tyr Ser
            20                  25                  30

Asp Gly Asn Thr His Leu His Trp Tyr Leu Gln Lys Thr Gly Gln Ser
        35                  40                  45

Pro Lys Leu Leu Ile Tyr Lys Ala Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 61
<211> LENGTH: 107
<212> TYPE: PRT
<213> ORGANISM: Artificial Sequence
<220> FEATURE:
<223> OTHER INFORMATION: Description of Artificial Sequence: Synthetic
      Light Chain Constant Region

```
<400> SEQUENCE: 61

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 62
<211> LENGTH: 455
<212> TYPE: PRT
<213> ORGANISM: Artificial Sequence
<220> FEATURE:
<223> OTHER INFORMATION: Description of Artificial Sequence: Synthetic
      Heavy Chain

<400> SEQUENCE: 62

Met Gly Trp Ser Trp Val Phe Leu Phe Leu Leu Ser Gly Thr Ala Gly
1               5                   10                  15

Val Leu Ser Glu Val Gln Leu Gln Gln Ser Gly Pro Glu Leu Val Lys
            20                  25                  30

Pro Gly Ala Ser Val Lys Ile Ser Cys Gln Ala Ser Gly Tyr Thr Phe
        35                  40                  45

Thr Asp Tyr Tyr Met Asn Trp Val Lys Gln Ser His Gly Lys Arg Leu
    50                  55                  60

Glu Trp Ile Gly Asp Ile Asn Pro Asn Asn Gly Gly Thr Ala Tyr Asn
65                  70                  75                  80

Gln Lys Phe Lys Gly Lys Ala Thr Leu Thr Val Asp Arg Ser Ser Ser
                85                  90                  95

Thr Ala Tyr Met Glu Val Arg Ser Leu Thr Ser Glu Asp Ser Ala Val
                100                 105                 110

Tyr Phe Cys Ala Leu Leu Ala Tyr Trp Gly Gln Gly Thr Leu Val Thr
            115                 120                 125

Val Ser Ala Ala Lys Thr Thr Pro Pro Ser Val Tyr Pro Leu Ala Pro
130                 135                 140

Gly Ser Ala Ala Gln Thr Asn Ser Met Val Thr Leu Gly Cys Leu Val
145                 150                 155                 160

Lys Gly Tyr Phe Pro Glu Pro Val Thr Val Thr Trp Asn Ser Gly Ser
                165                 170                 175

Leu Ser Ser Gly Val His Thr Phe Pro Ala Val Leu Gln Ser Asp Leu
            180                 185                 190

Tyr Thr Leu Ser Ser Ser Val Thr Val Pro Ser Ser Thr Trp Pro Ser
        195                 200                 205

Gln Thr Val Thr Cys Asn Val Ala His Pro Ala Ser Ser Thr Lys Val
    210                 215                 220

Asp Lys Lys Ile Val Pro Arg Asp Cys Gly Cys Lys Pro Cys Ile Cys
225                 230                 235                 240
```

```
Thr Val Pro Glu Val Ser Ser Val Phe Ile Phe Pro Lys Pro Lys
                245                 250                 255

Asp Val Leu Thr Ile Thr Leu Thr Pro Lys Val Thr Cys Val Val Val
            260                 265                 270

Asp Ile Ser Lys Asp Pro Glu Val Gln Phe Ser Trp Phe Val Asp
        275                 280                 285

Asp Val Glu Val His Thr Ala Gln Thr Lys Pro Arg Glu Glu Gln Ile
    290                 295                 300

Asn Ser Thr Phe Arg Ser Val Ser Glu Leu Pro Ile Met His Gln Asp
305                 310                 315                 320

Trp Leu Asn Gly Lys Glu Phe Lys Cys Arg Val Asn Ser Ala Ala Phe
                325                 330                 335

Pro Ala Pro Ile Glu Lys Thr Ile Ser Lys Thr Lys Gly Arg Pro Lys
            340                 345                 350

Ala Pro Gln Val Tyr Thr Ile Pro Pro Pro Lys Glu Gln Met Ala Lys
        355                 360                 365

Asp Lys Val Ser Leu Thr Cys Met Ile Thr Asn Phe Phe Pro Glu Asp
    370                 375                 380

Ile Thr Val Glu Trp Gln Trp Asn Gly Gln Pro Ala Glu Asn Tyr Lys
385                 390                 395                 400

Asn Thr Gln Pro Ile Met Asp Thr Asp Gly Ser Tyr Phe Val Tyr Ser
                405                 410                 415

Lys Leu Asn Val Gln Lys Ser Asn Trp Glu Ala Gly Asn Thr Phe Thr
            420                 425                 430

Cys Ser Val Leu His Glu Gly Leu His Asn His His Thr Glu Lys Ser
        435                 440                 445

Leu Ser His Ser Pro Gly Lys
    450                 455

<210> SEQ ID NO 63
<211> LENGTH: 238
<212> TYPE: PRT
<213> ORGANISM: Artificial Sequence
<220> FEATURE:
<223> OTHER INFORMATION: Description of Artificial Sequence: Synthetic
      Light Chain

<400> SEQUENCE: 63

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val Tyr Ser Asp Gly Asn Thr His Leu His Trp Tyr Leu Gln Lys Thr
    50                  55                  60

Gly Gln Ser Pro Lys Leu Leu Ile Tyr Lys Ala Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Leu Thr Phe Gly Ala Gly Thr Lys Leu
        115                 120                 125

Glu Leu Lys Arg Ala Asp Ala Ala Pro Thr Val Ser Ile Phe Pro Pro
    130                 135                 140
```

```
Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
            195                 200                 205

Glu Tyr Glu Arg His Asn Ser Tyr Thr Cys Glu Ala Thr His Lys Thr
210                 215                 220

Ser Thr Ser Pro Ile Val Lys Ser Phe Asn Arg Gly Glu Cys
225                 230                 235

<210> SEQ ID NO 64
<211> LENGTH: 323
<212> TYPE: PRT
<213> ORGANISM: Artificial Sequence
<220> FEATURE:
<223> OTHER INFORMATION: Description of Artificial Sequence: Synthetic
      Rabbit IgG

<400> SEQUENCE: 64

Gly Gln Pro Lys Ala Pro Ser Val Phe Pro Leu Ala Pro Cys Cys Gly
1               5                   10                  15

Asp Thr Pro Ser Ser Thr Val Thr Leu Gly Cys Leu Val Lys Gly Tyr
            20                  25                  30

Leu Pro Glu Pro Val Thr Val Thr Trp Asn Ser Gly Thr Leu Thr Asn
        35                  40                  45

Gly Val Arg Thr Phe Pro Ser Val Arg Gln Ser Ser Gly Leu Tyr Ser
    50                  55                  60

Leu Ser Ser Val Val Ser Val Thr Ser Ser Gln Pro Val Thr Cys
65                  70                  75                  80

Asn Val Ala His Pro Ala Thr Asn Thr Lys Val Asp Lys Thr Val Ala
                85                  90                  95

Pro Ser Thr Cys Ser Lys Pro Thr Cys Pro Pro Pro Glu Leu Leu Gly
            100                 105                 110

Gly Pro Ser Val Phe Ile Phe Pro Pro Lys Pro Lys Asp Thr Leu Met
        115                 120                 125

Ile Ser Arg Thr Pro Glu Val Thr Cys Val Val Val Asp Val Ser Gln
    130                 135                 140

Asp Asp Pro Glu Val Gln Phe Thr Trp Tyr Ile Asn Asn Glu Gln Val
145                 150                 155                 160

Arg Thr Ala Arg Pro Pro Leu Arg Glu Gln Gln Phe Asn Ser Thr Ile
                165                 170                 175

Arg Val Val Ser Thr Leu Pro Ile Thr His Gln Asp Trp Leu Arg Gly
            180                 185                 190

Lys Glu Phe Lys Cys Lys Val His Asn Lys Ala Leu Pro Ala Pro Ile
        195                 200                 205

Glu Lys Thr Ile Ser Lys Ala Arg Gly Gln Pro Leu Glu Pro Lys Val
    210                 215                 220

Tyr Thr Met Gly Pro Pro Arg Glu Glu Leu Ser Ser Arg Ser Val Ser
225                 230                 235                 240

Leu Thr Cys Met Ile Asn Gly Phe Tyr Pro Ser Asp Ile Ser Val Glu
                245                 250                 255

Trp Glu Lys Asn Gly Lys Ala Glu Asp Asn Tyr Lys Thr Thr Pro Ala
```

```
                    260               265                 270
Val Leu Asp Ser Asp Gly Ser Tyr Phe Leu Tyr Asn Lys Leu Ser Val
            275                 280                 285

Pro Thr Ser Glu Trp Gln Arg Gly Asp Val Phe Thr Cys Ser Val Met
        290                 295                 300

His Glu Ala Leu His Asn His Tyr Thr Gln Lys Ser Ile Ser Arg Ser
305                 310                 315                 320

Pro Gly Lys

<210> SEQ ID NO 65
<211> LENGTH: 330
<212> TYPE: PRT
<213> ORGANISM: Artificial Sequence
<220> FEATURE:
<223> OTHER INFORMATION: Description of Artificial Sequence: Synthetic
      Human IgG

<400> SEQUENCE: 65

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
```

```
                290                 295                 300
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ccgtctgtgc cttctcatct g                                                21

<210> SEQ ID NO 67
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
agtccaagag tyctcttatg yaagaccctt                                       29

<210> SEQ ID NO 68
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 68
cttcgcttca cctctgc                                                     17

<210> SEQ ID NO 69
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Arg Pro Phe Ser Gly Ser Leu Gly Thr Leu Ser Ser Pro Ser Pro
1               5                   10                  15

Ser Ala Val Pro Thr Asp His Gly
                20

<210> SEQ ID NO 70
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Arg Pro Leu Ser Gly Pro Leu Gly Thr Leu Ser Ser Pro Ser Pro
1               5                   10                  15

Ser Ala Val Pro Ala Asp His Gly
```

```
<210> SEQ ID NO 71
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Arg Pro Leu Pro Gly Pro Leu Gly Ala Leu Pro Pro Ala Ser Pro
1               5                   10                  15

Pro Val Val Pro Thr Asp His Gly
            20

<210> SEQ ID NO 72
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Arg Pro Val Ser Gly Pro Phe Gly Thr Leu Pro Ser Pro Ser Ser
1               5                   10                  15

Ser Ala Val Pro Ala Asp His Gly
            20

<210> SEQ ID NO 73
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Arg Pro Val Ser Gly Ser Leu Gly Asp Leu Ser Ser Pro Ser Pro
1               5                   10                  15

Ser Ala Val Pro Ala Asp His Gly
            20

<210> SEQ ID NO 74
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Leu Ala Tyr
1

<210> SEQ ID NO 75
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Leu Ala
```

```
<210> SEQ ID NO 76
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Lys Ala Ser
1
```

What is claimed is:

1. An isolated polynucleotide encoding an antibody, or an antigen-binding fragment thereof, comprising
(i) a VH-complementarity determining region (CDR) 1 comprising
the amino acid sequence of SEQ ID NO:1, or SEQ ID NO:1 having 1 conservative substitution,
the amino acid sequence of SEQ ID NO:6, or SEQ ID NO:6 having 1 or 2 conservative substitutions,
the amino acid sequence of SEQ ID NO:11, or SEQ ID NO:11 having 1 or 2 conservative substitutions, or
the amino acid sequence of SEQ ID NO:15, or SEQ ID NO:15 having from 1 to 3 conservative substitutions;
(ii) a VH-CDR2 comprising
the amino acid sequence of SEQ ID NO:2, or SEQ ID NO:2 having from 1 to 4 conservative substitutions,
the amino acid sequence of SEQ ID NO:7, or SEQ ID NO:7 having 1 or 2 conservative substitutions,
the amino acid sequence of SEQ ID NO:12, or SEQ ID NO:12 having 1 conservative substitution, or
the amino acid sequence of SEQ ID NO:16, or SEQ ID NO:16 having from 1 to 4 conservative substitutions;
(iii) a VH-CDR3 comprising
the amino acid sequence LAY,
the amino acid sequence of SEQ ID NO:8, or SEQ ID NO:8 having 1 conservative substitution,
an alanine residue, or
the amino acid sequence LA;
(iv) a VL-CDR1 comprising
the amino acid sequence of SEQ ID NO:3, or SEQ ID NO:3 having from 1 to 4 conservative substitutions,
the amino acid sequence of SEQ ID NO:9, or SEQ ID NO:9 having 1 or 2 conservative substitutions,
the amino acid sequence of SEQ ID NO:13, or SEQ ID NO:13 having from 1 to 3 conservative substitutions, or
the amino acid sequence of SEQ ID NO:17, or SEQ ID NO:17 having from 1 to 3 conservative substitutions;
(v) a VL-CDR2 comprising
the amino acid sequence of SEQ ID NO:4, or SEQ ID NO:4 having 1 or 2 conservative substitutions,
the amino acid sequence KAS, or
the amino acid sequence of SEQ ID NO:18, or SEQ ID NO:18 having from 1 to 3 conservative substitutions; and
(vi) a VL-CDR3 comprising
the amino acid sequence of SEQ ID NO:5, or SEQ ID NO:5 having 1 or 2 conservative substitutions,
the amino acid sequence of SEQ ID NO:10, or SEQ ID NO:10 having 1 or 2 conservative substitutions,
the amino acid sequence of SEQ ID NO:14, or SEQ ID NO:14 having 1 conservative substitution, or
the amino acid sequence of SEQ ID NO:19, or SEQ ID NO:19 having 1 conservative substitution.

2. The polynucleotide of claim 1, encoding an antibody or antigen-binding fragment comprising:
(i) a VH-CDR1 comprising the amino acid sequence of SEQ ID NO:1, or SEQ ID NO:1 having 1 conservative substitution;
(ii) a VH-CDR2 comprising the amino acid sequence of SEQ ID NO:2, or SEQ ID NO:2 having from 1 to 4 conservative substitutions;
(iii) a VH-CDR3 comprising the amino acid sequence LAY;
(iv) a VL-CDR1 comprising the amino acid sequence of SEQ ID NO:3, or SEQ ID NO:3 having from 1 to 4 conservative substitutions;
(v) a VL-CDR2 comprising the amino acid sequence of SEQ ID NO:4, or SEQ ID NO:4 having 1 or 2 conservative substitutions; and
(vi) a VL-CDR3 comprising the amino acid sequence of SEQ ID NO:5, or SEQ ID NO:5 having 1 or 2 conservative substitutions.

3. The polynucleotide of claim 2, encoding an antibody or antigen-binding fragment, comprising:
(i) a VH-CDR1 comprising the amino acid sequence of SEQ ID NO:1;
(ii) a VH-CDR2 comprising the amino acid sequence of SEQ ID NO:2;
(iii) a VH-CDR3 comprising the amino acid sequence LAY;
(iv) a VL-CDR1 comprising the amino acid sequence of SEQ ID NO:3;
(v) a VL-CDR2 comprising the amino acid sequence of SEQ ID NO:4; and
(vi) a VL-CDR3 comprising the amino acid sequence of SEQ ID NO:5.

4. The polynucleotide of claim 1, encoding an antibody or antigen-binding fragment, comprising:
(i) a VH-CDR1 comprising the amino acid sequence of SEQ ID NO:6 or SEQ ID NO:6 having 1 or 2 conservative substitutions;
(ii) a VH-CDR2 comprising the amino acid sequence of SEQ ID NO:7, or SEQ ID NO:7 having 1 or 2 conservative substitutions;
(iii) a VH-CDR3 comprising the amino acid sequence of SEQ ID NO:8, or SEQ ID NO:8 having 1 conservative substitution;
(iv) a VL-CDR1 comprising the amino acid sequence of SEQ ID NO:9, or SEQ ID NO:9 having 1 or 2 conservative substitutions;

(v) a VL-CDR2 comprising the amino acid sequence KAS; and (vi) a VL-CDR3 comprising the amino acid sequence of SEQ ID NO:10, or SEQ ID NO:10 having 1 or 2 conservative substitutions.

5. The polynucleotide of claim 4, encoding an antibody or antigen-binding fragment comprising:
   (i) a VH-CDR1 comprising the amino acid sequence of SEQ ID NO:6;
   (ii) a VH-CDR2 comprising the amino acid sequence of SEQ ID NO:7;
   (iii) a VH-CDR3 comprising the amino acid sequence of SEQ ID NO:8;
   (iv) a VL-CDR1 comprising the amino acid sequence of SEQ ID NO:9;
   (v) a VL-CDR2 comprising the amino acid sequence KAS; and
   (vi) a VL-CDR3 comprising the amino acid sequence of SEQ ID NO:10.

6. The polynucleotide of claim 1, encoding an antibody or antigen-binding fragment comprising:
   (i) a VH-CDR1 comprising the amino acid sequence of SEQ ID NO:11, or SEQ ID NO:11 having 1 or 2 conservative substitutions;
   (ii) a VH-CDR2 comprising the amino acid sequence of SEQ ID NO:12, or SEQ ID NO:12 having 1 conservative substitution;
   (iii) a VH-CDR3 comprising an alanine residue;
   (iv) a VL-CDR1 comprising the amino acid sequence of SEQ ID NO:13, or SEQ ID NO:13 having from 1 to 3 conservative substitutions;
   (v) a VL-CDR2 comprising the amino acid sequence KAS; and
   (vi) a VL-CDR3 comprising the amino acid sequence of SEQ ID NO:14, or SEQ ID NO:14 having 1 conservative substitution.

7. The polynucleotide of claim 6, encoding an antibody or antigen-binding fragment comprising:
   (i) a VH-CDR1 comprising the amino acid sequence of SEQ ID NO:11;
   (ii) a VH-CDR2 comprising the amino acid sequence of SEQ ID NO:12;
   (iii) a VH-CDR3 comprising an alanine residue;
   (iv) a VL-CDR1 comprising the amino acid sequence of SEQ ID NO:13;
   (v) a VL-CDR2 comprising the amino acid sequence KAS; and
   (vi) a VL-CDR3 comprising the amino acid sequence of SEQ ID NO:14.

8. The polynucleotide of claim 1, encoding an antibody or antigen-binding fragment comprising:
   (i) a VH-CDR1 comprising the amino acid sequence of SEQ ID NO:15, or SEQ ID NO:15 having from 1 to 3 conservative substitutions;
   (ii) a VH-CDR2 comprising the amino acid sequence of SEQ ID NO:16, or SEQ ID NO:16 having from 1 to 4 conservative substitutions;
   (iii) a VH-CDR3 comprising the amino acid sequence LA;
   (iv) a VL-CDR1 comprising the amino acid sequence of SEQ ID NO:17, or SEQ ID NO:17 having from 1 to 3 conservative substitutions;
   (v) a VL-CDR2 comprising the amino acid sequence of SEQ ID NO:18, or SEQ ID NO:18 having from 1 to 3 conservative substitutions; and
   (vi) a VL-CDR3 comprising the amino acid sequence of SEQ ID NO:19, or SEQ ID NO:19 having 1 conservative substitution.

9. The polynucleotide of claim 8, encoding an antibody or antigen-binding fragment comprising:
   (i) a VH-CDR1 comprising the amino acid sequence of SEQ ID NO:15;
   (ii) a VH-CDR2 comprising the amino acid sequence of SEQ ID NO:16;
   (iii) a VH-CDR3 comprising the amino acid sequence LA;
   (iv) a VL-CDR1 comprising the amino acid sequence of SEQ ID NO:17;
   (v) a VL-CDR2 comprising the amino acid sequence of SEQ ID NO:18; and
   (vi) a VL-CDR3 comprising the amino acid sequence of SEQ ID NO:19.

10. The polynucleotide of claim 1, encoding an antibody or antigen-binding fragment comprising a VH region comprising an amino acid sequence that is at least 70% identical to SEQ ID NO: 21 or 22, wherein the amino acid sequence of the VH region has from 0 to 30 amino acid substitutions, from 0 to 5 amino acid insertions, and/or from 0 to 5 amino acid deletions compared to SEQ ID NO: 21 or 22.

11. The polynucleotide of claim 1, encoding an antibody or antigen-binding fragment, comprising a VL region comprising an amino acid sequence that is at least 70% identical to SEQ ID NO: 23 or 24, wherein the amino acid sequence of the VL region has from 0 to 30 amino acid substitutions, from 0 to 5 amino acid insertions, and/or from 0 to 5 amino acid deletions compared to SEQ ID NO: 23 or 24.

12. The polynucleotide of claim 10, encoding an antibody or antigen-binding fragment comprising 1 to 30 amino acid substitutions, wherein at least 1 of the amino acid substitutions is a conservative substitution mutation.

13. The polynucleotide of claim 12, encoding an antibody or antigen-binding fragment, wherein all of the amino acid substitutions are conservative substitution mutations.

14. The polynucleotide of claim 1, encoding an antibody or antigen-binding fragment comprising a heavy chain constant region comprising an amino acid sequence that is at least 70% identical to SEQ ID NO: 25.

15. The polynucleotide of claim 1, encoding an antibody or antigen-binding fragment comprising a light chain constant region comprising an amino acid sequence that is at least 70% identical to SEQ ID NO: 26.

16. The polynucleotide of claim 1, encoding an antibody or antigen-binding fragment comprising an IgA, IgD, IgE, IgG, or IgM heavy chain constant region.

17. The polynucleotide of claim 16, encoding an antibody or antigen-binding fragment comprising a mouse, rabbit, goat, rat, or human IgG heavy chain constant region.

18. The polynucleotide of claim 1, encoding an antibody or antigen-binding fragment 7, comprising a kappa light chain or a lambda light chain.

19. The polynucleotide of claim 1, encoding an antibody or antigen-binding fragment 8, which is a linear antibody or a diabody.

20. The polynucleotide of claim 1, encoding an antibody or antigen-binding fragment which is an intrabody.

21. The polynucleotide of claim 20, encoding an antibody or antigen-binding fragment further comprising a nuclear localization signal or a mitochondrial localization signal.

22. The polynucleotide of claim 1, encoding an antibody or antigen-binding fragment which is a monoclonal antibody.

23. The polynucleotide of claim 22, encoding an antibody or antigen-binding fragment which is a humanized antibody or a chimeric antibody.

24. The polynucleotide of claim 1, encoding an antibody or antigen-binding fragment which is a scFv, sc(Fv)2, Fab, F(ab)2, Fab', F(ab')2, or Fv fragment.

25. A vector comprising the polynucleotide of claim 1.

26. A cell comprising the polynucleotide of claim 1.

27. A pharmaceutical composition comprising the polynucleotide of claim 1.

* * * * *